US010596237B2

(12) United States Patent
Kolls et al.

(10) Patent No.: US 10,596,237 B2
(45) Date of Patent: Mar. 24, 2020

(54) IDENTIFICATION OF PNEUMOCYSTIS ANTIGENS AND USES THEREOF

(71) Applicants: University of Pittsburgh—Of the Commonwealth System of Higher Education, Pittsburgh, PA (US); University of New Orleans, New Orleans, LA (US); Board of Supervisors of Louisiana State University and Agricultural and Mechanical College, Baton Rough, LA (US)

(72) Inventors: Jay Kennedy Kolls, Pittsburgh, PA (US); Mingquan Michael Zheng, Upper St. Clair, PA (US); Yang Cai, New Orleans, LA (US); Taylor John Eddens, Pittsburgh, PA (US); David M. Ricks, Pittsburgh, PA (US)

(73) Assignees: University of Pittsburgh—Of the Commonwealth System of Higher Education, Pittsburgh, PA (US); University of New Orleans, New Orleans, LA (US); Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 12 days.

(21) Appl. No.: 15/127,383

(22) PCT Filed: Mar. 19, 2015

(86) PCT No.: PCT/US2015/021573
§ 371 (c)(1),
(2) Date: Sep. 19, 2016

(87) PCT Pub. No.: WO2015/143220
PCT Pub. Date: Sep. 24, 2015

(65) Prior Publication Data

US 2017/0173126 A1 Jun. 22, 2017

Related U.S. Application Data

(60) Provisional application No. 61/968,802, filed on Mar. 21, 2014.

(51) Int. Cl.

| | |
|---|---|
| ***A61K 39/00*** | (2006.01) |
| ***C07K 14/39*** | (2006.01) |
| ***A61K 38/00*** | (2006.01) |
| ***C12Q 1/689*** | (2018.01) |
| ***G01N 33/569*** | (2006.01) |
| ***C07K 14/37*** | (2006.01) |
| ***G01N 33/68*** | (2006.01) |

(52) U.S. Cl.
CPC .......... *A61K 39/0002* (2013.01); *A61K 38/00* (2013.01); *C07K 14/37* (2013.01); *C07K 14/39* (2013.01); *C12Q 1/689* (2013.01); *G01N 33/56961* (2013.01); *G01N 33/6893* (2013.01); *C12Q 2600/118* (2013.01); *C12Q 2600/158* (2013.01); *G01N 2333/37* (2013.01); *G01N 2800/26* (2013.01)

(58) Field of Classification Search
None
See application file for complete search history.

(56) References Cited

PUBLICATIONS

Greenspan et al. (Nature Biotechnology 7: 936-937, 1999) (Year: 1999).*
Bishop, L. R. et al., "Discordant antibody and cellular responses to *Pneumocystis* major surface glycoprotein variants in mice," *BMC Immunol.*, 13(39):1-11, 2012.
GenBank Accession No. AAG02216, Dec. 18, 2000.
GenBank Accession No. AF191096, Dec. 18, 2000.
GenBank Accession No. XM_007875184, Jul. 25, 2014.
GenBank Accession No. XP_007873375, Jul. 25, 2014.
International Search Report and Written Opinion of the International Searching Authority, dated May 28, 2015, for corresponding International Application No. PCT/US2015/021573, 11 pages.
Ito, M. et al., "Prophylactic effect of FK463, a novel antifungal lipopeptide, against *Pneumocystis carinii* infection in mice," *Antimicrob Agents Chemother.*, 44(9):2259-2262, 2000.
Kottom, T. J. et al., "Cell Wall Assembly by *Pneumocystis carinii*," J *Biol Chem*, 275(51):40628-40634, 2000.
Kottom, T. J. et al., "The *Pneumocystis* Ace2 Transcription Factor Regulates Cell Wall-remodeling Genes and Organism Virulence," *J Biol Chem.*, 288(33):23893-23902, 2013.

(Continued)

*Primary Examiner* — Robert A Zeman
(74) *Attorney, Agent, or Firm* — Klarquist Sparkman LLP

(57) ABSTRACT

Pneumonia due to the fungus *Pneumocystis jirovecii* is a life-threatening infection that occurs in immunocompromised patients. The inability to culture the organism as well as the lack of a sequenced genome has hindered antigen discovery that could be useful in developing effective vaccines, therapeutic antibodies and diagnostic methods. A method of surface proteomics of *Pneumocystis murina* that reliably detects surface proteins that are conserved in *Pneumocystis jirovecii* is described. In particular, eight identified *P. murina* surface proteins are described. Methods of eliciting immune responses against the identified proteins, generating therapeutic antibodies against the identified proteins, as well as diagnostic methods based on the identified peptides are described.

9 Claims, 20 Drawing Sheets

Specification includes a Sequence Listing.

(56) References Cited

PUBLICATIONS

Lundgren, B. et al., "Purification and characterization of a major human *Pneumocystis carinii* surface antigen," *J Clin Invest*, 87(1):163-170, 1991.

Puckett, A.D. Jr. et al., "The Repair Potential of a Posterior Composite Material," *J MS Dent Assoc.*, 42:12-13, 1986.

Zheng, M. et al., "Novel *Pneumocystis* Antigen Discovery Using Fungal Surface Proteomics," *Infect Immun.*, 82(6):2417-2423, 2014.

* cited by examiner

FIG. 1B

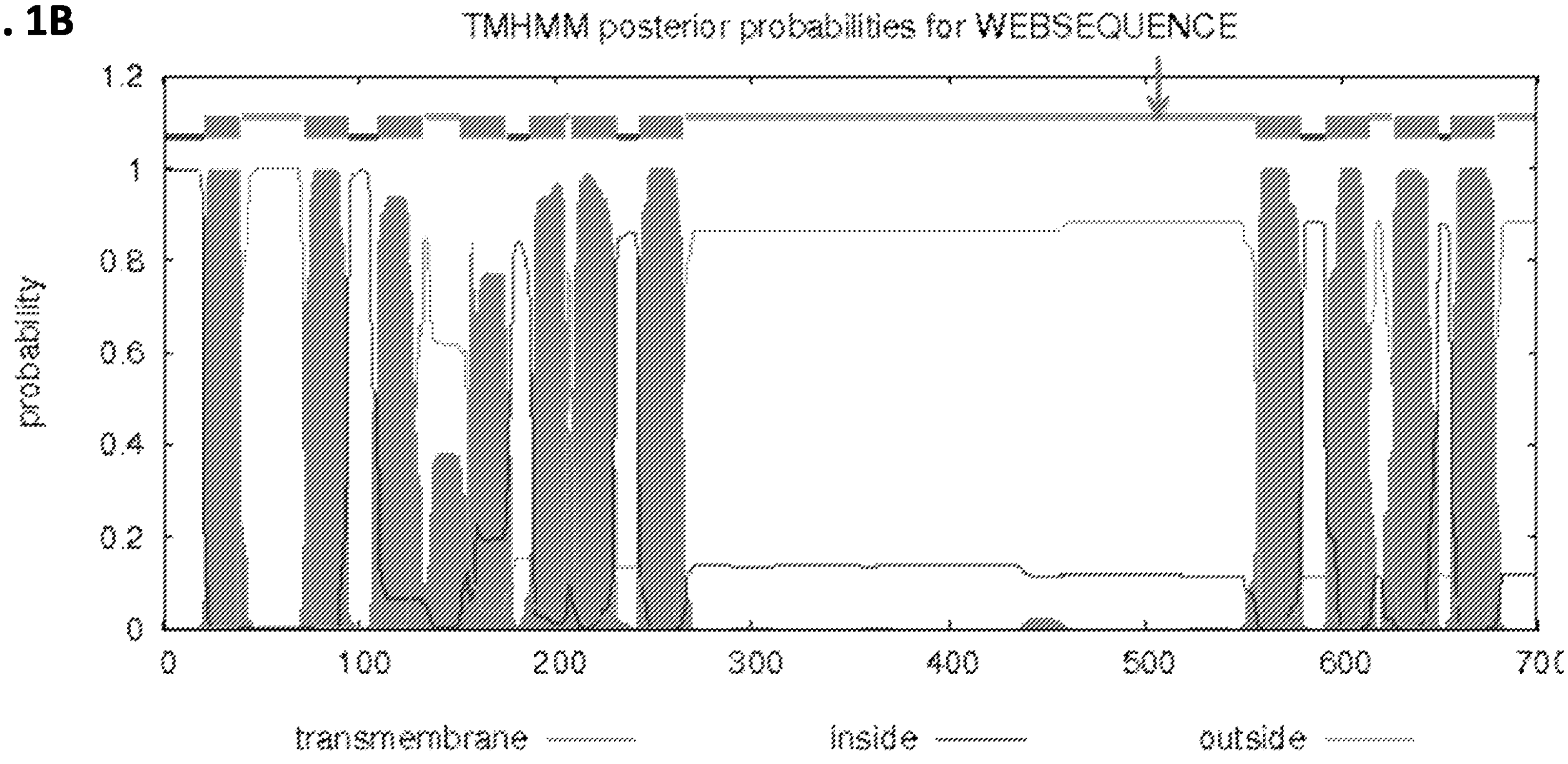

MVYNFNNLIGQPNIKLRINDIKYLIILTIIGSCVQTYMINHPSDLVFNESYMMQLAYNYIKKEFYIDKDPPYARMLYALFIWV
LGHLPVNLYTIKKAYSLYRIPRIPTRLFSCIFGILLSPITYLTLRVMRFTRNTAILGSILIIFESSVVIQSRFVFHDSLALFFTAL
THLFWRLFESCQQIPFRKAWWAYLMATGFTLGALISTKWVGIFTFFWIGLLACLQLWHFIEDLTMALTTWVKHFFFRFF
SLIIIPTLFYIITFYLHINLLKNANDGVFLSPEFLSTFDNRIVKSVPAPVSYGSTVTIRHLNSPYGYLHSHFDSYPSGSKQQ
QVTLYLYEDANNNWLITDSGDANYEVFSFSTIQDGSIIRLYHLETNRRLHSHDVRPSLSDIDWQNEVSGYGHKGFPGD
HNDLFRIEIDKSRSYTDESKISVRAIETKFRLIHVSTGCALFSNNIYLPEW**GHGQIEVTCAK*SGIYENSLWYIEDNSH**DD
FSINIEKVSYKKIAFFQKFFELHKHMWEENFHLEDLYNAGTHPFSWPFLRRGIHFWIKKNDQIYFLGNPLIWLLTLAFVG
VYCIFKLFVILSEQRGYPSYNDKVYLRYDYLIGTSLLGWIFHYFPYYFMEKQFLLSQYIPALYFSILSLCSFWDFISVRFLQ
RLQIKLFTLFFFKIVISVYFIMAPLIYGYSMRKEHCSFIKFFKTWDLRC

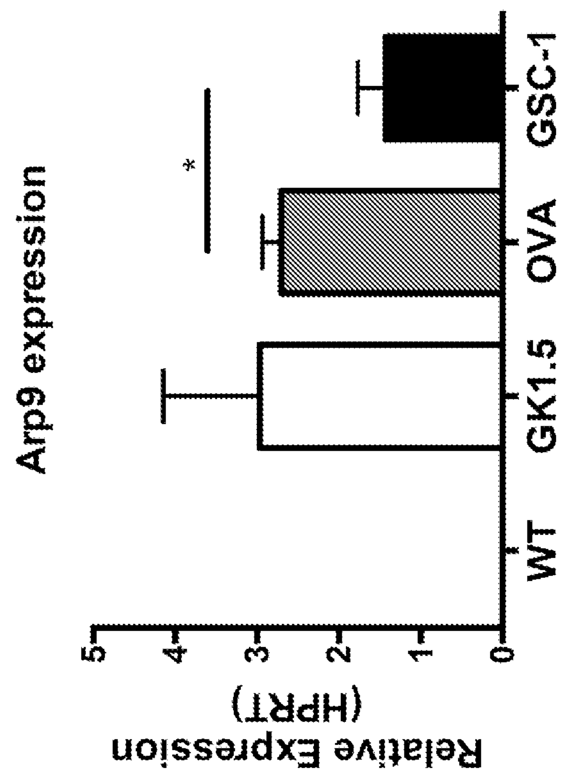
FIG. 19
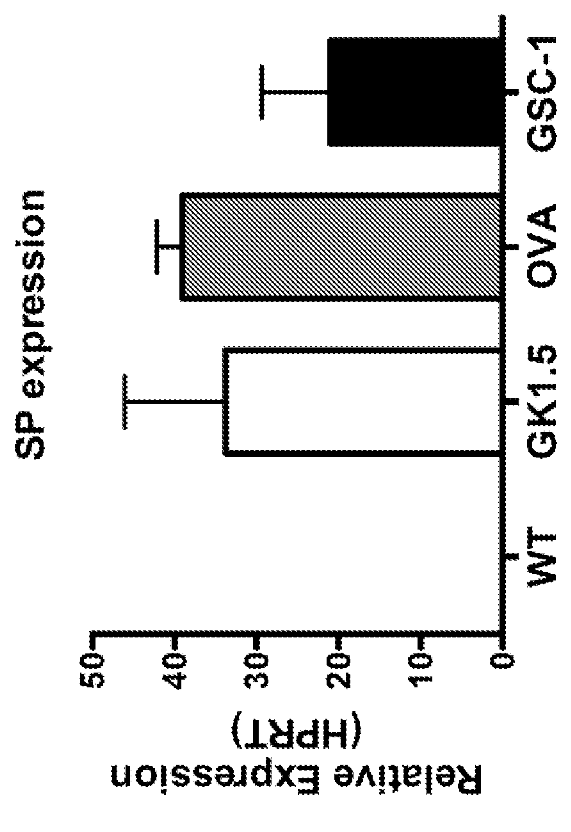

SEQUENCE LISTING

```
<160> NUMBER OF SEQ ID NOS: 232

<210> SEQ ID NO 1
<211> LENGTH: 546
<212> TYPE: PRT
<213> ORGANISM: Schizosaccharomyces pombe

<400> SEQUENCE: 1

Met Gly Lys Asn Leu Thr Ile Val Met Leu Val Phe Val Ser Met Ala
1               5                   10                  15

Gly Trp Met Phe Gly Ala Asp Thr Gly Ser Ile Gly Gly Ile Thr Asn
            20                  25                  30

Met Arg Asp Phe Gln Ser Arg Phe Ala Asp Arg Tyr Asn Pro Val Thr
        35                  40                  45

Asp Ser Tyr Ser Tyr Ser Ser Ala Arg Gln Gly Leu Ile Thr Gly Met
    50                  55                  60
```

-continued

```
Val Asn Val Gly Ser Phe Phe Gly Cys Phe Leu Ser Ser Pro Leu Met
65                  70                  75                  80

Asp Arg Ile Gly Lys Arg Thr Ser Ile Met Phe Trp Thr Ile Val Tyr
                85                  90                  95

Leu Ile Gly Ile Ile Leu Gln Val Thr Ala Val Pro Ser Trp Val Gln
            100                 105                 110

Ile Met Val Ala Lys Ile Trp Thr Gly Leu Ser Ile Gly Ala Leu Ser
        115                 120                 125

Val Leu Ala Pro Gly Phe Gln Ser Glu Val Ala Pro Ala Asp Leu Arg
    130                 135                 140

Gly Thr Ile Val Thr Thr Tyr Gln Leu Ala Val Thr Gly Gly Ile Phe
145                 150                 155                 160

Ile Ala Ala Cys Ile Asn Met Gly Thr His Lys Leu His Lys Thr Ala
                165                 170                 175

Gln Trp Arg Val Ser Met Gly Ile Asn Leu Leu Trp Gly Ile Ile Thr
            180                 185                 190

Phe Ile Gly Ile Ser Phe Leu Pro Glu Ser Pro Arg Tyr Leu Ile Ser
        195                 200                 205

Val Gly Arg Asp Glu Glu Ala Leu Gln Ile Met Ala Lys Asn Asn Asp
    210                 215                 220

Leu Pro Ile Glu His Glu Val Ile Gln Thr Glu Tyr His Val Ile Lys
225                 230                 235                 240

Ser Asp Cys Glu Ala Glu Leu Ala Gly Gly Pro Ala Thr Trp Pro Glu
                245                 250                 255

Ile Phe Gly Pro Asp Ile Arg Tyr Arg Thr Phe Leu Gly Leu Gly Val
            260                 265                 270

Met Ser Leu Gln Gln Leu Thr Gly Asp Asn Tyr Tyr Phe Tyr Tyr Gly
        275                 280                 285

Phe Glu Val Phe Glu Gly Thr Gly Met Asn Ser Pro Tyr Leu Ser Ala
    290                 295                 300

Leu Ile Leu Asp Ala Val Asn Phe Gly Cys Thr Phe Gly Gly Leu Phe
305                 310                 315                 320

Val Leu Glu Phe Phe Gly Arg Arg Met Pro Leu Ile Ile Gly Ala Leu
                325                 330                 335

Trp Gln Ser Ile Thr Phe Phe Ile Tyr Ala Ala Val Gly Asn Arg Ala
            340                 345                 350

Leu Thr Arg Lys Asn Gly Thr Ser Asn His Arg Ala Gly Ala Val Met
        355                 360                 365

Ile Val Phe Ser Cys Leu Phe Ile Phe Ser Phe Ala Gln Thr Trp Gly
    370                 375                 380

Pro Ala Ala Tyr Val Ile Val Gly Glu Ser Tyr Pro Ile Arg Tyr Arg
385                 390                 395                 400

Ser Lys Cys Ala Ala Val Ala Thr Thr Gly Asn Trp Leu Trp Gly Phe
                405                 410                 415

Leu Ile Ser Phe Phe Thr Pro Phe Ile Thr Asn Ser Ile Gly Phe Lys
            420                 425                 430

Tyr Gly Tyr Ile Phe Ala Ala Cys Asn Leu Cys Ala Ala Cys Ile Ile
        435                 440                 445

Phe Leu Phe Ala His Glu Thr Lys Gly Leu Thr Leu Glu Glu Ile Asn
    450                 455                 460

Glu Leu Tyr Ile Ser Gly Ala Lys Pro Trp Met Pro Arg Pro Lys Asn
465                 470                 475                 480
```

-continued

```
Leu Gly Asn Phe Thr Lys Gln Gln Glu Glu Val Arg Glu Lys Ser Arg
                485                 490                 495

Gly Val Gln Gly Glu Ser Ala Ala His Leu Glu Asn Val Asp Gly Glu
            500                 505                 510

Glu Gly Ile Glu Asp Ser Ser Asn Asp Ile Ser Ser Thr Thr Ser Ser
        515                 520                 525

Asp Gly Arg Ala Lys Pro Glu Ser Ser Tyr His Asp Gln Glu Glu Gln
    530                 535                 540

Phe Ala
545
```

<210> SEQ ID NO 2
<211> LENGTH: 1944
<212> TYPE: PRT
<213> ORGANISM: Pneumocystis carinii

<400> SEQUENCE: 2

```
Met Ser Gln Gln Gln His Tyr Tyr Asp Asp Ser Tyr Pro Gly Gln Asn
1               5                   10                  15

Gly Ala Tyr Tyr Gly Glu His Ser Tyr Gly Asn Ser Gly Phe Asn Asn
            20                  25                  30

Gly Ser Tyr Ala Ser Gly Gly Tyr Glu His Gly Glu Tyr Tyr Ala Pro
        35                  40                  45

Glu Tyr Gly Gln Glu Tyr Tyr Asp Glu Tyr Asp Ser Gly Gly Met Met
    50                  55                  60

Tyr Asp Gly His Pro Arg Glu Met Tyr Asn Thr Gly Glu Thr Gly Tyr
65                  70                  75                  80

Tyr Arg Gln Asp Asp Arg Tyr Tyr Asp Tyr Pro Gln Asp Gly Tyr Ile
                85                  90                  95

Pro Asp Thr Tyr Gly Ile Tyr Lys Tyr Tyr Leu Arg Ser Asn Ala Tyr
            100                 105                 110

Phe Glu Gly His Asp Glu Tyr His Met Tyr Asp Arg Lys Gly Lys Arg
        115                 120                 125

Arg Gly Ser Ser Glu Gly Ser Glu Thr Phe Ser Asp Phe Thr Met Arg
    130                 135                 140

Ser Asp Met Ala Arg Ala Ala Glu Phe Asp Ser Tyr Gly Arg Phe Asp
145                 150                 155                 160

Glu Gln Tyr Arg Ser Tyr Gly Pro Ser Ser Glu Ser Leu Asn Gln Met
                165                 170                 175

Ala Ser Arg Gln Arg Gly Tyr Arg Pro Asp Ser Gln Ile Ser Tyr Thr
            180                 185                 190

Gly Asn Arg Ser Ser Gly Ala Ser Thr Pro Ile Tyr Gly Met Tyr Tyr
        195                 200                 205

Asn Gln Ala Ala Met Met Thr Ser Ala Arg Ser Arg Glu Pro Tyr Pro
    210                 215                 220

Ala Trp Thr Ala Glu Asn Gln Ile Pro Val Ser Lys Glu Glu Ile Glu
225                 230                 235                 240

Asp Ile Phe Ile Asp Leu Thr Asn Lys Phe Gly Phe Gln Arg Asp Ser
                245                 250                 255

Met Arg Asn Met Tyr Asp His Met Met Val Leu Leu Asp Ser Arg Ala
            260                 265                 270

Ser Arg Met Thr Pro Asn Gln Ala Leu Leu Ser Leu His Ala Asp Tyr
        275                 280                 285

Ile Gly Gly Asp Asn Ala Asn Tyr Arg Asn Trp Tyr Phe Ala Ala Gln
    290                 295                 300
```

-continued

```
Phe Asp Leu Asp Asp Ala Val Gly Phe Ser Asn Met Asp Leu Gly Lys
305                 310                 315                 320

Asn Arg Lys Ser Ser Tyr Ser Gln Lys Pro Ser Lys Lys Phe Gln Lys
                325                 330                 335

Asn Ser Ala Ser Lys Asn Ile Leu Gln Ala Leu Asp Gly Asp Asn Ser
            340                 345                 350

Leu Glu Ser Ala Ile Tyr Arg Trp Lys Thr Arg Cys Thr Gln Met Ser
        355                 360                 365

Gln Tyr Asp Arg Ala Arg Glu Leu Ala Leu Tyr Leu Leu Cys Trp Gly
    370                 375                 380

Glu Ala Asn Gln Val Arg Phe Thr Pro Glu Cys Leu Cys Phe Ile Phe
385                 390                 395                 400

Lys Cys Ala Asn Asp Tyr Leu Asn Ser Pro Gln Cys Gln Ala Met Val
                405                 410                 415

Glu Pro Ala Pro Glu Gly Ser Tyr Leu Asn Asp Val Ile Thr Pro Leu
            420                 425                 430

Tyr Ala Tyr Met Arg Asp Gln Gly Tyr Glu Ile Ile Asn Gly Arg Tyr
        435                 440                 445

Val Arg Arg Glu Arg Asp His Asn Lys Ile Ile Gly Tyr Asp Asp Ile
    450                 455                 460

Asn Gln Leu Phe Trp Tyr Pro Glu Gly Ile Gln Arg Ile Val Leu Ser
465                 470                 475                 480

Asp Lys Thr Arg Met Val Asp Leu Pro Leu Asp Gln Arg Tyr Pro Arg
                485                 490                 495

Phe Lys Asp Val Val Trp Lys Lys Ala Phe Phe Lys Thr Tyr Arg Glu
            500                 505                 510

Thr Arg Ser Trp Phe His Leu Phe Thr Asn Phe Asn Arg Ile Trp Ile
        515                 520                 525

Ile His Ile Thr Val Tyr Trp Phe Tyr Thr Ala Ala Asn Ser Pro Thr
    530                 535                 540

Val Tyr Thr His Asn Tyr Gln Gln Ser Leu Asp Asn Gln Pro Pro Phe
545                 550                 555                 560

Ala Tyr Arg Met Ser Ala Val Gly Phe Gly Gly Gly Val Ala Ser Leu
                565                 570                 575

Leu Met Ile Val Ala Thr Leu Ala Glu Trp Ala Tyr Val Pro Arg Lys
            580                 585                 590

Trp Pro Gly Ala Gln His Leu Thr Arg Arg Leu Leu Phe Leu Ile Leu
        595                 600                 605

Phe Phe Ile Ile Asn Val Ala Pro Gly Val Tyr Val Ile Lys Phe Ala
    610                 615                 620

Pro Trp Lys Pro Asn Val Ser Ile Val Thr Thr Leu Ile Ser Ile Met
625                 630                 635                 640

His Phe Leu Ile Ala Ile Phe Thr Phe Leu Phe Phe Ala Ile Met Pro
                645                 650                 655

Leu Gly Gly Leu Phe Gly Asn Tyr Leu Tyr Lys Lys Thr Arg Arg Tyr
            660                 665                 670

Val Ala Ser Gln Thr Phe Thr Ala Asn Phe Ala Lys Leu Lys Gly Asn
        675                 680                 685

Asp Leu Trp Leu Ser Tyr Gly Leu Trp Ile Ala Val Phe Ala Cys Lys
    690                 695                 700

Phe Ala Glu Ser Tyr Phe Phe Leu Ser Leu Ser Leu Arg Asp Pro Ile
705                 710                 715                 720
```

-continued

```
Arg Tyr Leu Asn Thr Met Thr Ile Gly His Cys Gly Ile Arg Tyr Leu
                725                 730                 735

Gly Ser Ser Leu Cys Pro Tyr Gln Ala Lys Ile Thr Leu Gly Ile Met
            740                 745                 750

Tyr Ile Thr Asp Leu Val Leu Phe Phe Leu Asp Thr Tyr Leu Trp Tyr
        755                 760                 765

Ile Ile Trp Asn Thr Ile Cys Ser Val Ala Arg Ser Phe Tyr Leu Gly
    770                 775                 780

Val Ser Ile Trp Thr Pro Trp Arg Asn Ile Phe Ser Arg Met Pro Lys
785                 790                 795                 800

Arg Ile Tyr Ser Lys Ile Leu Ala Thr Asn Asp Met Glu Ile Lys Tyr
                805                 810                 815

Lys Pro Lys Val Leu Ile Ser Gln Val Trp Asn Ala Val Val Ile Ser
            820                 825                 830

Met Tyr Arg Glu His Leu Leu Ala Ile Asp His Val Gln Lys Leu Leu
        835                 840                 845

Tyr His Gln Val Pro Ser Glu Gln Glu Gly Lys Arg Thr Leu Arg Ala
    850                 855                 860

Pro Thr Phe Phe Ile Ser Gln Glu Asp His Ser Phe Lys Thr Glu Phe
865                 870                 875                 880

Phe Pro Ser His Ser Glu Ala Glu Arg Arg Ile Ser Phe Phe Ala Gln
                885                 890                 895

Ser Leu Ser Thr Pro Ile Pro Glu Pro Leu Pro Val Asp Asn Met Pro
            900                 905                 910

Thr Phe Thr Val Leu Val Pro His Tyr Gly Glu Lys Ile Leu Tyr Ser
        915                 920                 925

Leu Arg Glu Ile Ile Arg Glu Asp Asp Gln Leu Ser Arg Val Thr Leu
    930                 935                 940

Leu Glu Tyr Leu Lys Gln Leu His Pro Val Glu Trp Asp Cys Phe Val
945                 950                 955                 960

Lys Asp Thr Lys Ile Leu Ala Glu Glu Thr Ser Leu Tyr Asn Gly Gly
                965                 970                 975

Val Pro Phe Asp Lys Asp Glu Lys Asp Thr Val Lys Ser Lys Ile Asp
            980                 985                 990

Asp Leu Pro Phe Tyr Cys Val Gly  Phe Lys Ser Ser Ala  Pro Glu Tyr
        995                 1000                 1005

Thr Leu  Arg Thr Arg Ile Trp  Ala Ser Leu Arg Ser  Gln Thr Leu
    1010                 1015                 1020

Tyr Arg  Thr Val Ser Gly Phe  Met Asn Tyr Ser Arg  Ala Ile Lys
    1025                 1030                 1035

Leu Leu  Tyr Arg Val Glu Asn  Pro Asp Val Val Gln  Met Phe Gly
    1040                 1045                 1050

Gly Asn  Thr Asp Lys Leu Glu  His Glu Leu Glu Arg  Met Ala Arg
    1055                 1060                 1065

Arg Lys  Phe Lys Phe Asp Ile  Ser Met Gln Arg Phe  Phe Lys Phe
    1070                 1075                 1080

Ser Lys  Glu Glu Leu Glu Asn  Thr Glu Phe Leu Leu  Arg Ala Tyr
    1085                 1090                 1095

Pro Asp  Leu Gln Ile Ala Tyr  Leu Asp Glu Glu Pro  Pro Met Asn
    1100                 1105                 1110

Glu Gly  Asp Glu Pro Lys Ile  Tyr Ser Ser Leu Ile  Asp Gly Tyr
    1115                 1120                 1125

Ser Glu  Ile Met Glu Asn Gly  Lys Arg Arg Pro Lys  Phe Arg Ile
```

```
    1130                1135                1140

Gln Leu  Ser Gly Asn Pro Ile  Leu Gly Asp Gly Lys  Ser Asp Asn
    1145                1150                1155

Gln Asn  His Ala Ile Ile Phe  Tyr Arg Gly Glu Tyr  Ile Gln Leu
    1160                1165                1170

Ile Asp  Ala Asn Gln Asp Asn  Tyr Leu Glu Glu Cys  Leu Lys Ile
    1175                1180                1185

Arg Ser  Val Leu Ala Glu Phe  Glu Glu Met Thr Pro  Thr Glu Glu
    1190                1195                1200

Ser Pro  Tyr Asn Pro Asn Glu  Ile Ser Ser Ala Thr  Asn Pro Val
    1205                1210                1215

Ala Ile  Leu Gly Ala Arg Glu  Tyr Ile Phe Ser Glu  Asn Ile Gly
    1220                1225                1230

Val Leu  Gly Asp Val Ala Ala  Gly Lys Glu Gln Thr  Phe Gly Thr
    1235                1240                1245

Leu Phe  Ala Arg Thr Leu Ala  Gln Ile Gly Gly Lys  Leu His Tyr
    1250                1255                1260

Gly His  Pro Asp Phe Leu Asn  Gly Pro Phe Met Thr  Thr Arg Gly
    1265                1270                1275

Gly Val  Ser Lys Ala Gln Lys  Gly Leu His Leu Asn  Glu Asp Ile
    1280                1285                1290

Tyr Ala  Gly Met Thr Ala Leu  Leu Arg Gly Gly Arg  Ile Lys His
    1295                1300                1305

Cys Glu  Tyr Tyr Gln Cys Gly  Lys Gly Arg Asp Leu  Gly Phe Gly
    1310                1315                1320

Ser Ile  Leu Asn Phe Thr Thr  Lys Val Gly Thr Gly  Met Gly Glu
    1325                1330                1335

Gln Met  Leu Ser Arg Glu Tyr  Tyr Tyr Leu Gly Thr  Gln Leu Pro
    1340                1345                1350

Leu Asp  Arg Phe Leu Ser Phe  Tyr Tyr Ala His Pro  Gly Phe His
    1355                1360                1365

Ile Asn  Asn Leu Phe Ile Ile  Leu Ser Val Gln Leu  Leu Met Ile
    1370                1375                1380

Val Met  Ile Asn Leu Gly Ser  Met Tyr Asn Ile Leu  Leu Ile Cys
    1385                1390                1395

Arg Pro  Arg Arg Gly Gln Pro  Ile Thr Asp Pro Tyr  Leu Pro Val
    1400                1405                1410

Gly Cys  Tyr Ser Leu Ala Pro  Val Leu Asp Trp Ile  Lys Arg Ser
    1415                1420                1425

Ile Ile  Ser Ile Phe Ile Asp  Phe Phe Ile Ala Phe  Ile Pro Leu
    1430                1435                1440

Val Val  Gln Glu Leu Thr Glu  Arg Gly Val Trp Arg  Ala Ser Thr
    1445                1450                1455

Arg Leu  Ala Lys His Phe Gly  Ser Leu Ser Pro Leu  Phe Glu Val
    1460                1465                1470

Phe Val  Ser Gln Ile Tyr Ala  Asn Ser Leu Leu Gln  Asn Leu Ala
    1475                1480                1485

Phe Gly  Gly Ala Arg Tyr Ile  Gly Thr Gly Arg Gly  Phe Ala Thr
    1490                1495                1500

Thr Arg  Ile Pro Phe Ser Ile  Pro Phe Ser Arg Phe  Ala Gly Ala
    1505                1510                1515

Ser Ile  Tyr Leu Gly Ser Arg  Thr Leu Ile Met Leu  Leu Phe Ala
    1520                1525                1530
```

-continued

```
Thr Val  Thr Met Trp Ile Pro  His Leu Val Tyr Phe  Trp Val Ser
    1535                 1540                 1545

Val Leu  Ala Leu Cys Ile Ser  Pro Phe Ile Phe Asn  Pro His Gln
    1550                 1555                 1560

Phe Ser  Trp Thr Asp Phe Phe  Val Asp Tyr Arg Glu  Phe Ile Arg
    1565                 1570                 1575

Trp Leu  Ser Arg Gly Asn Ser  Arg Ser His Ala Asn  Ser Trp Ile
    1580                 1585                 1590

Gly Tyr  Cys Arg Leu Ser Arg  Thr Arg Ile Thr Gly  Phe Lys Arg
    1595                 1600                 1605

Lys Ala  Leu Gly Gln Pro Ser  Glu Lys Leu Ser Gly  Asp Ile Pro
    1610                 1615                 1620

Arg Ala  Gly Phe Ser Asn Val  Phe Phe Ser Glu Val  Ile Gly Pro
    1625                 1630                 1635

Met Ile  Leu Val Leu Leu Ser  Leu Val Pro Tyr Cys  Phe Ile Asn
    1640                 1645                 1650

Ser Arg  Pro Gly Phe Glu Pro  Phe Gly Lys Ser Asn  Pro Ala Lys
    1655                 1660                 1665

Asn Gly  Ser Asn Pro Leu Ile  Arg Ile Ala Ile Val  Ser Phe Ala
    1670                 1675                 1680

Pro Ile  Cys Val Asn Ala Met  Val Ala Phe Val Phe  Phe Gly Met
    1685                 1690                 1695

Ala Cys  Cys Met Gly Pro Ile  Leu Thr Ile Cys Cys  Lys Lys Phe
    1700                 1705                 1710

Gly Ala  Val Leu Ala Thr Ile  Ser His Ala Ile Ala  Val Ile Ile
    1715                 1720                 1725

Leu Val  Thr Phe Phe Glu Val  Leu Trp Phe Leu Glu  Gly Trp Ser
    1730                 1735                 1740

Phe Ser  Lys Thr Ile Leu Gly  Leu Val Thr Met Ile  Ser Leu Gln
    1745                 1750                 1755

Arg Ala  Phe Leu Lys Ile Leu  Thr Ile Met Ile Leu  Thr Arg Glu
    1760                 1765                 1770

Phe Lys  His Asp Gly Ser Asn  Leu Ala Trp Trp Thr  Gly Arg Trp
    1775                 1780                 1785

Tyr Ser  Asn Asn Leu Gly Val  Tyr Ala Met Ser Gln  Pro Ala Arg
    1790                 1795                 1800

Glu Phe  Val Cys Lys Val Ile  Glu Leu Ser Leu Phe  Ala Ala Asp
    1805                 1810                 1815

Phe Cys  Leu Gly His Leu Leu  Leu Phe Ile Leu Thr  Pro Ile Leu
    1820                 1825                 1830

Ala Ile  Pro Tyr Ile Asp Arg  Trp His Ser Met Leu  Leu Phe Trp
    1835                 1840                 1845

Leu Arg  Pro Ser Arg Gln Ile  Arg Pro Pro Ile Phe  Ser Leu Lys
    1850                 1855                 1860

Gln Asn  Lys Leu Arg Lys Arg  Ile Val Arg Arg Tyr  Ala Thr Leu
    1865                 1870                 1875

Phe Phe  Gly Leu Phe Leu Leu  Phe Leu Met Ile Ile  Leu Val Pro
    1880                 1885                 1890

Ala Leu  Gly His Ser Lys Phe  Pro Lys Ser Leu Asn  Asn Ile Ala
    1895                 1900                 1905

Phe Leu  Lys Asn Leu Gly Leu  Ile Gln Pro Ser Asn  Asp Pro Arg
    1910                 1915                 1920
```

-continued

```
Gly Ala  Thr Gly Arg Thr Thr  Arg Pro Gly Asn Ser  Asn Gly Thr
    1925                1930                1935

Tyr Lys  Leu Phe Ile Tyr
    1940


<210> SEQ ID NO 3
<211> LENGTH: 416
<212> TYPE: PRT
<213> ORGANISM: Schizosaccharomyces pombe

<400> SEQUENCE: 3

Met Arg Leu Ser Ser Arg Phe Tyr Leu Phe Thr Ser Phe Thr Ala Trp
1               5                   10                  15

Ser Val Val Ile Ala Gly Ala Thr Pro Ala Val Cys Gly Ala Pro Glu
            20                  25                  30

Tyr Ile Ile Glu Thr Gln Asn Asp Leu Asp Val Leu Ser Asn Cys Gln
        35                  40                  45

Val Val Asn Gly Ser Ile Ile Met Asn Thr Ser Ser Ala Thr Ser Leu
    50                  55                  60

Asn Phe Asn Arg Ile Glu Thr Ile Thr Gly Asp Leu Ile Ile Arg Asn
65                  70                  75                  80

Asn Asn Tyr Leu Ala Ser Val Ala Leu Thr Ser Ile Ser Ser Val Gly
                85                  90                  95

Gly Glu Leu Arg Phe Glu Lys Leu Thr Arg Leu Ala Ser Val Tyr Ala
            100                 105                 110

Pro Gln Leu Ala Asn Val Gly Gln Leu Thr Met Arg Ile Leu Pro Asn
        115                 120                 125

Leu Gln Gly Ile Arg Phe Asp Lys Gly Ile Lys Lys Ala His Lys Leu
    130                 135                 140

Thr Ile Glu Asp Thr Gln Leu Ser Thr Leu Ala Gly Ile Ser Leu Asn
145                 150                 155                 160

Thr Thr Asp Thr Met Val Ile Val Asn Asn Asn Tyr Leu Arg Glu Val
                165                 170                 175

Asp Met Pro Tyr Leu Glu Ser Val Glu Ser Lys Phe Tyr Val Ser Tyr
            180                 185                 190

Asn Ala Arg Glu Ile Ser Val Thr Leu Pro Arg Leu Lys Thr Val Gly
        195                 200                 205

Asp Met Thr Ile Gln Arg Val Ala His Leu Gln Leu Ser Asn Leu Glu
    210                 215                 220

Glu Val Lys Gly Phe Leu Gly Phe Leu Asn Ser Thr Leu Gln Asp Ile
225                 230                 235                 240

Ser Cys Pro Asn Ile Thr Arg Ile Gly Gln Ser Leu Phe Phe Ile Gly
                245                 250                 255

Asn Gln Glu Leu Thr Ser Leu Asn Phe Lys Gln Leu Glu Ser Ile Gly
            260                 265                 270

Gly Thr Phe Met Ile Ala Asn Ser Ala Ala Leu Ala Gln Ile Lys Gly
        275                 280                 285

Tyr Asp Lys Leu Lys Thr Val Ala Gly Ser Ile Asp Phe Thr Gly Asn
    290                 295                 300

Phe Ser Ser Val Glu Leu Pro Lys Leu Arg Asp Val Lys Gly Gly Leu
305                 310                 315                 320

Asn Ile Gln Thr Thr Ser Ser Asp Phe Thr Cys Pro Phe Arg Gln Ser
                325                 330                 335

Asp Gly Ile Ile Lys Gly Lys Ser Phe Val Cys Arg Gly Ser Val Asp
            340                 345                 350
```

```
Asn Pro Arg Gln Ser Lys Glu Ser Ser Phe Asp Asp Asp Asp Phe Asp
        355                 360                 365

Glu Leu Leu Gly Asn Gly Thr Ile Lys Gly Ser Lys Asn Ser Thr Ser
    370                 375                 380

Pro Val Lys Gln Ser Gly Ala Ala Lys Val Asp Ser Arg Pro Phe Arg
385                 390                 395                 400

Leu Val Thr Phe Phe Leu Val Leu Val Ser Gly Phe Ala His Leu Leu
                405                 410                 415


<210> SEQ ID NO 4
<211> LENGTH: 378
<212> TYPE: PRT
<213> ORGANISM: Schizosaccharomyces pombe

<400> SEQUENCE: 4

Met Ser Ser Thr Ala Leu Leu Pro Pro Asn Thr Asp Gln Val Leu Ser
1               5                   10                  15

Arg Arg Leu His Gly Lys Ala Ala Glu Lys Lys Thr Gly Leu Ala Ala
            20                  25                  30

Ile Ala Ser Lys Asp Val Asp Glu Gln Ser Arg Lys Leu Gln Glu Tyr
        35                  40                  45

Phe Glu Phe Trp Asp Arg Asn His Glu Asn Glu Ser Glu Glu Asp Arg
    50                  55                  60

Ala Arg Arg Ile Asp Gly Tyr Lys Ser Val Val Asn Ser Tyr Tyr Asp
65                  70                  75                  80

Leu Ala Thr Asp Leu Tyr Glu Tyr Gly Trp Ser Gln Ser Phe His Phe
                85                  90                  95

Ser Arg Phe Tyr Lys Gly Glu Ala Phe Ala Gln Ser Ile Ala Arg His
            100                 105                 110

Glu His Tyr Leu Ala Tyr Arg Met Gly Ile Lys Pro Gly Ser Arg Val
        115                 120                 125

Leu Asp Val Gly Cys Gly Val Gly Gly Pro Ala Arg Glu Ile Thr Glu
    130                 135                 140

Phe Thr Gly Cys Asn Leu Val Gly Leu Asn Asn Asn Asp Tyr Gln Ile
145                 150                 155                 160

Ser Arg Cys Asn Asn Tyr Ala Val Lys Arg Asn Leu Asp Lys Lys Gln
                165                 170                 175

Val Phe Val Lys Gly Asp Phe Met His Met Pro Phe Glu Asp Asn Thr
            180                 185                 190

Phe Asp Tyr Val Tyr Ala Ile Glu Ala Thr Val His Ala Pro Ser Leu
        195                 200                 205

Glu Gly Val Tyr Gly Glu Ile Phe Arg Val Leu Lys Pro Gly Gly Val
    210                 215                 220

Phe Gly Val Tyr Glu Trp Val Met Ser Asp Asp Tyr Asp Ser Ser Ile
225                 230                 235                 240

Pro Lys His Arg Glu Ile Ala Tyr Asn Ile Glu Val Gly Asp Gly Ile
                245                 250                 255

Pro Gln Met Val Arg Lys Cys Asp Ala Val Glu Ala Ile Lys Lys Val
            260                 265                 270

Gly Phe Asn Leu Leu Glu Glu Asp Asp Leu Thr Asp His Asp Asn Pro
        275                 280                 285

Asp Leu Pro Trp Tyr Tyr Pro Leu Thr Gly Asp Ile Thr Lys Cys Gln
    290                 295                 300

Asn Ile Trp Asp Val Phe Thr Val Phe Arg Thr Ser Arg Leu Gly Lys
```

-continued

```
305                 310                 315                 320

Leu Val Thr Arg Tyr Ser Val Gln Phe Leu Glu Lys Ile Gly Val Ala
                325                 330                 335

Ala Lys Gly Thr Ser Lys Val Gly Asp Thr Leu Ala Ile Ala Gln Lys
            340                 345                 350

Gly Leu Ile Glu Gly Gly Glu Thr His Leu Phe Thr Pro Met Phe Leu
        355                 360                 365

Met Ile Ala Lys Lys Pro Glu Thr Asp Ala
    370                 375


<210> SEQ ID NO 5
<211> LENGTH: 525
<212> TYPE: PRT
<213> ORGANISM: Schizosaccharomyces pombe

<400> SEQUENCE: 5

Met Leu Lys Lys Gln Ala Leu Ser Gly Ile Arg Arg Phe Ser Leu Ala
1               5                   10                  15

Thr Lys Gln Ser Phe Val Lys Thr Ser Tyr Lys Leu Pro Arg Lys Ser
            20                  25                  30

Trp Leu Asn Thr Ala Lys Phe Asn Thr Ile Arg Tyr Ala Ser Thr Glu
        35                  40                  45

Ala Ala Lys His Asn Lys Gly Ser Ile Lys Gln Val Ile Gly Ala Val
    50                  55                  60

Val Asp Cys Gln Phe Glu Asp Ala Asp Ser Leu Pro Ser Ile Leu Asn
65                  70                  75                  80

Ala Leu Glu Val Lys Leu Pro Asp Asn Lys Arg Leu Val Leu Glu Val
                85                  90                  95

Ala Gln His Val Gly Glu Asn Thr Val Arg Thr Ile Ala Met Asp Gly
            100                 105                 110

Thr Glu Gly Leu Val Arg Gly Thr Ala Val Ile Asp Thr Gly Ser Pro
        115                 120                 125

Ile Ser Ile Pro Val Gly Pro Gly Thr Leu Gly Arg Ile Met Asn Val
    130                 135                 140

Ile Gly Glu Pro Val Asp Glu Arg Gly Pro Ile Lys Ala Val Lys Tyr
145                 150                 155                 160

Ser Pro Ile His Ala Asp Ala Pro Ser Phe Glu Glu Gln Ser Thr Thr
                165                 170                 175

Pro Glu Ile Leu Glu Thr Gly Ile Lys Val Val Asp Leu Leu Ala Pro
            180                 185                 190

Tyr Ala Arg Gly Gly Lys Ile Gly Leu Phe Gly Gly Ala Gly Val Gly
        195                 200                 205

Lys Thr Val Phe Ile Gln Glu Leu Ile Asn Asn Ile Ala Lys Ala His
    210                 215                 220

Gly Gly Tyr Ser Val Phe Thr Gly Val Gly Glu Arg Thr Arg Glu Gly
225                 230                 235                 240

Asn Asp Leu Tyr Arg Glu Met Gln Glu Thr Gly Val Ile Lys Leu Glu
                245                 250                 255

Gly Glu Ser Lys Ala Ala Leu Val Phe Gly Gln Met Asn Glu Pro Pro
            260                 265                 270

Gly Ala Arg Ala Arg Val Ala Leu Thr Gly Leu Thr Val Ala Glu Tyr
        275                 280                 285

Phe Arg Asp Ile Glu Gly Gln Asp Val Leu Leu Phe Ile Asp Asn Ile
    290                 295                 300
```

-continued

```
Phe Arg Phe Thr Gln Ala Gly Ser Glu Val Ser Ala Leu Leu Gly Arg
305                 310                 315                 320

Ile Pro Ser Ala Val Gly Tyr Gln Pro Thr Leu Ala Thr Asp Met Gly
                325                 330                 335

Ala Met Gln Glu Arg Ile Thr Thr Thr Lys Lys Gly Ser Ile Thr Ser
            340                 345                 350

Val Gln Ala Val Tyr Val Pro Ala Asp Asp Leu Thr Asp Pro Ala Pro
        355                 360                 365

Ala Thr Thr Phe Ala His Leu Asp Ala Thr Thr Val Leu Ser Arg Ser
    370                 375                 380

Ile Ser Glu Leu Gly Ile Tyr Pro Ala Val Asp Pro Leu Asp Ser Lys
385                 390                 395                 400

Ser Arg Met Met Asp Pro Arg Ile Leu Gly Glu Glu His Tyr Asn Leu
                405                 410                 415

Ala Gly Ser Val Gln Gln Met Leu Gln Glu Tyr Lys Ser Leu Gln Asp
            420                 425                 430

Ile Ile Ala Ile Leu Gly Met Asp Glu Leu Ser Glu Ala Asp Lys Leu
        435                 440                 445

Thr Val Glu Arg Ala Arg Lys Val Gln Arg Phe Leu Ser Gln Pro Phe
    450                 455                 460

Ala Val Ala Glu Val Phe Thr Gly Ile Glu Gly Arg Leu Val Ser Leu
465                 470                 475                 480

Lys Asp Thr Ile Arg Ser Phe Lys Glu Ile Leu Glu Gly Lys His Asp
                485                 490                 495

Ser Leu Pro Glu Ser Ala Phe Tyr Met Val Gly Ser Ile Asp Asp Ala
            500                 505                 510

Val Lys Lys Ala Glu Lys Ile Ala Gln Glu Leu Ala Ala
        515                 520                 525


<210> SEQ ID NO 6
<211> LENGTH: 471
<212> TYPE: PRT
<213> ORGANISM: Saccharomyces cerevisiae

<400> SEQUENCE: 6

Met Met Val Phe Ser Ser Thr Phe Ile Phe Leu Ile Leu Glu Leu Val
1               5                   10                  15

Val Leu Cys Glu Ala Ser Val His Thr Ile Gln Ile Lys Asp Lys His
            20                  25                  30

Phe Val Asp Thr Val Thr Gly Lys Pro Phe Phe Ile Lys Gly Val Asp
        35                  40                  45

Tyr Gln Pro Gly Gly Ser Ser Asp Val Ser Glu Lys Gln Asp Pro Leu
    50                  55                  60

Ser Asn Pro Asp Ala Cys Ala Arg Asp Ile Leu Leu Phe Gln Glu Leu
65                  70                  75                  80

Gly Ile Asn Thr Val Arg Ile Tyr Ser Ile Asn Pro Asp Leu Asn His
                85                  90                  95

Asp Ala Cys Met Thr Met Leu Ala Met Ala Gly Ile Tyr Leu Ile Leu
            100                 105                 110

Asp Val Asn Ser Pro Leu Gln Asn Gln His Leu Asn Arg Tyr Glu Pro
        115                 120                 125

Trp Thr Thr Tyr Asn Glu Val Tyr Leu Glu His Val Phe Lys Val Val
    130                 135                 140

Glu Gln Phe Ser His Tyr Asn Asn Thr Leu Gly Phe Phe Ala Gly Asn
145                 150                 155                 160
```

```
Glu Ile Val Asn Asp Lys Arg Ser Ala Gln Tyr Ser Pro Ala Tyr Val
                165                 170                 175

Lys Glu Leu Ile Gly Thr Met Lys Asn Tyr Ile Ser Ala His Ser Pro
            180                 185                 190

Arg Thr Ile Pro Val Gly Tyr Ser Ala Ala Asp Asp Leu Asn Tyr Arg
        195                 200                 205

Val Ser Leu Ser Glu Tyr Leu Glu Cys Lys Asp Asp Asp Lys Pro Glu
    210                 215                 220

Asn Ser Val Asp Phe Tyr Gly Val Asn Ser Tyr Gln Trp Cys Gly Gln
225                 230                 235                 240

Gln Thr Met Gln Thr Ser Gly Tyr Asp Thr Leu Val Asp Ala Tyr Arg
                245                 250                 255

Ser Tyr Ser Lys Pro Val Phe Phe Ser Glu Phe Gly Cys Asn Lys Val
            260                 265                 270

Leu Pro Arg Gln Phe Gln Glu Ile Gly Tyr Leu Phe Ser Glu Glu Met
        275                 280                 285

Tyr Ser Val Phe Cys Gly Gly Leu Val Tyr Glu Phe Ser Gln Glu Asp
    290                 295                 300

Asn Asn Tyr Gly Leu Val Glu Tyr Gln Glu Asp Asp Ser Val Gln Leu
305                 310                 315                 320

Leu Ala Asp Phe Glu Lys Leu Lys Ser His Tyr Gln Asn Ile Glu Phe
                325                 330                 335

Pro Ser Met Lys Thr Leu Lys Glu Thr Val Gln Met Glu Glu Thr Pro
            340                 345                 350

Ser Cys Ala Glu Asp Tyr Glu Asn Leu Lys Ile Glu Ser Lys Ile Ala
        355                 360                 365

Lys Asn Leu Gly Ser Ser Leu Ile Lys Lys Gly Val Lys Val Glu Lys
    370                 375                 380

Gly Lys Tyr Ile Asp Ile His Glu Asp Gln Leu Ser Thr Asn Val Thr
385                 390                 395                 400

Ile Leu Asp Lys His Gly Asp Arg Trp Asn Gly Pro Lys Lys Ile Glu
                405                 410                 415

Ile Arg Gln Ser Leu Thr Leu Ala Asp Leu Glu Gly Glu Glu Gln Glu
            420                 425                 430

Asp Ala Asp Glu Asp Lys Asp Asp Leu Lys Arg Lys His Arg Asn Ser
        435                 440                 445

Ala Ser Ile Ser Gly Pro Leu Leu Pro Leu Gly Leu Cys Leu Leu Phe
    450                 455                 460

Phe Thr Phe Ser Leu Phe Phe
465                 470


<210> SEQ ID NO 7
<211> LENGTH: 456
<212> TYPE: PRT
<213> ORGANISM: Schizosaccharomyces pombe

<400> SEQUENCE: 7

Met Gly Val Ala Asn Ile Ile Tyr Ala Leu Phe Leu Leu Gly Pro Ser
1               5                   10                  15

Ile Phe Leu Lys Ala Thr Ala Gln Thr His Pro Ile Val Ile Lys Gly
            20                  25                  30

Asn Ala Phe Phe Asp Ser Lys Thr Asn Glu Arg Phe Tyr Ile Arg Gly
        35                  40                  45

Val Asp Tyr Gln Pro Gly Gly Ser Ser Ser Leu Val Asp Pro Leu Ala
```

```
    50                  55                  60

Ser Arg Ser Cys Lys Lys Asp Val Glu Ile Phe Lys Lys Leu Gly Ile
65                  70                  75                  80

Asn Thr Val Arg Val Tyr Gln Val Asp Asn Ser Ala Asp His Asp Lys
                85                  90                  95

Cys Met Asn Ala Leu Ser Glu Ala Gly Ile Tyr Val Ile Leu Asp Leu
            100                 105                 110

Asn Thr Tyr Arg His Ser Ile Ser Arg Ala His Pro Ala Leu Ser Tyr
        115                 120                 125

Asn Lys Val Tyr Leu Gln His Leu Phe Ala Thr Ile Asp Ala Phe Lys
    130                 135                 140

Gly Tyr Asp Asn Val Leu Gly Phe Phe Ser Gly Asn Glu Val Val Asn
145                 150                 155                 160

Asp Glu Asp Thr Thr Ala Ile Thr Trp Val Lys Ala Val Thr Arg Asp
                165                 170                 175

Val Lys Ala Tyr Ile Lys Lys His Ser Asp Arg His Ile Pro Val Gly
            180                 185                 190

Tyr Ser Ala Ala Asp Val Ala Glu Asn Arg Leu Gln Leu Ala His Tyr
        195                 200                 205

Phe Asn Cys Gly Asp Glu Ser Glu Arg Ala Asp Phe Tyr Ala Phe Asn
    210                 215                 220

Met Tyr Glu Trp Cys Gly Tyr Ser Ser Met Thr Val Ser Gly Tyr Tyr
225                 230                 235                 240

Asp Arg Ile Lys Glu Phe Ser Asn Tyr Ser Ile Pro Leu Phe Leu Ser
                245                 250                 255

Glu Phe Gly Cys Asn Thr Val Glu Ile Asn Asp Asp Thr Thr Pro Asn
            260                 265                 270

Arg Pro Phe Thr Glu Ile Glu Ala Ile Tyr Ser His Asp Met Thr Pro
        275                 280                 285

Val Phe Ser Gly Gly Leu Val Tyr Glu Tyr Ser Ala Glu Pro Asn His
    290                 295                 300

Tyr Gly Leu Val Val Ile Asp Lys Asp Asp Glu Arg Arg Val Ser Arg
305                 310                 315                 320

Asn Phe Ile Thr Leu Met Lys Gln Tyr Ala Lys Thr Pro Asn Pro Lys
                325                 330                 335

Gly Asp Gly Gly Tyr Lys Lys Ala Gly Ser Pro Ser Lys Cys Pro Ala
            340                 345                 350

Asn Ser Thr Gln Phe Asn Ala Trp Glu Lys Leu Pro Glu Met Pro Glu
        355                 360                 365

Gly Ala Lys Ile Tyr Met Glu Lys Gly Ala Gly Glu Pro Leu Gly Ile
    370                 375                 380

Glu Gly Pro Thr Asn Met Trp Ser Pro Phe His Asp Gly Asp Asp Asp
385                 390                 395                 400

Glu Ser Thr Ser Arg Arg Pro Lys Pro Lys Asn Lys Pro Ser Asn Val
                405                 410                 415

Thr Ser Thr Thr Ser Tyr Thr Ser Gly Met Thr Ser Ser Ser Glu Ser
            420                 425                 430

Gly Ser Ser Lys Ile Gly Val Ala Phe Cys Gln Ala Leu Phe Ile Thr
        435                 440                 445

Val Leu Ile Ala Thr Leu Ser Phe
    450                 455
```

<210> SEQ ID NO 8

-continued

<211> LENGTH: 531
<212> TYPE: PRT
<213> ORGANISM: Schizosaccharomyces pombe

<400> SEQUENCE: 8

```
Met Val Asp Gln Val Asn Leu Ala Thr Glu Gln Thr Ser Leu Leu Tyr
1               5                   10                  15

Pro Glu Val Ser Arg Lys Lys Glu Glu Leu Ser Val Asn Lys Trp Thr
            20                  25                  30

Ile Leu Pro Ala Leu Trp Val Gly Gly Phe Leu Ser Ala Leu Asp Met
        35                  40                  45

Thr Ile Val Ala Ser Leu Tyr Pro Val Ile Gly Ser Glu Phe Lys Leu
    50                  55                  60

Met Asn Asn Ala Ser Tyr Ile Val Thr Ala Tyr Leu Ile Thr Asn Thr
65                  70                  75                  80

Ala Phe Gln Pro Leu Tyr Gly Arg Leu Ser Asp Ile Phe Gly Arg Arg
                85                  90                  95

Pro Thr Val Val Phe Ala Asn Ala Ala Phe Thr Leu Gly Thr Phe Trp
            100                 105                 110

Cys Gly Ile Ser Arg Ser Leu Pro Glu Leu Cys Met Ala Arg Ala Leu
        115                 120                 125

Ala Gly Ile Gly Gly Gly Gly Leu Gly Thr Met Ser Ser Ile Ile Ser
    130                 135                 140

Ser Asp Ile Val Ser Leu Arg Glu Arg Gly Thr Trp Gln Gly Ile Thr
145                 150                 155                 160

Asn Ile Val Trp Gly Ile Gly Gly Ser Leu Gly Gly Pro Leu Gly Gly
                165                 170                 175

Leu Ile Ala Gln Arg Trp Gly Trp Arg Thr Ala Phe His Phe Gln Val
            180                 185                 190

Pro Met Gly Ile Leu Ser Thr Ile Leu Val Ala Trp Arg Val Arg Val
        195                 200                 205

Lys Pro Thr Val Arg Asn Ser Asn Ala Ser Leu Leu Ser Arg Ile Asp
    210                 215                 220

Tyr Leu Gly Ser Phe Leu Leu Val Thr Gly Ile Thr Ala Leu Val Val
225                 230                 235                 240

Thr Phe Asn Met Gly Gly Asp Ala Phe Pro Trp Val Ser Pro Val Ile
                245                 250                 255

Ile Thr Leu Leu Val Ser Ser Val Leu Ile Leu Phe Ala Phe Tyr Trp
            260                 265                 270

Val Glu Lys Asn Ile Ala Val Glu Pro Ile Ala Pro Val Glu Ile Leu
        275                 280                 285

Ser Gln Pro Thr Pro Leu Asn Val Cys Leu Gly Asn Phe Phe Asn Ala
    290                 295                 300

Phe Cys Ser Phe Val Ile Val Tyr Glu Leu Pro Leu Phe Phe Glu Thr
305                 310                 315                 320

Thr Leu Leu Met Pro Ser Ser Glu Ala Gly Val Arg Ile Phe Pro Tyr
                325                 330                 335

Val Ile Ser Thr Ser Val Gly Ser Leu Cys Ser Gly Leu Tyr Met Lys
            340                 345                 350

Lys Thr Gly Arg Tyr Arg Asn Leu Val Ile Ala Gly Phe Phe Phe Met
        355                 360                 365

Leu Met Gly Ile Val Ser Phe Ala Val Leu Thr Ser Phe Gly His Arg
    370                 375                 380

Thr Pro Leu Ile Leu Ile Ser Leu Cys Leu Ala Met Thr Gly Cys Ser
```

-continued

```
385                 390                 395                 400

Tyr Gly Met Asn Leu Thr Ser Thr Leu Ile Ala Ile Ile Ser Ser Leu
                405                 410                 415

Ala Pro Glu Glu Gln Ala Val Ala Thr Gly Leu Ser Tyr Leu Phe Arg
            420                 425                 430

Ala Thr Gly Ser Val Ile Gly Ile Ser Leu Ser Gln Thr Thr Thr Leu
        435                 440                 445

Ser Ile Leu Met Lys Gln Leu Ala Ser Asn Leu Lys Asp Asp Pro Asp
    450                 455                 460

Lys Asp Asp Leu Ile Arg Arg Leu Arg Glu Ser Ile Ser Ile Ile Pro
465                 470                 475                 480

Asn Leu Pro Lys Asp Ile Gln Lys Leu Val Ile Lys Ser Tyr Ala Thr
                485                 490                 495

Ala Phe Thr Trp Thr Phe Ala Leu Val Ala Ile Ile Ala Phe Ala Gly
            500                 505                 510

Phe Trp Cys Ser Leu Arg Ile Lys Gln Phe Tyr Leu His Thr Ser Val
        515                 520                 525

Asp Arg Ser
    530


<210> SEQ ID NO 9
<211> LENGTH: 15
<212> TYPE: PRT
<213> ORGANISM: Schizosaccharomyces pombe

<400> SEQUENCE: 9

Ile Val Gly Glu Ser Tyr Pro Ile Arg Tyr Arg Ser Lys Cys Ala
1               5                   10                  15


<210> SEQ ID NO 10
<211> LENGTH: 15
<212> TYPE: PRT
<213> ORGANISM: Schizosaccharomyces pombe

<400> SEQUENCE: 10

Tyr Ala Ala Val Gly Asn Arg Ala Leu Thr Arg Lys Asn Gly Thr
1               5                   10                  15


<210> SEQ ID NO 11
<211> LENGTH: 15
<212> TYPE: PRT
<213> ORGANISM: Schizosaccharomyces pombe

<400> SEQUENCE: 11

Leu Pro Glu Ser Pro Arg Tyr Leu Ile Ser Val Gly Arg Asp Glu
1               5                   10                  15


<210> SEQ ID NO 12
<211> LENGTH: 15
<212> TYPE: PRT
<213> ORGANISM: Schizosaccharomyces pombe

<400> SEQUENCE: 12

Val Thr Ala Val Pro Ser Trp Val Gln Ile Met Val Ala Lys Ile
1               5                   10                  15


<210> SEQ ID NO 13
<211> LENGTH: 15
<212> TYPE: PRT
<213> ORGANISM: Schizosaccharomyces pombe
```

<400> SEQUENCE: 13

Pro Ser Trp Val Gln Ile Met Val Ala Lys Ile Trp Thr Gly Leu
1 5 10 15

<210> SEQ ID NO 14
<211> LENGTH: 15
<212> TYPE: PRT
<213> ORGANISM: Schizosaccharomyces pombe

<400> SEQUENCE: 14

Glu Gly Thr Gly Met Asn Ser Pro Tyr Leu Ser Ala Leu Ile Leu
1 5 10 15

<210> SEQ ID NO 15
<211> LENGTH: 15
<212> TYPE: PRT
<213> ORGANISM: Schizosaccharomyces pombe

<400> SEQUENCE: 15

Trp Thr Ile Val Tyr Leu Ile Gly Ile Ile Leu Gln Val Thr Ala
1 5 10 15

<210> SEQ ID NO 16
<211> LENGTH: 15
<212> TYPE: PRT
<213> ORGANISM: Schizosaccharomyces pombe

<400> SEQUENCE: 16

Leu Glu Phe Phe Gly Arg Arg Met Pro Leu Ile Ile Gly Ala Leu
1 5 10 15

<210> SEQ ID NO 17
<211> LENGTH: 15
<212> TYPE: PRT
<213> ORGANISM: Schizosaccharomyces pombe

<400> SEQUENCE: 17

Lys Ile Trp Thr Gly Leu Ser Ile Gly Ala Leu Ser Val Leu Ala
1 5 10 15

<210> SEQ ID NO 18
<211> LENGTH: 15
<212> TYPE: PRT
<213> ORGANISM: Schizosaccharomyces pombe

<400> SEQUENCE: 18

Gly Thr Ser Asn His Arg Ala Gly Ala Val Met Ile Val Phe Ser
1 5 10 15

<210> SEQ ID NO 19
<211> LENGTH: 15
<212> TYPE: PRT
<213> ORGANISM: Pneumocystis carinii

<400> SEQUENCE: 19

Gly Leu Phe Gly Asn Tyr Leu Tyr Lys Lys Thr Arg Arg Tyr Val
1 5 10 15

<210> SEQ ID NO 20
<211> LENGTH: 15
<212> TYPE: PRT
<213> ORGANISM: Pneumocystis carinii

<400> SEQUENCE: 20

Leu Glu Ser Ala Ile Tyr Arg Trp Lys Thr Arg Cys Thr Gln Met
1 5 10 15

<210> SEQ ID NO 21
<211> LENGTH: 15
<212> TYPE: PRT
<213> ORGANISM: Pneumocystis carinii

<400> SEQUENCE: 21

Ile Ile Asn Gly Arg Tyr Val Arg Arg Glu Arg Asp His Asn Lys
1 5 10 15

<210> SEQ ID NO 22
<211> LENGTH: 15
<212> TYPE: PRT
<213> ORGANISM: Pneumocystis carinii

<400> SEQUENCE: 22

Glu Leu Thr Glu Arg Gly Val Trp Arg Ala Ser Thr Arg Leu Ala
1 5 10 15

<210> SEQ ID NO 23
<211> LENGTH: 15
<212> TYPE: PRT
<213> ORGANISM: Pneumocystis carinii

<400> SEQUENCE: 23

Pro Gly Ala Gln His Leu Thr Arg Arg Leu Leu Phe Leu Ile Leu
1 5 10 15

<210> SEQ ID NO 24
<211> LENGTH: 15
<212> TYPE: PRT
<213> ORGANISM: Pneumocystis carinii

<400> SEQUENCE: 24

Thr Phe Ser Asp Phe Thr Met Arg Ser Asp Met Ala Arg Ala Ala
1 5 10 15

<210> SEQ ID NO 25
<211> LENGTH: 15
<212> TYPE: PRT
<213> ORGANISM: Pneumocystis carinii

<400> SEQUENCE: 25

Asn Met Tyr Asp His Met Met Val Leu Leu Asp Ser Arg Ala Ser
1 5 10 15

<210> SEQ ID NO 26
<211> LENGTH: 15
<212> TYPE: PRT
<213> ORGANISM: Pneumocystis carinii

<400> SEQUENCE: 26

Asp Phe Phe Ile Ala Phe Ile Pro Leu Val Val Gln Glu Leu Thr
1 5 10 15

<210> SEQ ID NO 27
<211> LENGTH: 15
<212> TYPE: PRT
<213> ORGANISM: Pneumocystis carinii

<400> SEQUENCE: 27

Lys Leu Arg Lys Arg Ile Val Arg Arg Tyr Ala Thr Leu Phe Phe
1 5 10 15

<210> SEQ ID NO 28
<211> LENGTH: 15
<212> TYPE: PRT
<213> ORGANISM: Pneumocystis carinii

<400> SEQUENCE: 28

Gly Gly Gly Val Ala Ser Leu Leu Met Ile Val Ala Thr Leu Ala
1 5 10 15

<210> SEQ ID NO 29
<211> LENGTH: 15
<212> TYPE: PRT
<213> ORGANISM: Schizosaccharomyces pombe

<400> SEQUENCE: 29

Asn Leu Gln Gly Ile Arg Phe Asp Lys Gly Ile Lys Lys Ala His
1 5 10 15

<210> SEQ ID NO 30
<211> LENGTH: 15
<212> TYPE: PRT
<213> ORGANISM: Schizosaccharomyces pombe

<400> SEQUENCE: 30

Asn Ser Ala Ala Leu Ala Gln Ile Lys Gly Tyr Asp Lys Leu Lys
1 5 10 15

<210> SEQ ID NO 31
<211> LENGTH: 15
<212> TYPE: PRT
<213> ORGANISM: Schizosaccharomyces pombe

<400> SEQUENCE: 31

Val Glu Ser Lys Phe Tyr Val Ser Tyr Asn Ala Arg Glu Ile Ser
1 5 10 15

<210> SEQ ID NO 32
<211> LENGTH: 15
<212> TYPE: PRT
<213> ORGANISM: Schizosaccharomyces pombe

<400> SEQUENCE: 32

Thr Val Gly Asp Met Thr Ile Gln Arg Val Ala His Leu Gln Leu
1 5 10 15

<210> SEQ ID NO 33
<211> LENGTH: 15
<212> TYPE: PRT
<213> ORGANISM: Schizosaccharomyces pombe

<400> SEQUENCE: 33

His Lys Leu Thr Ile Glu Asp Thr Gln Leu Ser Thr Leu Ala Gly
1 5 10 15

<210> SEQ ID NO 34
<211> LENGTH: 15
<212> TYPE: PRT
<213> ORGANISM: Schizosaccharomyces pombe

<400> SEQUENCE: 34

Asn Val Gly Gln Leu Thr Met Arg Ile Leu Pro Asn Leu Gln Gly
1 5 10 15

-continued

<210> SEQ ID NO 35
<211> LENGTH: 15
<212> TYPE: PRT
<213> ORGANISM: Schizosaccharomyces pombe

<400> SEQUENCE: 35

Glu Lys Leu Thr Arg Leu Ala Ser Val Tyr Ala Pro Gln Leu Ala
1 5 10 15

<210> SEQ ID NO 36
<211> LENGTH: 15
<212> TYPE: PRT
<213> ORGANISM: Schizosaccharomyces pombe

<400> SEQUENCE: 36

Phe Tyr Val Ser Tyr Asn Ala Arg Glu Ile Ser Val Thr Leu Pro
1 5 10 15

<210> SEQ ID NO 37
<211> LENGTH: 15
<212> TYPE: PRT
<213> ORGANISM: Schizosaccharomyces pombe

<400> SEQUENCE: 37

Gly Gly Thr Phe Met Ile Ala Asn Ser Ala Ala Leu Ala Gln Ile
1 5 10 15

<210> SEQ ID NO 38
<211> LENGTH: 15
<212> TYPE: PRT
<213> ORGANISM: Schizosaccharomyces pombe

<400> SEQUENCE: 38

Ser Val Gly Gly Glu Leu Arg Phe Glu Lys Leu Thr Arg Leu Ala
1 5 10 15

<210> SEQ ID NO 39
<211> LENGTH: 15
<212> TYPE: PRT
<213> ORGANISM: Schizosaccharomyces pombe

<400> SEQUENCE: 39

Arg Cys Asn Asn Tyr Ala Val Lys Arg Asn Leu Asp Lys Lys Gln
1 5 10 15

<210> SEQ ID NO 40
<211> LENGTH: 15
<212> TYPE: PRT
<213> ORGANISM: Schizosaccharomyces pombe

<400> SEQUENCE: 40

His Leu Phe Thr Pro Met Phe Leu Met Ile Ala Lys Lys Pro Glu
1 5 10 15

<210> SEQ ID NO 41
<211> LENGTH: 15
<212> TYPE: PRT
<213> ORGANISM: Schizosaccharomyces pombe

<400> SEQUENCE: 41

Asn Asn Tyr Ala Val Lys Arg Asn Leu Asp Lys Lys Gln Val Phe
1 5 10 15

<210> SEQ ID NO 42
<211> LENGTH: 15

<212> TYPE: PRT
<213> ORGANISM: Schizosaccharomyces pombe

<400> SEQUENCE: 42

Arg His Glu His Tyr Leu Ala Tyr Arg Met Gly Ile Lys Pro Gly
1 5 10 15

<210> SEQ ID NO 43
<211> LENGTH: 15
<212> TYPE: PRT
<213> ORGANISM: Schizosaccharomyces pombe

<400> SEQUENCE: 43

Pro Gln Met Val Arg Lys Cys Asp Ala Val Glu Ala Ile Lys Lys
1 5 10 15

<210> SEQ ID NO 44
<211> LENGTH: 15
<212> TYPE: PRT
<213> ORGANISM: Schizosaccharomyces pombe

<400> SEQUENCE: 44

Phe Thr Val Phe Arg Thr Ser Arg Leu Gly Lys Leu Val Thr Arg
1 5 10 15

<210> SEQ ID NO 45
<211> LENGTH: 15
<212> TYPE: PRT
<213> ORGANISM: Schizosaccharomyces pombe

<400> SEQUENCE: 45

Lys Leu Val Thr Arg Tyr Ser Val Gln Phe Leu Glu Lys Ile Gly
1 5 10 15

<210> SEQ ID NO 46
<211> LENGTH: 15
<212> TYPE: PRT
<213> ORGANISM: Schizosaccharomyces pombe

<400> SEQUENCE: 46

Tyr Arg Met Gly Ile Lys Pro Gly Ser Arg Val Leu Asp Val Gly
1 5 10 15

<210> SEQ ID NO 47
<211> LENGTH: 15
<212> TYPE: PRT
<213> ORGANISM: Schizosaccharomyces pombe

<400> SEQUENCE: 47

Gly Val Ala Ala Lys Gly Thr Ser Lys Val Gly Asp Thr Leu Ala
1 5 10 15

<210> SEQ ID NO 48
<211> LENGTH: 15
<212> TYPE: PRT
<213> ORGANISM: Schizosaccharomyces pombe

<400> SEQUENCE: 48

Glu Asp Arg Ala Arg Arg Ile Asp Gly Tyr Lys Ser Val Val Asn
1 5 10 15

<210> SEQ ID NO 49
<211> LENGTH: 15
<212> TYPE: PRT
<213> ORGANISM: Schizosaccharomyces pombe

```
<400> SEQUENCE: 49

Tyr Lys Leu Pro Arg Lys Ser Trp Leu Asn Thr Ala Lys Phe Asn
1               5                   10                  15


<210> SEQ ID NO 50
<211> LENGTH: 15
<212> TYPE: PRT
<213> ORGANISM: Schizosaccharomyces pombe

<400> SEQUENCE: 50

Gly Arg Leu Val Ser Leu Lys Asp Thr Ile Arg Ser Phe Lys Glu
1               5                   10                  15


<210> SEQ ID NO 51
<211> LENGTH: 15
<212> TYPE: PRT
<213> ORGANISM: Schizosaccharomyces pombe

<400> SEQUENCE: 51

Glu Ala Asp Lys Leu Thr Val Glu Arg Ala Arg Lys Val Gln Arg
1               5                   10                  15


<210> SEQ ID NO 52
<211> LENGTH: 15
<212> TYPE: PRT
<213> ORGANISM: Schizosaccharomyces pombe

<400> SEQUENCE: 52

Tyr Ala Ser Thr Glu Ala Ala Lys His Asn Lys Gly Ser Ile Lys
1               5                   10                  15


<210> SEQ ID NO 53
<211> LENGTH: 15
<212> TYPE: PRT
<213> ORGANISM: Schizosaccharomyces pombe

<400> SEQUENCE: 53

Pro Gly Ala Arg Ala Arg Val Ala Leu Thr Gly Leu Thr Val Ala
1               5                   10                  15


<210> SEQ ID NO 54
<211> LENGTH: 15
<212> TYPE: PRT
<213> ORGANISM: Schizosaccharomyces pombe

<400> SEQUENCE: 54

Thr Asp Met Gly Ala Met Gln Glu Arg Ile Thr Thr Thr Lys Lys
1               5                   10                  15


<210> SEQ ID NO 55
<211> LENGTH: 15
<212> TYPE: PRT
<213> ORGANISM: Schizosaccharomyces pombe

<400> SEQUENCE: 55

His Val Gly Glu Asn Thr Val Arg Thr Ile Ala Met Asp Gly Thr
1               5                   10                  15


<210> SEQ ID NO 56
<211> LENGTH: 15
<212> TYPE: PRT
<213> ORGANISM: Schizosaccharomyces pombe

<400> SEQUENCE: 56
```

Ser Glu Val Ser Ala Leu Leu Gly Arg Ile Pro Ser Ala Val Gly
1 5 10 15

<210> SEQ ID NO 57
<211> LENGTH: 15
<212> TYPE: PRT
<213> ORGANISM: Schizosaccharomyces pombe

<400> SEQUENCE: 57

Gly Ser Val Gln Gln Met Leu Gln Glu Tyr Lys Ser Leu Gln Asp
1 5 10 15

<210> SEQ ID NO 58
<211> LENGTH: 15
<212> TYPE: PRT
<213> ORGANISM: Schizosaccharomyces pombe

<400> SEQUENCE: 58

Gly Ala Arg Ala Arg Val Ala Leu Thr Gly Leu Thr Val Ala Glu
1 5 10 15

<210> SEQ ID NO 59
<211> LENGTH: 15
<212> TYPE: PRT
<213> ORGANISM: Schizosaccharomyces pombe

<400> SEQUENCE: 59

Phe Gly Gln Met Asn Glu Pro Pro Gly Ala Arg Ala Arg Val Ala
1 5 10 15

<210> SEQ ID NO 60
<211> LENGTH: 15
<212> TYPE: PRT
<213> ORGANISM: Schizosaccharomyces pombe

<400> SEQUENCE: 60

Lys Leu Thr Val Glu Arg Ala Arg Lys Val Gln Arg Phe Leu Ser
1 5 10 15

<210> SEQ ID NO 61
<211> LENGTH: 15
<212> TYPE: PRT
<213> ORGANISM: Schizosaccharomyces pombe

<400> SEQUENCE: 61

Asp Leu Tyr Arg Glu Met Gln Glu Thr Gly Val Ile Lys Leu Glu
1 5 10 15

<210> SEQ ID NO 62
<211> LENGTH: 15
<212> TYPE: PRT
<213> ORGANISM: Schizosaccharomyces pombe

<400> SEQUENCE: 62

Thr Lys Lys Gly Ser Ile Thr Ser Val Gln Ala Val Tyr Val Pro
1 5 10 15

<210> SEQ ID NO 63
<211> LENGTH: 15
<212> TYPE: PRT
<213> ORGANISM: Saccharomyces cerevisiae

<400> SEQUENCE: 63

Lys Asp Asp Leu Lys Arg Lys His Arg Asn Ser Ala Ser Ile Ser

-continued 1 5 10 15

<210> SEQ ID NO 64
<211> LENGTH: 15
<212> TYPE: PRT
<213> ORGANISM: Saccharomyces cerevisiae

<400> SEQUENCE: 64

Gly Thr Met Lys Asn Tyr Ile Ser Ala His Ser Pro Arg Thr Ile
1 5 10 15

<210> SEQ ID NO 65
<211> LENGTH: 15
<212> TYPE: PRT
<213> ORGANISM: Saccharomyces cerevisiae

<400> SEQUENCE: 65

Thr Leu Val Asp Ala Tyr Arg Ser Tyr Ser Lys Pro Val Phe Phe
1 5 10 15

<210> SEQ ID NO 66
<211> LENGTH: 15
<212> TYPE: PRT
<213> ORGANISM: Saccharomyces cerevisiae

<400> SEQUENCE: 66

Gly Asp Arg Trp Asn Gly Pro Lys Lys Ile Glu Ile Arg Gln Ser
1 5 10 15

<210> SEQ ID NO 67
<211> LENGTH: 15
<212> TYPE: PRT
<213> ORGANISM: Saccharomyces cerevisiae

<400> SEQUENCE: 67

His Asp Ala Cys Met Thr Met Leu Ala Met Ala Gly Ile Tyr Leu
1 5 10 15

<210> SEQ ID NO 68
<211> LENGTH: 15
<212> TYPE: PRT
<213> ORGANISM: Saccharomyces cerevisiae

<400> SEQUENCE: 68

Ser Ser Thr Phe Ile Phe Leu Ile Leu Glu Leu Val Val Leu Cys
1 5 10 15

<210> SEQ ID NO 69
<211> LENGTH: 15
<212> TYPE: PRT
<213> ORGANISM: Saccharomyces cerevisiae

<400> SEQUENCE: 69

Tyr Gln Trp Cys Gly Gln Gln Thr Met Gln Thr Ser Gly Tyr Asp
1 5 10 15

<210> SEQ ID NO 70
<211> LENGTH: 15
<212> TYPE: PRT
<213> ORGANISM: Saccharomyces cerevisiae

<400> SEQUENCE: 70

Ile Glu Phe Pro Ser Met Lys Thr Leu Lys Glu Thr Val Gln Met
1 5 10 15

<210> SEQ ID NO 71
<211> LENGTH: 15
<212> TYPE: PRT
<213> ORGANISM: Saccharomyces cerevisiae

<400> SEQUENCE: 71

Ala Cys Met Thr Met Leu Ala Met Ala Gly Ile Tyr Leu Ile Leu
1 5 10 15

<210> SEQ ID NO 72
<211> LENGTH: 15
<212> TYPE: PRT
<213> ORGANISM: Saccharomyces cerevisiae

<400> SEQUENCE: 72

Cys Met Thr Met Leu Ala Met Ala Gly Ile Tyr Leu Ile Leu Asp
1 5 10 15

<210> SEQ ID NO 73
<211> LENGTH: 15
<212> TYPE: PRT
<213> ORGANISM: Saccharomyces cerevisiae

<400> SEQUENCE: 73

Gly Pro Lys Lys Ile Glu Ile Arg Gln Ser Leu Thr Leu Ala Asp
1 5 10 15

<210> SEQ ID NO 74
<211> LENGTH: 15
<212> TYPE: PRT
<213> ORGANISM: Saccharomyces cerevisiae

<400> SEQUENCE: 74

Gly Leu Val Glu Tyr Gln Glu Asp Asp Ser Val Gln Leu Leu Ala
1 5 10 15

<210> SEQ ID NO 75
<211> LENGTH: 15
<212> TYPE: PRT
<213> ORGANISM: Saccharomyces cerevisiae

<400> SEQUENCE: 75

Asn Lys Val Leu Pro Arg Gln Phe Gln Glu Ile Gly Tyr Leu Phe
1 5 10 15

<210> SEQ ID NO 76
<211> LENGTH: 15
<212> TYPE: PRT
<213> ORGANISM: Saccharomyces cerevisiae

<400> SEQUENCE: 76

Pro Asp Leu Asn His Asp Ala Cys Met Thr Met Leu Ala Met Ala
1 5 10 15

<210> SEQ ID NO 77
<211> LENGTH: 15
<212> TYPE: PRT
<213> ORGANISM: Schizosaccharomyces pombe

<400> SEQUENCE: 77

Arg Asp Val Lys Ala Tyr Ile Lys Lys His Ser Asp Arg His Ile
1 5 10 15

<210> SEQ ID NO 78

<211> LENGTH: 15
<212> TYPE: PRT
<213> ORGANISM: Schizosaccharomyces pombe

<400> SEQUENCE: 78

Ile Leu Asp Leu Asn Thr Tyr Arg His Ser Ile Ser Arg Ala His
1 5 10 15

<210> SEQ ID NO 79
<211> LENGTH: 15
<212> TYPE: PRT
<213> ORGANISM: Schizosaccharomyces pombe

<400> SEQUENCE: 79

Ser Ser Ser Leu Val Asp Pro Leu Ala Ser Arg Ser Cys Lys Lys
1 5 10 15

<210> SEQ ID NO 80
<211> LENGTH: 15
<212> TYPE: PRT
<213> ORGANISM: Schizosaccharomyces pombe

<400> SEQUENCE: 80

Ser Lys Thr Asn Glu Arg Phe Tyr Ile Arg Gly Val Asp Tyr Gln
1 5 10 15

<210> SEQ ID NO 81
<211> LENGTH: 15
<212> TYPE: PRT
<213> ORGANISM: Schizosaccharomyces pombe

<400> SEQUENCE: 81

Ala Ile Thr Trp Val Lys Ala Val Thr Arg Asp Val Lys Ala Tyr
1 5 10 15

<210> SEQ ID NO 82
<211> LENGTH: 15
<212> TYPE: PRT
<213> ORGANISM: Schizosaccharomyces pombe

<400> SEQUENCE: 82

Leu Lys Ala Thr Ala Gln Thr His Pro Ile Val Ile Lys Gly Asn
1 5 10 15

<210> SEQ ID NO 83
<211> LENGTH: 15
<212> TYPE: PRT
<213> ORGANISM: Schizosaccharomyces pombe

<400> SEQUENCE: 83

Leu Gly Ile Asn Thr Val Arg Val Tyr Gln Val Asp Asn Ser Ala
1 5 10 15

<210> SEQ ID NO 84
<211> LENGTH: 15
<212> TYPE: PRT
<213> ORGANISM: Schizosaccharomyces pombe

<400> SEQUENCE: 84

Ala Ala Asp Val Ala Glu Asn Arg Leu Gln Leu Ala His Tyr Phe
1 5 10 15

<210> SEQ ID NO 85
<211> LENGTH: 15
<212> TYPE: PRT

<213> ORGANISM: Schizosaccharomyces pombe

<400> SEQUENCE: 85

Phe Cys Gln Ala Leu Phe Ile Thr Val Leu Ile Ala Thr Leu Ser
1 5 10 15

<210> SEQ ID NO 86
<211> LENGTH: 15
<212> TYPE: PRT
<213> ORGANISM: Schizosaccharomyces pombe

<400> SEQUENCE: 86

Met Gly Val Ala Asn Ile Ile Tyr Ala Leu Phe Leu Leu Gly Pro
1 5 10 15

<210> SEQ ID NO 87
<211> LENGTH: 15
<212> TYPE: PRT
<213> ORGANISM: Schizosaccharomyces pombe

<400> SEQUENCE: 87

Lys Cys Met Asn Ala Leu Ser Glu Ala Gly Ile Tyr Val Ile Leu
1 5 10 15

<210> SEQ ID NO 88
<211> LENGTH: 15
<212> TYPE: PRT
<213> ORGANISM: Schizosaccharomyces pombe

<400> SEQUENCE: 88

Ser Ala Glu Pro Asn His Tyr Gly Leu Val Val Ile Asp Lys Asp
1 5 10 15

<210> SEQ ID NO 89
<211> LENGTH: 15
<212> TYPE: PRT
<213> ORGANISM: Schizosaccharomyces pombe

<400> SEQUENCE: 89

Ala His Pro Ala Leu Ser Tyr Asn Lys Val Tyr Leu Gln His Leu
1 5 10 15

<210> SEQ ID NO 90
<211> LENGTH: 15
<212> TYPE: PRT
<213> ORGANISM: Schizosaccharomyces pombe

<400> SEQUENCE: 90

Val Val Asn Asp Glu Asp Thr Thr Ala Ile Thr Trp Val Lys Ala
1 5 10 15

<210> SEQ ID NO 91
<211> LENGTH: 15
<212> TYPE: PRT
<213> ORGANISM: Schizosaccharomyces pombe

<400> SEQUENCE: 91

Thr Ile Leu Val Ala Trp Arg Val Arg Val Lys Pro Thr Val Arg
1 5 10 15

<210> SEQ ID NO 92
<211> LENGTH: 15
<212> TYPE: PRT
<213> ORGANISM: Schizosaccharomyces pombe

<400> SEQUENCE: 92

Glu Gln Thr Ser Leu Leu Tyr Pro Glu Val Ser Arg Lys Lys Glu
1 5 10 15

<210> SEQ ID NO 93
<211> LENGTH: 15
<212> TYPE: PRT
<213> ORGANISM: Schizosaccharomyces pombe

<400> SEQUENCE: 93

Leu Phe Ala Phe Tyr Trp Val Glu Lys Asn Ile Ala Val Glu Pro
1 5 10 15

<210> SEQ ID NO 94
<211> LENGTH: 15
<212> TYPE: PRT
<213> ORGANISM: Schizosaccharomyces pombe

<400> SEQUENCE: 94

Gly Gly Leu Ile Ala Gln Arg Trp Gly Trp Arg Thr Ala Phe His
1 5 10 15

<210> SEQ ID NO 95
<211> LENGTH: 15
<212> TYPE: PRT
<213> ORGANISM: Schizosaccharomyces pombe

<400> SEQUENCE: 95

Ile Ala Phe Ala Gly Phe Trp Cys Ser Leu Arg Ile Lys Gln Phe
1 5 10 15

<210> SEQ ID NO 96
<211> LENGTH: 15
<212> TYPE: PRT
<213> ORGANISM: Schizosaccharomyces pombe

<400> SEQUENCE: 96

Phe Leu Leu Val Thr Gly Ile Thr Ala Leu Val Val Thr Phe Asn
1 5 10 15

<210> SEQ ID NO 97
<211> LENGTH: 15
<212> TYPE: PRT
<213> ORGANISM: Schizosaccharomyces pombe

<400> SEQUENCE: 97

Gly Phe Phe Phe Met Leu Met Gly Ile Val Ser Phe Ala Val Leu
1 5 10 15

<210> SEQ ID NO 98
<211> LENGTH: 15
<212> TYPE: PRT
<213> ORGANISM: Schizosaccharomyces pombe

<400> SEQUENCE: 98

Val Ala Trp Arg Val Arg Val Lys Pro Thr Val Arg Asn Ser Asn
1 5 10 15

<210> SEQ ID NO 99
<211> LENGTH: 15
<212> TYPE: PRT
<213> ORGANISM: Schizosaccharomyces pombe

<400> SEQUENCE: 99

Ala Phe Pro Trp Val Ser Pro Val Ile Ile Thr Leu Leu Val Ser
1 5 10 15

<210> SEQ ID NO 100
<211> LENGTH: 15
<212> TYPE: PRT
<213> ORGANISM: Schizosaccharomyces pombe

<400> SEQUENCE: 100

Thr Thr Leu Ser Ile Leu Met Lys Gln Leu Ala Ser Asn Leu Lys
1 5 10 15

<210> SEQ ID NO 101
<211> LENGTH: 15
<212> TYPE: PRT
<213> ORGANISM: Schizosaccharomyces pombe

<400> SEQUENCE: 101

Tyr Ile Val Thr Ala Tyr Leu Ile Thr Asn Thr Ala Phe Gln Pro
1 5 10 15

<210> SEQ ID NO 102
<211> LENGTH: 15
<212> TYPE: PRT
<213> ORGANISM: Schizosaccharomyces pombe

<400> SEQUENCE: 102

Gly Phe Leu Ser Ala Leu Asp Met Thr Ile Val Ala Ser Leu Tyr
1 5 10 15

<210> SEQ ID NO 103
<211> LENGTH: 15
<212> TYPE: PRT
<213> ORGANISM: Schizosaccharomyces pombe

<400> SEQUENCE: 103

Phe His Phe Gln Val Pro Met Gly Ile Leu Ser Thr Ile Leu Val
1 5 10 15

<210> SEQ ID NO 104
<211> LENGTH: 15
<212> TYPE: PRT
<213> ORGANISM: Schizosaccharomyces pombe

<400> SEQUENCE: 104

Arg Leu Ser Asp Ile Phe Gly Arg Arg Pro Thr Val Val Phe Ala
1 5 10 15

<210> SEQ ID NO 105
<211> LENGTH: 12
<212> TYPE: PRT
<213> ORGANISM: Pneumocystis murina

<400> SEQUENCE: 105

Phe Pro Glu Lys Ile Glu Val Glu Asn Leu Tyr Lys
1 5 10

<210> SEQ ID NO 106
<211> LENGTH: 25
<212> TYPE: PRT
<213> ORGANISM: Pneumocystis murina

<400> SEQUENCE: 106

His Gly Gln Ile Glu Val Thr Cys Ala Lys Ser Gly Ile Tyr Glu Asn
1 5 10 15

```
Ser Leu Trp Tyr Ile Glu Asp Asn Ser
            20                  25


<210> SEQ ID NO 107
<211> LENGTH: 699
<212> TYPE: PRT
<213> ORGANISM: Pneumocystis murina

<400> SEQUENCE: 107

Met Val Tyr Asn Phe Asn Asn Leu Ile Gly Gln Pro Asn Ile Lys Leu
1               5                   10                  15

Arg Ile Asn Asp Ile Lys Tyr Leu Ile Ile Leu Thr Ile Ile Gly Ser
            20                  25                  30

Cys Val Gln Thr Tyr Met Ile Asn His Pro Ser Asp Leu Val Phe Asn
        35                  40                  45

Glu Ser Tyr Met Met Gln Leu Ala Tyr Asn Tyr Ile Lys Lys Glu Phe
    50                  55                  60

Tyr Ile Asp Lys Asp Pro Pro Tyr Ala Arg Met Leu Tyr Ala Leu Phe
65                  70                  75                  80

Ile Trp Val Leu Gly His Leu Pro Val Asn Leu Tyr Thr Ile Lys Lys
                85                  90                  95

Ala Tyr Ser Leu Tyr Arg Ile Pro Arg Ile Pro Thr Arg Leu Phe Ser
            100                 105                 110

Cys Ile Phe Gly Ile Leu Leu Ser Pro Ile Thr Tyr Leu Thr Leu Arg
        115                 120                 125

Val Met Arg Phe Thr Arg Asn Thr Ala Ile Leu Gly Ser Ile Leu Ile
    130                 135                 140

Ile Phe Glu Ser Ser Val Val Ile Gln Ser Arg Phe Val Phe His Asp
145                 150                 155                 160

Ser Leu Ala Leu Phe Phe Thr Ala Leu Thr His Leu Phe Trp Arg Leu
                165                 170                 175

Phe Glu Ser Cys Gln Gln Ile Pro Phe Arg Lys Ala Trp Trp Ala Tyr
            180                 185                 190

Leu Met Ala Thr Gly Phe Thr Leu Gly Ala Leu Ile Ser Thr Lys Trp
        195                 200                 205

Val Gly Ile Phe Thr Phe Phe Trp Ile Gly Leu Leu Ala Cys Leu Gln
    210                 215                 220

Leu Trp His Phe Ile Glu Asp Leu Thr Met Ala Leu Thr Thr Trp Val
225                 230                 235                 240

Lys His Phe Phe Phe Arg Phe Phe Ser Leu Ile Ile Ile Pro Thr Leu
                245                 250                 255

Phe Tyr Ile Ile Thr Phe Tyr Leu His Ile Asn Leu Leu Lys Asn Ala
            260                 265                 270

Asn Asp Gly Val Phe Leu Ser Pro Glu Phe Leu Ser Thr Phe Asp Asn
        275                 280                 285

Arg Ile Val Lys Ser Val Pro Ala Pro Val Ser Tyr Gly Ser Thr Val
    290                 295                 300

Thr Ile Arg His Leu Asn Ser Pro Tyr Gly Tyr Leu His Ser His Phe
305                 310                 315                 320

Asp Ser Tyr Pro Ser Gly Ser Lys Gln Gln Gln Val Thr Leu Tyr Leu
                325                 330                 335

Tyr Glu Asp Ala Asn Asn Asn Trp Leu Ile Thr Asp Ser Gly Asp Ala
            340                 345                 350

Asn Tyr Glu Val Phe Ser Phe Ser Thr Ile Gln Asp Gly Ser Ile Ile
```

```
        355                 360                 365

Arg Leu Tyr His Leu Glu Thr Asn Arg Arg Leu His Ser His Asp Val
    370                 375                 380

Arg Pro Ser Leu Ser Asp Ile Asp Trp Gln Asn Glu Val Ser Gly Tyr
385                 390                 395                 400

Gly His Lys Gly Phe Pro Gly Asp His Asn Asp Leu Phe Arg Ile Glu
                405                 410                 415

Ile Asp Lys Ser Arg Ser Tyr Thr Asp Glu Ser Lys Ile Ser Val Arg
            420                 425                 430

Ala Ile Glu Thr Lys Phe Arg Leu Ile His Val Ser Thr Gly Cys Ala
        435                 440                 445

Leu Phe Ser Asn Asn Ile Tyr Leu Pro Glu Trp Gly His Gly Gln Ile
    450                 455                 460

Glu Val Thr Cys Ala Lys Ser Gly Ile Tyr Glu Asn Ser Leu Trp Tyr
465                 470                 475                 480

Ile Glu Asp Asn Ser His Asp Asp Phe Ser Ile Asn Ile Glu Lys Val
                485                 490                 495

Ser Tyr Lys Lys Ile Ala Phe Phe Gln Lys Phe Phe Glu Leu His Lys
            500                 505                 510

His Met Trp Glu Glu Asn Phe His Leu Glu Asp Leu Tyr Asn Ala Gly
        515                 520                 525

Thr His Pro Phe Ser Trp Pro Phe Leu Arg Arg Gly Ile His Phe Trp
    530                 535                 540

Ile Lys Lys Asn Asp Gln Ile Tyr Phe Leu Gly Asn Pro Leu Ile Trp
545                 550                 555                 560

Leu Leu Thr Leu Ala Phe Val Gly Val Tyr Cys Ile Phe Lys Leu Phe
                565                 570                 575

Val Ile Leu Ser Glu Gln Arg Gly Tyr Pro Ser Tyr Asn Asp Lys Val
            580                 585                 590

Tyr Leu Arg Tyr Asp Tyr Leu Ile Gly Thr Ser Leu Leu Gly Trp Ile
        595                 600                 605

Phe His Tyr Phe Pro Tyr Tyr Phe Met Glu Lys Gln Phe Leu Leu Ser
    610                 615                 620

Gln Tyr Ile Pro Ala Leu Tyr Phe Ser Ile Leu Ser Leu Cys Ser Phe
625                 630                 635                 640

Trp Asp Phe Ile Ser Val Arg Phe Leu Gln Arg Leu Gln Ile Lys Leu
                645                 650                 655

Phe Thr Leu Phe Phe Phe Lys Ile Val Ile Ser Val Tyr Phe Ile Met
            660                 665                 670

Ala Pro Leu Ile Tyr Gly Tyr Ser Met Arg Lys Glu His Cys Ser Phe
        675                 680                 685

Ile Lys Phe Phe Lys Thr Trp Asp Leu Arg Cys
    690                 695
```

<210> SEQ ID NO 108
<211> LENGTH: 1245
<212> TYPE: DNA
<213> ORGANISM: Artificial Sequence
<220> FEATURE:
<223> OTHER INFORMATION: Recombinant Meu10 nucleic acid
<220> FEATURE:
<221> NAME/KEY: misc_feature
<222> LOCATION: (1)..(18)
<223> OTHER INFORMATION: Restriction enzyme/Gateway sites
<220> FEATURE:
<221> NAME/KEY: misc_feature
<222> LOCATION: (19)..(78)

-continued

<223> OTHER INFORMATION: Artificial leader sequence
<220> FEATURE:
<221> NAME/KEY: misc_feature
<222> LOCATION: (79)..(1137)
<223> OTHER INFORMATION: Meu10 ectodomain coding sequence
<220> FEATURE:
<221> NAME/KEY: misc_feature
<222> LOCATION: (1138)..(1245)
<223> OTHER INFORMATION: Histidine and myc tags

<400> SEQUENCE: 108
gcggccgcaa gcttcaccat ggagacagac acactcctgc tatgggtact gctgctctgg 60
gttccaggtt ccactggtga aaaatgcgat gaggatatta atgtgaaatc gcaaacagat 120
cttgaccgta tctctgaatg cacagtattt gaaggcagta tttatgttac atcttctatt 180
cctctaattg atcttggcaa tcttgaacac atactaggag atctcgttat ctatgaaaat 240
gatgatattt tattatttaa agcctttaat ctcgttagcg tacaaggaaa attagtgttt 300
aaaaaattaa cagcgcttga aaaaatagaa ttaccagcac ttagttctgc agatactatg 360
attctatttc aatgcgcaca gctccaaacc ctcaatttaa atacaggaat aagtcgtctt 420
aatcatatta cagtttcaga tacatcatta cgcaatatat caggattttt aatgaaatct 480
cttatttctt taaatattaa taataataat tatcttagca cttttaacat gtcgaatcta 540
gttacaatcg gagataagtt ttcctttatg caaaatggtt tagtccaaaa taattacgga 600
atccctattt ctttgccttc tttagaaagc agtggtggac tgtttttaca aagtgtttct 660
tctgtagaac tagaacaatt aaaaaatatt acaggagatt tcggattatc tctaagcaca 720
ttaagcaatc ttactctaga atcattatct tttattcaag gatcattatc tatttataat 780
aacactgtat taactagtct tgaatttcca aatctaattt ccatcggagg gacttttcta 840
atttctgata atccaaattt acatgttatc tcaggatttg ataaagtccg atatattggc 900
ggttcgattc attggacagg atttttaaaa agtatttctt tatccagtat cactgacata 960
aaaggcacag taaaaatttt atcaagcact catatttcat gtccagcgtt tactaaatca 1020
cgcgctatta ttcaaggagc taatccagta tgtaaaagtt ccataagttc tgattctggc 1080
ggtgcttcca gtaatagaaa aaatggttct tatagtagta aaaagaatgg gtttatgttg 1140
tacaaagtgg ttcgatctag agggcccttc gaaggtaagc ctatccctaa ccctctcctc 1200
ggtctcgatt ctacgcgtac cggtcatcat caccatcacc attga 1245

<210> SEQ ID NO 109
<211> LENGTH: 408
<212> TYPE: PRT
<213> ORGANISM: Artificial Sequence
<220> FEATURE:
<223> OTHER INFORMATION: Recombinant Meu10 protein
<220> FEATURE:
<221> NAME/KEY: MISC_FEATURE
<222> LOCATION: (1)..(21)
<223> OTHER INFORMATION: Artificial leader sequence
<220> FEATURE:
<221> NAME/KEY: MISC_FEATURE
<222> LOCATION: (22)..(373)
<223> OTHER INFORMATION: Meu10 ectodomain sequence
<220> FEATURE:
<221> NAME/KEY: MISC_FEATURE
<222> LOCATION: (374)..(408)
<223> OTHER INFORMATION: Histidine and myc tags

<400> SEQUENCE: 109

Met Glu Thr Asp Thr Leu Leu Leu Trp Val Leu Leu Leu Trp Val Pro
1 5 10 15

```
Gly Ser Thr Gly Glu Lys Cys Asp Glu Asp Ile Asn Val Lys Ser Gln
            20                  25                  30

Thr Asp Leu Asp Arg Ile Ser Glu Cys Thr Val Phe Glu Gly Ser Ile
        35                  40                  45

Tyr Val Thr Ser Ser Ile Pro Leu Ile Asp Leu Gly Asn Leu Glu His
    50                  55                  60

Ile Leu Gly Asp Leu Val Ile Tyr Glu Asn Asp Asp Ile Leu Leu Phe
65                  70                  75                  80

Lys Ala Phe Asn Leu Val Ser Val Gln Gly Lys Leu Val Phe Lys Lys
                85                  90                  95

Leu Thr Ala Leu Glu Lys Ile Glu Leu Pro Ala Leu Ser Ser Ala Asp
            100                 105                 110

Thr Met Ile Leu Phe Gln Cys Ala Gln Leu Gln Thr Leu Asn Leu Asn
        115                 120                 125

Thr Gly Ile Ser Arg Leu Asn His Ile Thr Val Ser Asp Thr Ser Leu
    130                 135                 140

Arg Asn Ile Ser Gly Phe Leu Met Lys Ser Leu Ile Ser Leu Asn Ile
145                 150                 155                 160

Asn Asn Asn Asn Tyr Leu Ser Thr Phe Asn Met Ser Asn Leu Val Thr
                165                 170                 175

Ile Gly Asp Lys Phe Ser Phe Met Gln Asn Gly Leu Val Gln Asn Asn
            180                 185                 190

Tyr Gly Ile Pro Ile Ser Leu Pro Ser Leu Glu Ser Ser Gly Gly Leu
        195                 200                 205

Phe Leu Gln Ser Val Ser Ser Val Glu Leu Glu Gln Leu Lys Asn Ile
    210                 215                 220

Thr Gly Asp Phe Gly Leu Ser Leu Ser Thr Leu Ser Asn Leu Thr Leu
225                 230                 235                 240

Glu Ser Leu Ser Phe Ile Gln Gly Ser Leu Ser Ile Tyr Asn Asn Thr
                245                 250                 255

Val Leu Thr Ser Leu Glu Phe Pro Asn Leu Ile Ser Ile Gly Gly Thr
            260                 265                 270

Phe Leu Ile Ser Asp Asn Pro Asn Leu His Val Ile Ser Gly Phe Asp
        275                 280                 285

Lys Val Arg Tyr Ile Gly Gly Ser Ile His Trp Thr Gly Phe Leu Lys
    290                 295                 300

Ser Ile Ser Leu Ser Ser Ile Thr Asp Ile Lys Gly Thr Val Lys Ile
305                 310                 315                 320

Leu Ser Ser Thr His Ile Ser Cys Pro Ala Phe Thr Lys Ser Arg Ala
                325                 330                 335

Ile Ile Gln Gly Ala Asn Pro Val Cys Lys Ser Ser Ile Ser Ser Asp
            340                 345                 350

Ser Gly Gly Ala Ser Ser Asn Arg Lys Asn Gly Ser Tyr Ser Ser Lys
        355                 360                 365

Lys Asn Gly Phe Met Leu Tyr Lys Val Val Arg Ser Arg Gly Pro Phe
    370                 375                 380

Glu Gly Lys Pro Ile Pro Asn Pro Leu Leu Gly Leu Asp Ser Thr Arg
385                 390                 395                 400

Thr Gly His His His His His His
                405
```

<210> SEQ ID NO 110
<211> LENGTH: 1930
<212> TYPE: DNA

<213> ORGANISM: Artificial Sequence
<220> FEATURE:
<223> OTHER INFORMATION: Recombinant GSC-1 nucleic acid
<220> FEATURE:
<221> NAME/KEY: misc_feature
<222> LOCATION: (1)..(10)
<223> OTHER INFORMATION: Restriction enzyme/Gateway sites
<220> FEATURE:
<221> NAME/KEY: misc_feature
<222> LOCATION: (11)..(73)
<223> OTHER INFORMATION: Artificial leader sequence
<220> FEATURE:
<221> NAME/KEY: misc_feature
<222> LOCATION: (74)..(1822)
<223> OTHER INFORMATION: GSC-1 ectodomain coding sequence
<220> FEATURE:
<221> NAME/KEY: misc_feature
<222> LOCATION: (1823)..(1930)
<223> OTHER INFORMATION: Histidine and myc tags

<400> SEQUENCE: 110

```
gtcgaccacc atggagacag acacactcct gctatgggta ctgctgctct gggttccagg     60

ttccactggt gaaaatatat tctcaagaat gccgaaaagg atttattcta agattttggc    120

cacaaatgat atggaaataa aatataaacc taaagttctt atttcacaag tttggaatgc    180

cgttgttata tcgatgtatc gtgaacatct tcttgcgatt gatcatgttc aaaagttatt    240

atatcatcag gttccttctg aacaagaagg aaaaagaaca ttaagggcac caacattttt    300

catatcgcaa gaggatcatt cttttaaaac ggagtttttt ccttcacata gtgaagcaga    360

acgtcgtatt tcattttttg ctcaatctct ttctactcca attcctgagc cacttcctgt    420

tgacaatatg cctactttta ctgttcttgt tcctcattat ggtgaaaaga ttttatattc    480

tttaagggag attattcgtg aggatgacca attatcaaga gtaacactac tagaatatct    540

taaacaattg catcctgtag aatgggattg ttttgttaag gatactaaga tattagcaga    600

agagacttca ctttataatg gaggagtccc ttttgataaa gatgaaaaag atacggtaaa    660

aagcaagata gatgatttac ctttttattg tgttgggttt aagtcttctg cgccagaata    720

tacattgaga acacgtattt gggcatcatt acgctctcaa actttatata gaactgtttc    780

tgggtttatg aactattcac gtgctattaa gcttctttat cgtgttgaaa atccagatgt    840

tgttcaaatg tttggtggaa atactgataa attggaacat gaattagaaa ggatggcgcg    900

tagaaaattt aaatttgtta tatcaatgca acggtttttc aaatttagta aagaagagtt    960

ggaaaatacg gaatttcttc ttcgggctta tccagatctt cagattgcat atttagatga   1020

agagcctccg atgaatgaag gtgatgaacc gaaaatatac tcttctttaa tcgatggtta   1080

ttcagaaatt atggaaaatg gtaaacgacg gccgaaattt agaattcaat tatctggtaa   1140

tcctattctt ggcgatggta aaagtgataa tcagaatcat gcaatcatat tttatcgcgg   1200

tgaatacatt cagcttattg atgctaatca agataattat ctggaagaat gcttaaaaat   1260

tcgttcggtt ttggccgaat ttgaagaaat gactcctata gaagagtcgc cgtataatcc   1320

gaatgaagtt tcaagtgctg ctaatccggt ggctatttta ggtgctcgag aatacatttt   1380

ttcggaaaat ataggtgttt tgggtgacgt agctgcagga aaagaacaaa cttttggaac   1440

attgtttgct cgtactttag ctcagattgg agggaagctt cattatggtc atcctgattt   1500

cttgaatggc cctttttatga ctactagagg gggtgtttca aaggctcaga aaggtttaca   1560

tctcaatgaa gatatatatg ctggcatgac tgcattactt agaggcggcc gtattaagca   1620

ttgtgaatat tatcagtgtg gaaagggtcg tgatcttgga tttggttcta ttttaaattt   1680

tactacaaag gttggcacag gaatgggtga acaaatgctt tctagagaat attattatct   1740
```

```
tggcacgcaa cttccactgg ataggttttt gtcgttttat tatgctcatc ctggatttca   1800

tatcaataat ctttttatta ttttgtacaa agtggttcga tctagagggc ccttcgaagg   1860

taagcctatc cctaaccctc tcctcggtct cgattctacg cgtaccggtc atcatcacca   1920

tcaccattga                                                          1930


<210> SEQ ID NO 111
<211> LENGTH: 641
<212> TYPE: PRT
<213> ORGANISM: Artificial Sequence
<220> FEATURE:
<223> OTHER INFORMATION: Recombinant GSC-1 protein
<220> FEATURE:
<221> NAME/KEY: MISC_FEATURE
<222> LOCATION: (1)..(21)
<223> OTHER INFORMATION: Artificial leader sequence
<220> FEATURE:
<221> NAME/KEY: MISC_FEATURE
<222> LOCATION: (22)..(606)
<223> OTHER INFORMATION: GSC-1 ectodomain sequence
<220> FEATURE:
<221> NAME/KEY: MISC_FEATURE
<222> LOCATION: (607)..(641)
<223> OTHER INFORMATION: Histidine and myc tags

<400> SEQUENCE: 111

Met Glu Thr Asp Thr Leu Leu Leu Trp Val Leu Leu Leu Trp Val Pro
1               5                   10                  15

Gly Ser Thr Gly Glu Asn Ile Phe Ser Arg Met Pro Lys Arg Ile Tyr
            20                  25                  30

Ser Lys Ile Leu Ala Thr Asn Asp Met Glu Ile Lys Tyr Lys Pro Lys
        35                  40                  45

Val Leu Ile Ser Gln Val Trp Asn Ala Val Val Ile Ser Met Tyr Arg
    50                  55                  60

Glu His Leu Leu Ala Ile Asp His Val Gln Lys Leu Leu Tyr His Gln
65                  70                  75                  80

Val Pro Ser Glu Gln Glu Gly Lys Arg Thr Leu Arg Ala Pro Thr Phe
                85                  90                  95

Phe Ile Ser Gln Glu Asp His Ser Phe Lys Thr Glu Phe Phe Pro Ser
            100                 105                 110

His Ser Glu Ala Glu Arg Arg Ile Ser Phe Phe Ala Gln Ser Leu Ser
        115                 120                 125

Thr Pro Ile Pro Glu Pro Leu Pro Val Asp Asn Met Pro Thr Phe Thr
    130                 135                 140

Val Leu Val Pro His Tyr Gly Glu Lys Ile Leu Tyr Ser Leu Arg Glu
145                 150                 155                 160

Ile Ile Arg Glu Asp Asp Gln Leu Ser Arg Val Thr Leu Leu Glu Tyr
                165                 170                 175

Leu Lys Gln Leu His Pro Val Glu Trp Asp Cys Phe Val Lys Asp Thr
            180                 185                 190

Lys Ile Leu Ala Glu Glu Thr Ser Leu Tyr Asn Gly Gly Val Pro Phe
        195                 200                 205

Asp Lys Asp Glu Lys Asp Thr Val Lys Ser Lys Ile Asp Asp Leu Pro
    210                 215                 220

Phe Tyr Cys Val Gly Phe Lys Ser Ser Ala Pro Glu Tyr Thr Leu Arg
225                 230                 235                 240

Thr Arg Ile Trp Ala Ser Leu Arg Ser Gln Thr Leu Tyr Arg Thr Val
                245                 250                 255
```

-continued

```
Ser Gly Phe Met Asn Tyr Ser Arg Ala Ile Lys Leu Leu Tyr Arg Val
            260                 265                 270

Glu Asn Pro Asp Val Val Gln Met Phe Gly Gly Asn Thr Asp Lys Leu
        275                 280                 285

Glu His Glu Leu Glu Arg Met Ala Arg Arg Lys Phe Lys Phe Val Ile
    290                 295                 300

Ser Met Gln Arg Phe Phe Lys Phe Ser Lys Glu Glu Leu Glu Asn Thr
305                 310                 315                 320

Glu Phe Leu Leu Arg Ala Tyr Pro Asp Leu Gln Ile Ala Tyr Leu Asp
                325                 330                 335

Glu Glu Pro Pro Met Asn Glu Gly Asp Glu Pro Lys Ile Tyr Ser Ser
            340                 345                 350

Leu Ile Asp Gly Tyr Ser Glu Ile Met Glu Asn Gly Lys Arg Arg Pro
        355                 360                 365

Lys Phe Arg Ile Gln Leu Ser Gly Asn Pro Ile Leu Gly Asp Gly Lys
    370                 375                 380

Ser Asp Asn Gln Asn His Ala Ile Ile Phe Tyr Arg Gly Glu Tyr Ile
385                 390                 395                 400

Gln Leu Ile Asp Ala Asn Gln Asp Asn Tyr Leu Glu Glu Cys Leu Lys
                405                 410                 415

Ile Arg Ser Val Leu Ala Glu Phe Glu Glu Met Thr Pro Ile Glu Glu
            420                 425                 430

Ser Pro Tyr Asn Pro Asn Glu Val Ser Ser Ala Ala Asn Pro Val Ala
        435                 440                 445

Ile Leu Gly Ala Arg Glu Tyr Ile Phe Ser Glu Asn Ile Gly Val Leu
    450                 455                 460

Gly Asp Val Ala Ala Gly Lys Glu Gln Thr Phe Gly Thr Leu Phe Ala
465                 470                 475                 480

Arg Thr Leu Ala Gln Ile Gly Gly Lys Leu His Tyr Gly His Pro Asp
                485                 490                 495

Phe Leu Asn Gly Pro Phe Met Thr Thr Arg Gly Gly Val Ser Lys Ala
            500                 505                 510

Gln Lys Gly Leu His Leu Asn Glu Asp Ile Tyr Ala Gly Met Thr Ala
        515                 520                 525

Leu Leu Arg Gly Gly Arg Ile Lys His Cys Glu Tyr Tyr Gln Cys Gly
    530                 535                 540

Lys Gly Arg Asp Leu Gly Phe Gly Ser Ile Leu Asn Phe Thr Thr Lys
545                 550                 555                 560

Val Gly Thr Gly Met Gly Glu Gln Met Leu Ser Arg Glu Tyr Tyr Tyr
                565                 570                 575

Leu Gly Thr Gln Leu Pro Leu Asp Arg Phe Leu Ser Phe Tyr Tyr Ala
            580                 585                 590

His Pro Gly Phe His Ile Asn Asn Leu Phe Ile Ile Gly Ser Leu Tyr
        595                 600                 605

Lys Val Val Arg Ser Arg Gly Pro Phe Glu Gly Lys Pro Ile Pro Asn
    610                 615                 620

Pro Leu Leu Gly Leu Asp Ser Thr Arg Thr Gly His His His His His
625                 630                 635                 640

His
```

<210> SEQ ID NO 112
<211> LENGTH: 10
<212> TYPE: PRT
<213> ORGANISM: Pneumocystis jirovecii

<400> SEQUENCE: 112

Glu Ser Tyr Leu Thr Arg Asn Arg Ser Lys
1 5 10

<210> SEQ ID NO 113
<211> LENGTH: 7
<212> TYPE: PRT
<213> ORGANISM: Pneumocystis jirovecii

<400> SEQUENCE: 113

Leu Thr Arg Lys Asn Gly Thr
1 5

<210> SEQ ID NO 114
<211> LENGTH: 9
<212> TYPE: PRT
<213> ORGANISM: Pneumocystis jirovecii

<400> SEQUENCE: 114

Tyr Leu Val Ser Val Gly His Asp Glu
1 5

<210> SEQ ID NO 115
<211> LENGTH: 10
<212> TYPE: PRT
<213> ORGANISM: Pneumocystis jirovecii

<400> SEQUENCE: 115

Glu Ser Pro Arg Gln Leu Ile Ser Ile Gly
1 5 10

<210> SEQ ID NO 116
<211> LENGTH: 9
<212> TYPE: PRT
<213> ORGANISM: Pneumocystis jirovecii

<400> SEQUENCE: 116

Trp Val Gln Ile Met Val Ala Lys Ile
1 5

<210> SEQ ID NO 117
<211> LENGTH: 9
<212> TYPE: PRT
<213> ORGANISM: Pneumocystis jirovecii

<400> SEQUENCE: 117

Gln Ile Met Leu Phe Trp Ser Gly Leu
1 5

<210> SEQ ID NO 118
<211> LENGTH: 12
<212> TYPE: PRT
<213> ORGANISM: Pneumocystis jirovecii

<400> SEQUENCE: 118

Gly Thr Gly Ile Asn Asn Pro Phe Ser Ala Leu Ile
1 5 10

<210> SEQ ID NO 119
<211> LENGTH: 7
<212> TYPE: PRT
<213> ORGANISM: Pneumocystis jirovecii

<400> SEQUENCE: 119

Leu Ile Gly Ile Ile Leu Gln
1 5

<210> SEQ ID NO 120
<211> LENGTH: 9
<212> TYPE: PRT
<213> ORGANISM: Pneumocystis jirovecii

<400> SEQUENCE: 120

Thr Ile Thr Phe Leu Ile Gly Ile Ile
1 5

<210> SEQ ID NO 121
<211> LENGTH: 20
<212> TYPE: PRT
<213> ORGANISM: Pneumocystis jirovecii

<400> SEQUENCE: 121

Phe Tyr Gly Arg Arg Thr Lys Met Asp Pro Leu Leu Asn Ser Cys Val
1 5 10 15

Ile Gly Gly Leu
20

<210> SEQ ID NO 122
<211> LENGTH: 8
<212> TYPE: PRT
<213> ORGANISM: Pneumocystis jirovecii

<400> SEQUENCE: 122

Leu Ser Ile Gly Glu Leu Ser Val
1 5

<210> SEQ ID NO 123
<211> LENGTH: 11
<212> TYPE: PRT
<213> ORGANISM: Pneumocystis jirovecii

<400> SEQUENCE: 123

Lys Ile Trp Gly Thr Ala Ser Gly Leu Ser Ile
1 5 10

<210> SEQ ID NO 124
<211> LENGTH: 10
<212> TYPE: PRT
<213> ORGANISM: Pneumocystis jirovecii

<400> SEQUENCE: 124

Ser Asn His Ile Ala Ser Ala Val Val Ile
1 5 10

<210> SEQ ID NO 125
<211> LENGTH: 7
<212> TYPE: PRT
<213> ORGANISM: Pneumocystis jirovecii

<400> SEQUENCE: 125

Ala Val Met Ala Val Phe Ser
1 5

<210> SEQ ID NO 126
<211> LENGTH: 15
<212> TYPE: PRT
<213> ORGANISM: Pneumocystis jirovecii

<400> SEQUENCE: 126

Gly Leu Phe Gly Asn Tyr Leu Tyr Lys Lys Thr Arg Arg Tyr Val
1 5 10 15

<210> SEQ ID NO 127
<211> LENGTH: 15
<212> TYPE: PRT
<213> ORGANISM: Pneumocystis jirovecii

<400> SEQUENCE: 127

Leu Glu Ser Ala Ile Tyr Arg Trp Lys Thr Lys Cys Ser Gln Met
1 5 10 15

<210> SEQ ID NO 128
<211> LENGTH: 15
<212> TYPE: PRT
<213> ORGANISM: Pneumocystis jirovecii

<400> SEQUENCE: 128

Ile Ile Asn Gly Arg Tyr Val Arg Arg Glu Arg Asp His Asn Lys
1 5 10 15

<210> SEQ ID NO 129
<211> LENGTH: 15
<212> TYPE: PRT
<213> ORGANISM: Pneumocystis jirovecii

<400> SEQUENCE: 129

Glu Leu Thr Glu Arg Gly Val Trp Arg Ala Ser Thr Arg Leu Ala
1 5 10 15

<210> SEQ ID NO 130
<211> LENGTH: 14
<212> TYPE: PRT
<213> ORGANISM: Pneumocystis jirovecii

<400> SEQUENCE: 130

Gly Ala Gln His Leu Thr Arg Arg Leu Leu Phe Leu Ile Leu
1 5 10

<210> SEQ ID NO 131
<211> LENGTH: 14
<212> TYPE: PRT
<213> ORGANISM: Pneumocystis jirovecii

<400> SEQUENCE: 131

Phe Ser Asp Phe Thr Met Arg Ser Asp Met Ala Arg Ala Ala
1 5 10

<210> SEQ ID NO 132
<211> LENGTH: 15
<212> TYPE: PRT
<213> ORGANISM: Pneumocystis jirovecii

<400> SEQUENCE: 132

Asn Met Tyr Asp His Met Met Val Leu Leu Asp Ser Arg Ala Ser
1 5 10 15

<210> SEQ ID NO 133
<211> LENGTH: 14
<212> TYPE: PRT
<213> ORGANISM: Pneumocystis jirovecii

<400> SEQUENCE: 133

Phe Phe Ile Ala Phe Ile Pro Leu Val Val Gln Glu Leu Thr
1 5 10

<210> SEQ ID NO 134
<211> LENGTH: 15
<212> TYPE: PRT
<213> ORGANISM: Pneumocystis jirovecii

<400> SEQUENCE: 134

Lys Leu Arg Lys Arg Ile Val Arg Arg Tyr Ala Thr Leu Phe Phe
1 5 10 15

<210> SEQ ID NO 135
<211> LENGTH: 15
<212> TYPE: PRT
<213> ORGANISM: Pneumocystis jirovecii

<400> SEQUENCE: 135

Gly Gly Gly Val Ala Ser Leu Leu Met Ile Ile Ala Thr Leu Ala
1 5 10 15

<210> SEQ ID NO 136
<211> LENGTH: 11
<212> TYPE: PRT
<213> ORGANISM: Pneumocystis jirovecii

<400> SEQUENCE: 136

Asn Leu Glu Gly Ile Ser Lys Ser Ile Lys Lys
1 5 10

<210> SEQ ID NO 137
<211> LENGTH: 13
<212> TYPE: PRT
<213> ORGANISM: Pneumocystis jirovecii

<400> SEQUENCE: 137

Ser Val Ala Leu Asn Gln Ile Glu Ser Tyr Asp Asn Leu
1 5 10

<210> SEQ ID NO 138
<211> LENGTH: 8
<212> TYPE: PRT
<213> ORGANISM: Pneumocystis jirovecii

<400> SEQUENCE: 138

Glu Ser Lys Phe Tyr Ser Tyr Asp
1 5

<210> SEQ ID NO 139
<211> LENGTH: 10
<212> TYPE: PRT
<213> ORGANISM: Pneumocystis jirovecii

<400> SEQUENCE: 139

Val Glu Asp Phe Tyr Ser Ile Tyr Tyr Asn
1 5 10

<210> SEQ ID NO 140
<211> LENGTH: 10
<212> TYPE: PRT
<213> ORGANISM: Pneumocystis jirovecii

<400> SEQUENCE: 140

Thr Leu Gly Asp Cys Lys Met Thr Ile Gln
1 5 10

<210> SEQ ID NO 141
<211> LENGTH: 13
<212> TYPE: PRT
<213> ORGANISM: Pneumocystis jirovecii

<400> SEQUENCE: 141

Leu Ser Leu Glu Asp Ala Gln Leu Ala Asn Leu Pro Gly
1 5 10

<210> SEQ ID NO 142
<211> LENGTH: 9
<212> TYPE: PRT
<213> ORGANISM: Pneumocystis jirovecii

<400> SEQUENCE: 142

Asp Met Gln Leu Ser Thr Met Ala Gly
1 5

<210> SEQ ID NO 143
<211> LENGTH: 9
<212> TYPE: PRT
<213> ORGANISM: Pneumocystis jirovecii

<400> SEQUENCE: 143

Thr Met Arg Leu Ile Thr Asn Leu Gln
1 5

<210> SEQ ID NO 144
<211> LENGTH: 12
<212> TYPE: PRT
<213> ORGANISM: Pneumocystis jirovecii

<400> SEQUENCE: 144

Leu Gly Arg Leu Ala Ser Val Val Ala Lys Gln Leu
1 5 10

<210> SEQ ID NO 145
<211> LENGTH: 10
<212> TYPE: PRT
<213> ORGANISM: Pneumocystis jirovecii

<400> SEQUENCE: 145

Glu Lys Leu Gln Arg Leu Ala Gln Leu Ala
1 5 10

<210> SEQ ID NO 146
<211> LENGTH: 7
<212> TYPE: PRT
<213> ORGANISM: Pneumocystis jirovecii

<400> SEQUENCE: 146

Ser Tyr Asn Ala Arg Asp Val
1 5

<210> SEQ ID NO 147
<211> LENGTH: 8
<212> TYPE: PRT
<213> ORGANISM: Pneumocystis jirovecii

<400> SEQUENCE: 147

Met Ile Asp Asn Ser Ala Pro Leu
1 5

<210> SEQ ID NO 148
<211> LENGTH: 11
<212> TYPE: PRT
<213> ORGANISM: Pneumocystis jirovecii

<400> SEQUENCE: 148

Ser Val Asn Glu Glu Tyr Arg Phe Glu Lys Leu
1               5                   10

<210> SEQ ID NO 149
<211> LENGTH: 14
<212> TYPE: PRT
<213> ORGANISM: Pneumocystis jirovecii

<400> SEQUENCE: 149

Asn Ile Ala Leu Lys Arg Thr Ile Asn Leu Gly Lys Lys Gln
1               5                   10

<210> SEQ ID NO 150
<211> LENGTH: 10
<212> TYPE: PRT
<213> ORGANISM: Pneumocystis jirovecii

<400> SEQUENCE: 150

Tyr Thr Pro Met Met Val Ala Lys Glu Pro
1               5                   10

<210> SEQ ID NO 151
<211> LENGTH: 10
<212> TYPE: PRT
<213> ORGANISM: Pneumocystis jirovecii

<400> SEQUENCE: 151

Val Thr Arg Asn Ala Glu Lys Lys Gln Val
1               5                   10

<210> SEQ ID NO 152
<211> LENGTH: 15
<212> TYPE: PRT
<213> ORGANISM: Pneumocystis jirovecii

<400> SEQUENCE: 152

Arg His Glu His Tyr Leu Ala Ser His Ala Gly Ile Arg Glu Gly
1               5                   10                  15

<210> SEQ ID NO 153
<211> LENGTH: 8
<212> TYPE: PRT
<213> ORGANISM: Pneumocystis jirovecii

<400> SEQUENCE: 153

Glu Ala Val Glu Gly Ile Lys Lys
1               5

<210> SEQ ID NO 154
<211> LENGTH: 10
<212> TYPE: PRT
<213> ORGANISM: Pneumocystis jirovecii

<400> SEQUENCE: 154

Val Phe Arg Ala Ser Arg Thr Gly Gln Leu
1               5                   10

<210> SEQ ID NO 155
<211> LENGTH: 8

<212> TYPE: PRT
<213> ORGANISM: Pneumocystis jirovecii

<400> SEQUENCE: 155

Thr Ser Tyr Ser Val Gln Phe Leu
1 5

<210> SEQ ID NO 156
<211> LENGTH: 11
<212> TYPE: PRT
<213> ORGANISM: Pneumocystis jirovecii

<400> SEQUENCE: 156

Ile Lys Pro Gly Ala Val Val Ile Asp Val Gly
1 5 10

<210> SEQ ID NO 157
<211> LENGTH: 14
<212> TYPE: PRT
<213> ORGANISM: Pneumocystis jirovecii

<400> SEQUENCE: 157

Gly Val Ala Pro Lys Gly Cys Lys Lys Val Asn Asp Val Leu
1 5 10

<210> SEQ ID NO 158
<211> LENGTH: 10
<212> TYPE: PRT
<213> ORGANISM: Pneumocystis jirovecii

<400> SEQUENCE: 158

Ala Ala Lys Asn Thr Ser Lys Pro Gly Glu
1 5 10

<210> SEQ ID NO 159
<211> LENGTH: 13
<212> TYPE: PRT
<213> ORGANISM: Pneumocystis jirovecii

<400> SEQUENCE: 159

Asp Arg Ala His Arg Ile Gly Gln Lys Asn Val Val Asn
1 5 10

<210> SEQ ID NO 160
<211> LENGTH: 6
<212> TYPE: PRT
<213> ORGANISM: Pneumocystis jirovecii

<400> SEQUENCE: 160

Arg Lys Ala Trp Leu Asn
1 5

<210> SEQ ID NO 161
<211> LENGTH: 15
<212> TYPE: PRT
<213> ORGANISM: Pneumocystis jirovecii

<400> SEQUENCE: 161

Gly Arg Leu Val Ser Leu Lys Asp Thr Leu Arg Ser Phe Lys Glu
1 5 10 15

<210> SEQ ID NO 162
<211> LENGTH: 15
<212> TYPE: PRT
<213> ORGANISM: Pneumocystis jirovecii

<400> SEQUENCE: 162

Glu Ala Asp Lys Leu Thr Val Glu Arg Ala Arg Lys Leu Gln Arg
1 5 10 15

<210> SEQ ID NO 163
<211> LENGTH: 8
<212> TYPE: PRT
<213> ORGANISM: Pneumocystis jirovecii

<400> SEQUENCE: 163

Ala Asn Ile Glu Ala Ala Lys His
1 5

<210> SEQ ID NO 164
<211> LENGTH: 15
<212> TYPE: PRT
<213> ORGANISM: Pneumocystis jirovecii

<400> SEQUENCE: 164

Pro Gly Ala Arg Ala Arg Val Ala Leu Thr Gly Leu Thr Val Ala
1 5 10 15

<210> SEQ ID NO 165
<211> LENGTH: 15
<212> TYPE: PRT
<213> ORGANISM: Pneumocystis jirovecii

<400> SEQUENCE: 165

Thr Asp Met Gly Gly Met Gln Glu Arg Ile Thr Thr Thr Lys Lys
1 5 10 15

<210> SEQ ID NO 166
<211> LENGTH: 15
<212> TYPE: PRT
<213> ORGANISM: Pneumocystis jirovecii

<400> SEQUENCE: 166

His Met Gly Glu Arg Thr Val Arg Thr Ile Ala Met Asp Gly Thr
1 5 10 15

<210> SEQ ID NO 167
<211> LENGTH: 15
<212> TYPE: PRT
<213> ORGANISM: Pneumocystis jirovecii

<400> SEQUENCE: 167

Ser Glu Val Ser Ala Leu Leu Gly Arg Ile Pro Ser Ala Val Gly
1 5 10 15

<210> SEQ ID NO 168
<211> LENGTH: 7
<212> TYPE: PRT
<213> ORGANISM: Pneumocystis jirovecii

<400> SEQUENCE: 168

Gln Gln Met Leu Gln Glu Tyr
1 5

<210> SEQ ID NO 169
<211> LENGTH: 13
<212> TYPE: PRT
<213> ORGANISM: Pneumocystis jirovecii

<400> SEQUENCE: 169

Val Gln Phe Ile Leu Gln Ser Tyr Lys Ser Leu Gln Asp
1 5 10

<210> SEQ ID NO 170
<211> LENGTH: 15
<212> TYPE: PRT
<213> ORGANISM: Pneumocystis jirovecii

<400> SEQUENCE: 170

Gly Ala Arg Ala Arg Val Ala Leu Thr Gly Leu Thr Val Ala Glu
1 5 10 15

<210> SEQ ID NO 171
<211> LENGTH: 15
<212> TYPE: PRT
<213> ORGANISM: Pneumocystis jirovecii

<400> SEQUENCE: 171

Phe Gly Gln Met Asn Glu Pro Pro Gly Ala Arg Ala Arg Val Ala
1 5 10 15

<210> SEQ ID NO 172
<211> LENGTH: 15
<212> TYPE: PRT
<213> ORGANISM: Pneumocystis jirovecii

<400> SEQUENCE: 172

Lys Leu Thr Val Glu Arg Ala Arg Lys Leu Gln Arg Phe Met Ser
1 5 10 15

<210> SEQ ID NO 173
<211> LENGTH: 15
<212> TYPE: PRT
<213> ORGANISM: Pneumocystis jirovecii

<400> SEQUENCE: 173

Asp Leu Tyr His Glu Met Ile Gln Thr Gly Val Ile Lys Leu Asp
1 5 10 15

<210> SEQ ID NO 174
<211> LENGTH: 15
<212> TYPE: PRT
<213> ORGANISM: Pneumocystis jirovecii

<400> SEQUENCE: 174

Thr Lys Lys Gly Ser Ile Thr Ser Ile Gln Ala Val Tyr Val Pro
1 5 10 15

<210> SEQ ID NO 175
<211> LENGTH: 8
<212> TYPE: PRT
<213> ORGANISM: Pneumocystis jirovecii

<400> SEQUENCE: 175

Lys Asp Glu Leu Lys Arg Lys His
1 5

<210> SEQ ID NO 176
<211> LENGTH: 13
<212> TYPE: PRT
<213> ORGANISM: Pneumocystis jirovecii

<400> SEQUENCE: 176

Lys Asn His Asn Tyr Ser Tyr Ile Ser Glu His Ser Pro

-continued 1 5 10

<210> SEQ ID NO 177
<211> LENGTH: 11
<212> TYPE: PRT
<213> ORGANISM: Pneumocystis jirovecii

<400> SEQUENCE: 177

Thr Leu Val Glu Ala Tyr Lys Val Tyr Arg Lys
1 5 10

<210> SEQ ID NO 178
<211> LENGTH: 7
<212> TYPE: PRT
<213> ORGANISM: Pneumocystis jirovecii

<400> SEQUENCE: 178

Gly Pro Lys Lys Ile Glu Val
1 5

<210> SEQ ID NO 179
<211> LENGTH: 6
<212> TYPE: PRT
<213> ORGANISM: Pneumocystis jirovecii

<400> SEQUENCE: 179

Met Thr Gly Ile Tyr Leu
1 5

<210> SEQ ID NO 180
<211> LENGTH: 5
<212> TYPE: PRT
<213> ORGANISM: Pneumocystis jirovecii

<400> SEQUENCE: 180

Met Ala Gly Ile Tyr
1 5

<210> SEQ ID NO 181
<211> LENGTH: 12
<212> TYPE: PRT
<213> ORGANISM: Pneumocystis jirovecii

<400> SEQUENCE: 181

Thr Phe Phe Phe Phe Ile Ile Glu Leu Ile Val Leu
1 5 10

<210> SEQ ID NO 182
<211> LENGTH: 14
<212> TYPE: PRT
<213> ORGANISM: Pneumocystis jirovecii

<400> SEQUENCE: 182

Tyr Glu Trp Cys Glu Pro Thr Thr Phe Glu Thr Ser Gly Tyr
1 5 10

<210> SEQ ID NO 183
<211> LENGTH: 6
<212> TYPE: PRT
<213> ORGANISM: Pneumocystis jirovecii

<400> SEQUENCE: 183

Gln Gln Thr Met Gln Thr
1 5

<210> SEQ ID NO 184
<211> LENGTH: 6
<212> TYPE: PRT
<213> ORGANISM: Pneumocystis jirovecii

<400> SEQUENCE: 184

Met Lys Thr Leu Lys Glu
1 5

<210> SEQ ID NO 185
<211> LENGTH: 14
<212> TYPE: PRT
<213> ORGANISM: Pneumocystis jirovecii

<400> SEQUENCE: 185

Cys Met Asn Leu Phe Ala Lys Asn Gly Val Tyr Val Ile Leu
1 5 10

<210> SEQ ID NO 186
<211> LENGTH: 15
<212> TYPE: PRT
<213> ORGANISM: Pneumocystis jirovecii

<400> SEQUENCE: 186

Cys Met Asn Leu Phe Ala Lys Asn Gly Val Tyr Val Ile Leu Asp
1 5 10 15

<210> SEQ ID NO 187
<211> LENGTH: 7
<212> TYPE: PRT
<213> ORGANISM: Pneumocystis jirovecii

<400> SEQUENCE: 187

Gly Pro Lys Lys Ile Glu Val
1 5

<210> SEQ ID NO 188
<211> LENGTH: 7
<212> TYPE: PRT
<213> ORGANISM: Pneumocystis jirovecii

<400> SEQUENCE: 188

Asp Ser Val Gln Leu Leu Ala
1 5

<210> SEQ ID NO 189
<211> LENGTH: 11
<212> TYPE: PRT
<213> ORGANISM: Pneumocystis jirovecii

<400> SEQUENCE: 189

Asn Lys Leu Gln Arg Met Phe Gln Asp Ile Gly
1 5 10

<210> SEQ ID NO 190
<211> LENGTH: 7
<212> TYPE: PRT
<213> ORGANISM: Pneumocystis jirovecii

<400> SEQUENCE: 190

Val Leu Pro Arg Gln Leu Gln
1 5

<210> SEQ ID NO 191

<211> LENGTH: 5
<212> TYPE: PRT
<213> ORGANISM: Pneumocystis jirovecii

<400> SEQUENCE: 191

Asp Leu Asn His Asp
1 5

<210> SEQ ID NO 192
<211> LENGTH: 7
<212> TYPE: PRT
<213> ORGANISM: Pneumocystis jirovecii

<400> SEQUENCE: 192

Pro Glu Leu Asn Gln Asp Ala
1 5

<210> SEQ ID NO 193
<211> LENGTH: 11
<212> TYPE: PRT
<213> ORGANISM: Pneumocystis jirovecii

<400> SEQUENCE: 193

Arg Asp Thr Lys Ala Tyr Ile Arg His Lys His
1 5 10

<210> SEQ ID NO 194
<211> LENGTH: 11
<212> TYPE: PRT
<213> ORGANISM: Pneumocystis jirovecii

<400> SEQUENCE: 194

Ile Leu Asp Leu Ser Glu Pro Arg Asn Ser Ile
1 5 10

<210> SEQ ID NO 195
<211> LENGTH: 10
<212> TYPE: PRT
<213> ORGANISM: Pneumocystis jirovecii

<400> SEQUENCE: 195

Val Asp Pro Leu Ala Asn Ser Arg Ala Cys
1 5 10

<210> SEQ ID NO 196
<211> LENGTH: 9
<212> TYPE: PRT
<213> ORGANISM: Pneumocystis jirovecii

<400> SEQUENCE: 196

Phe Phe Val Lys Gly Val Ala Tyr Gln
1 5

<210> SEQ ID NO 197
<211> LENGTH: 7
<212> TYPE: PRT
<213> ORGANISM: Pneumocystis jirovecii

<400> SEQUENCE: 197

Glu Arg Phe Tyr Ile Arg Gly
1 5

<210> SEQ ID NO 198
<211> LENGTH: 11
<212> TYPE: PRT

<213> ORGANISM: Pneumocystis jirovecii

<400> SEQUENCE: 198

Val Lys Ala Ala Ile Arg Asp Thr Lys Ala Tyr
1 5 10

<210> SEQ ID NO 199
<211> LENGTH: 7
<212> TYPE: PRT
<213> ORGANISM: Pneumocystis jirovecii

<400> SEQUENCE: 199

Gln Val His Pro Ile Val Ile
1 5

<210> SEQ ID NO 200
<211> LENGTH: 12
<212> TYPE: PRT
<213> ORGANISM: Pneumocystis jirovecii

<400> SEQUENCE: 200

Leu Gly Ile Asn Thr Val Arg Val Tyr Thr Ile Asp
1 5 10

<210> SEQ ID NO 201
<211> LENGTH: 5
<212> TYPE: PRT
<213> ORGANISM: Pneumocystis jirovecii

<400> SEQUENCE: 201

Glu Asn Arg Leu Gln
1 5

<210> SEQ ID NO 202
<211> LENGTH: 6
<212> TYPE: PRT
<213> ORGANISM: Pneumocystis jirovecii

<400> SEQUENCE: 202

Tyr Cys Met Asn Leu Phe
1 5

<210> SEQ ID NO 203
<211> LENGTH: 6
<212> TYPE: PRT
<213> ORGANISM: Pneumocystis jirovecii

<400> SEQUENCE: 203

Leu Ile Ala Thr Leu Ser
1 5

<210> SEQ ID NO 204
<211> LENGTH: 7
<212> TYPE: PRT
<213> ORGANISM: Pneumocystis jirovecii

<400> SEQUENCE: 204

Ile Ile Tyr Ser Leu Phe Leu
1 5

<210> SEQ ID NO 205
<211> LENGTH: 6
<212> TYPE: PRT
<213> ORGANISM: Pneumocystis jirovecii

<400> SEQUENCE: 205

Ile Tyr Ala Leu Phe Leu
1 5

<210> SEQ ID NO 206
<211> LENGTH: 14
<212> TYPE: PRT
<213> ORGANISM: Pneumocystis jirovecii

<400> SEQUENCE: 206

Cys Met Asn Leu Phe Ala Lys Asn Gly Val Tyr Val Ile Leu
1 5 10

<210> SEQ ID NO 207
<211> LENGTH: 9
<212> TYPE: PRT
<213> ORGANISM: Pneumocystis jirovecii

<400> SEQUENCE: 207

Ala Met Arg Glu Ala Gly Ile Tyr Val
1 5

<210> SEQ ID NO 208
<211> LENGTH: 11
<212> TYPE: PRT
<213> ORGANISM: Pneumocystis jirovecii

<400> SEQUENCE: 208

Asn Ser Tyr Gly Leu Val Ile Ile His Asn Asp
1 5 10

<210> SEQ ID NO 209
<211> LENGTH: 8
<212> TYPE: PRT
<213> ORGANISM: Pneumocystis jirovecii

<400> SEQUENCE: 209

Asn Lys Val Tyr Leu Asn Gln Leu
1 5

<210> SEQ ID NO 210
<211> LENGTH: 9
<212> TYPE: PRT
<213> ORGANISM: Pneumocystis jirovecii

<400> SEQUENCE: 210

Val Ser Asp Glu Asp Thr Lys Gly Ile
1 5

<210> SEQ ID NO 211
<211> LENGTH: 6
<212> TYPE: PRT
<213> ORGANISM: Pneumocystis jirovecii

<400> SEQUENCE: 211

Val Ile Asn Asp Glu Asp
1 5

<210> SEQ ID NO 212
<211> LENGTH: 5
<212> TYPE: PRT
<213> ORGANISM: Pneumocystis jirovecii

<400> SEQUENCE: 212

Trp Arg Val Arg Val
1 5

<210> SEQ ID NO 213
<211> LENGTH: 8
<212> TYPE: PRT
<213> ORGANISM: Pneumocystis jirovecii

<400> SEQUENCE: 213

Val Ala Trp Arg His Arg Leu Lys
1 5

<210> SEQ ID NO 214
<211> LENGTH: 10
<212> TYPE: PRT
<213> ORGANISM: Pneumocystis jirovecii

<400> SEQUENCE: 214

Ser Leu Leu Tyr Asn Asp Leu Ser Arg Lys
1 5 10

<210> SEQ ID NO 215
<211> LENGTH: 7
<212> TYPE: PRT
<213> ORGANISM: Pneumocystis jirovecii

<400> SEQUENCE: 215

Glu Lys Asn Ile Pro Val Glu
1 5

<210> SEQ ID NO 216
<211> LENGTH: 5
<212> TYPE: PRT
<213> ORGANISM: Pneumocystis jirovecii

<400> SEQUENCE: 216

Trp Arg Thr Ala Phe
1 5

<210> SEQ ID NO 217
<211> LENGTH: 6
<212> TYPE: PRT
<213> ORGANISM: Pneumocystis jirovecii

<400> SEQUENCE: 217

Trp Arg Thr Asp Phe His
1 5

<210> SEQ ID NO 218
<211> LENGTH: 6
<212> TYPE: PRT
<213> ORGANISM: Pneumocystis jirovecii

<400> SEQUENCE: 218

Leu Arg Ile Lys Gln Phe
1 5

<210> SEQ ID NO 219
<211> LENGTH: 5
<212> TYPE: PRT
<213> ORGANISM: Pneumocystis jirovecii

<400> SEQUENCE: 219

Phe Ala Gly Phe Trp
1 5

<210> SEQ ID NO 220
<211> LENGTH: 6
<212> TYPE: PRT
<213> ORGANISM: Pneumocystis jirovecii

<400> SEQUENCE: 220

Leu Val Val Thr Phe Asn
1 5

<210> SEQ ID NO 221
<211> LENGTH: 9
<212> TYPE: PRT
<213> ORGANISM: Pneumocystis jirovecii

<400> SEQUENCE: 221

Leu Leu Val Thr Gly Ile Lys Pro Leu
1 5

<210> SEQ ID NO 222
<211> LENGTH: 8
<212> TYPE: PRT
<213> ORGANISM: Pneumocystis jirovecii

<400> SEQUENCE: 222

Phe Phe Phe Leu Leu Gly Ile Val
1 5

<210> SEQ ID NO 223
<211> LENGTH: 5
<212> TYPE: PRT
<213> ORGANISM: Pneumocystis jirovecii

<400> SEQUENCE: 223

Trp Arg Val Arg Val
1 5

<210> SEQ ID NO 224
<211> LENGTH: 8
<212> TYPE: PRT
<213> ORGANISM: Pneumocystis jirovecii

<400> SEQUENCE: 224

Val Ala Trp Arg His Arg Leu Lys
1 5

<210> SEQ ID NO 225
<211> LENGTH: 8
<212> TYPE: PRT
<213> ORGANISM: Pneumocystis jirovecii

<400> SEQUENCE: 225

Ile Ile Ile Thr Leu Leu Ile Ser
1 5

<210> SEQ ID NO 226
<211> LENGTH: 16
<212> TYPE: PRT
<213> ORGANISM: Pneumocystis jirovecii

<400> SEQUENCE: 226

Leu Ser Arg Leu Met Ser Gln Met Ser Lys Ile Ile Ser Asn Leu Lys
1 5 10 15

<210> SEQ ID NO 227
<211> LENGTH: 6
<212> TYPE: PRT
<213> ORGANISM: Pneumocystis jirovecii

<400> SEQUENCE: 227

Tyr Ile Val Thr Glu Tyr
1 5

<210> SEQ ID NO 228
<211> LENGTH: 7
<212> TYPE: PRT
<213> ORGANISM: Pneumocystis jirovecii

<400> SEQUENCE: 228

Ser Glu Leu Asp Met Thr Ile
1 5

<210> SEQ ID NO 229
<211> LENGTH: 6
<212> TYPE: PRT
<213> ORGANISM: Pneumocystis jirovecii

<400> SEQUENCE: 229

Phe Leu Ser Ala Leu Asp
1 5

<210> SEQ ID NO 230
<211> LENGTH: 7
<212> TYPE: PRT
<213> ORGANISM: Pneumocystis jirovecii

<400> SEQUENCE: 230

Val Pro Leu Gly Ile Leu Ser
1 5

<210> SEQ ID NO 231
<211> LENGTH: 6
<212> TYPE: PRT
<213> ORGANISM: Pneumocystis jirovecii

<400> SEQUENCE: 231

Phe His Tyr Gln Val Pro
1 5

<210> SEQ ID NO 232
<211> LENGTH: 12
<212> TYPE: PRT
<213> ORGANISM: Pneumocystis jirovecii

<400> SEQUENCE: 232

Leu Ser Asp Ile His Asn Arg Asn Pro Ser Val Val
1 5 10

IDENTIFICATION OF PNEUMOCYSTIS ANTIGENS AND USES THEREOF

CROSS REFERENCE TO RELATED APPLICATIONS

This is the U.S. National Stage of International Application No. PCT/US2015/021573, filed Mar. 19, 2015, published in English under PCT Article 21(2), which claims the benefit of U.S. Provisional Application No. 61/968,802, filed Mar. 21, 2014, which is herein incorporated by reference in its entirety.

ACKNOWLEDGMENT OF GOVERNMENT SUPPORT

This invention was made with government support under grant numbers HL062052 and HL061271 awarded by the National Institutes of Health. The government has certain rights in the invention.

FIELD

This disclosure concerns a method for *Pneumocystis* antigen discovery, and uses of the identified *Pneumocystis* antigens, such as for the treatment and diagnosis of *Pneumocystis* pneumonia.

BACKGROUND

*Pneumocystis* pneumonia (PCP) is a significant cause of mortality and morbidity in immunocompromised patients. There are limited alternative therapeutic choices to trimethoprim-sulfamethoxazole (TMP-SMX). Antibody responses to surface proteins have been associated with protection from *Pneumocystis* pneumonia using both active and passive immunization approaches (Zheng et al., *J Clin Invest* 108:1469-1474, 2001; Zheng et al., *J Clin Invest* 115:3536-3544, 2005; Empey et al., Infect Immun 72:6211-6220, 2004; Wells et al., *Infect Immun* 74:2446-2448, 2006; Gigliotti et al., *Infect Immun* 70:1069-1074, 2002). These data suggest that antibody responses raised against surface epitopes can provide protection against *Pneumocystis* pneumonia potentially by enhancing opsonic phagocytosis or through activation of complement (Wells et al., *Infect Immun* 74:390-393, 2006; Steele et al., *J Exp Med* 198: 1677-1688, 2003). A limitation of antigen discovery for this pathogen is the fact that *Pneumocystis* (*Pneumocystis*) cannot be cultured in vitro.

SUMMARY

Methods of eliciting an immune response against *Pneumocystis jirovecii* in a subject, immunizing a subject against *pneumocystis* pneumonia, and treating a subject diagnosed with *pneumocystis* pneumonia are provided by the present disclosure. In some embodiments, the method includes administering to the subject a Meu10, GSC-1, Ght5, Erg6, ATP2, Gas4 or Mfs1 protein or immunogenic fragment; administering to the subject a nucleic acid molecule encoding a Meu10, GSC-1, Ght5, Erg6, ATP2, Gas4 or Mfs1 protein or immunogenic fragment; administering to the subject a *Pneumocystis jirovecii* protein homologous to any one of the Meu10, GSC-1, Ght5, Erg6, ATP2, Gas4 or Mfs1 proteins disclosed herein, or an immunogenic fragment thereof; or administering to the subject a nucleic acid molecule encoding a *Pneumocystis jirovecii* protein homologous to any one of the Meu10, GSC-1, Ght5, Erg6, ATP2, Gas4 or Mfs1 proteins disclosed herein, or an immunogenic fragment thereof.

Further provided is a method of treating a subject diagnosed with *pneumocystis* pneumonia by administering to the subject a monoclonal antibody specific for a Meu10, GSC-1, Ght5, Erg6, ATP2, Gas4 or Mfs1 protein disclosed herein.

Methods of diagnosing a subject as having *pneumocystis* pneumonia are further provided. In some embodiments, the method includes contacting a sample from the subject with a monoclonal antibody specific for a Meu10, GSC-1, Ght5, Erg6, ATP2, Gas4 or Mfs1 protein or immunogenic fragment; or a monoclonal antibody specific for a *Pneumocystis jirovecii* protein homologous to any one of the Meu10, GSC-1, Ght5, Erg6, ATP2, Gas4 or Mfs1 proteins disclosed herein, or an immunogenic fragment thereof; detecting binding of the antibody to the sample; and diagnosing the subject as having *pneumocystis* pneumonia when an increase in binding of the antibody to the sample, as compared to binding of the antibody to a control sample, is detected. In other embodiments, the method includes performing RT-PCR on a sample obtained from the subject using Meu10- and GSC-1-specific primers to amplify Meu10 and GSC-1 nucleic acid present in the sample; detecting the presence or absence of Meu10 and GSC-1 amplification products; and diagnosing the *Pneumocystis jirovecii* infection in the subject if Meu10 and/or GSC-1 amplification products are detected.

The foregoing and other objects, features, and advantages of the invention will become more apparent from the following detailed description, which proceeds with reference to the accompanying figures.

BRIEF DESCRIPTION OF THE DRAWINGS

FIGS. 1A-1B: Identification of *Pneumocystis* surface peptides. (FIG. 1A) FPEK*IEVENLYK (SEQ ID NO: 105) is an exposed portion of several *P. murina* major surface glycoproteins such as PENG_02417 and PNEG_00001. The tandem mass spectrum of a doubly charged peptide precursor ion at m/z 925.1 is shown. (FIG. 1B) HGQIEVTCAK*SGIYENSLWYIEDNS (SEQ ID NO: 106), a peptide expressed on the exposed portion of transmembrane *P. murina* gene PNEG_00837 (as predicted by TMHMM analysis) was searched against the *P. murina* protein sequence database using the in-house search engine Biomarks3.3. Modification of lysine (K*) by sulfo-NHS-LC-biotin was unambiguously determined by the series of b and y ions on the tandem mass spectrum. The arrow indicates the site of labeling. The amino acid sequence of *P. murina* hypothetical protein PNEG_00837 (SEQ ID NO: 107) is also shown.

(FIG. 3A) Recombinant myc-tagged Meu10 protein identified by SDS-PAGE and Western blotting in transfected 293 cell lysate. (FIG. 3B) Anti-*Pneumocystis* (PC) serum recognizes Meu10 lysate by ELISA compared to naïve serum (top panel, p=0.0009). Further normalization of the data to non-transfected 293 lysate (background) demonstrated that anti-*Pneumocystis* serum recognizes Meu10 at a greater optical density (O.D.) than naïve serum (bottom panel, p=0.024).

FIG. 19: Mice immunized with recombinant GSC-1 had a reduction in cyst-specific markers. Expression of serine protease (SP), a troph marker, and Arp9, a cyst-specific marker, was measured using qRT-PCR. GSC-1 protein immunization reduced the expression of Arp9 (* $p<0.05$ by one-way ANOVA with Tukey's multiple comparisons). SP expression was unchanged.

SEQUENCE LISTING

Figure 1A:
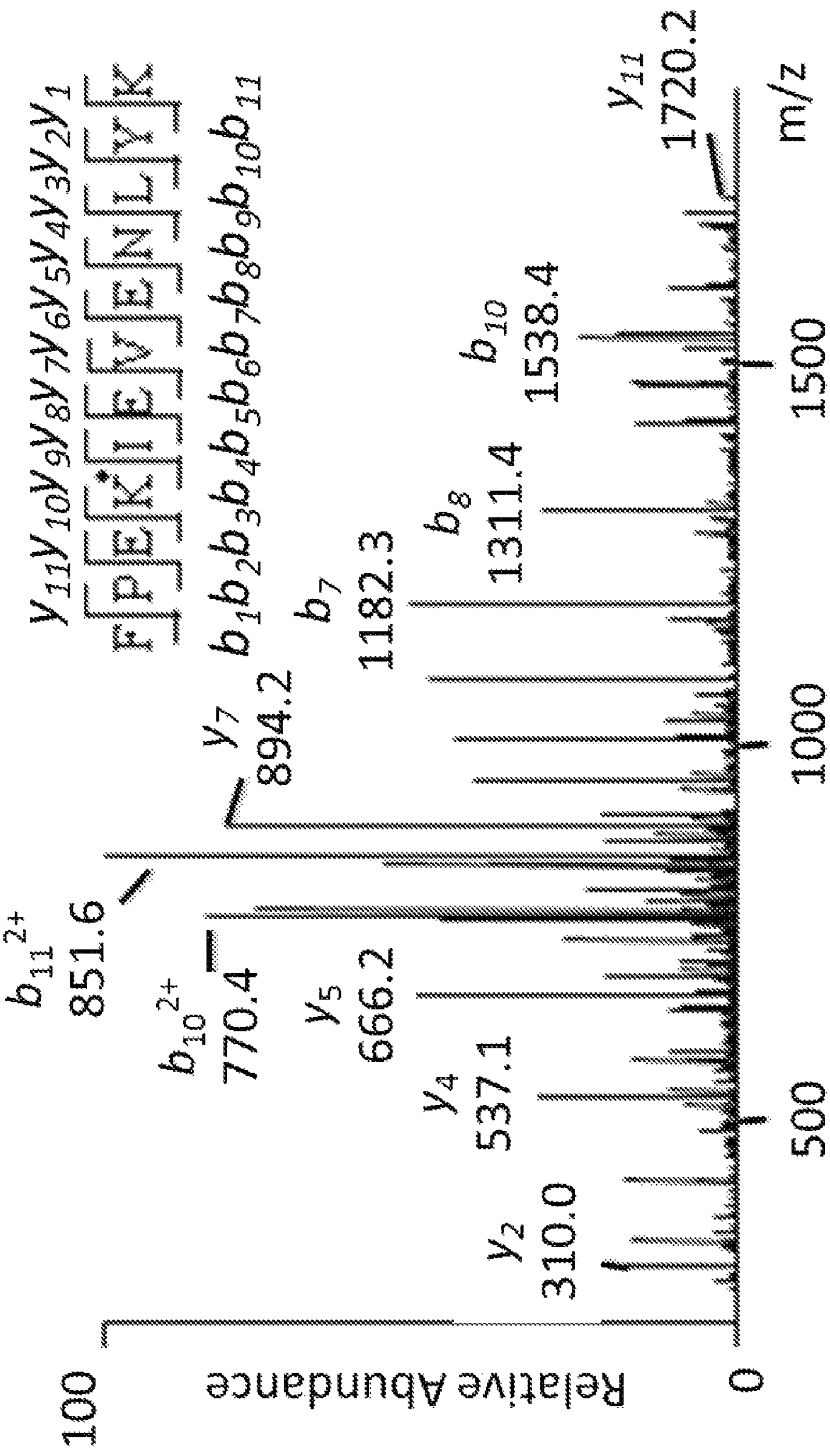

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Sep. 14, 2016, 105 KB, which is incorporated by reference herein. In the accompanying sequence listing:

SEQ ID NO: 1 is the amino acid sequence of the *S. pombe* Ght5 protein deposited under GENBANK™ Accession No. NP_587740.1.

SEQ ID NO: 2 is the amino acid sequence of the *P. carinii* GSC-1 protein deposited under GENBANK™ Accession No. AF191096.1.

SEQ ID NO: 3 is the amino acid sequence of the *S. pombe* Meu10 protein deposited under GENBANK™ Accession No. NP_588357.1.

SEQ ID NO: 4 is the amino acid sequence of the *S. pombe* Erg6 protein deposited under GENBANK™ Accession No. NP_595787.1.

SEQ ID NO: 5 is the amino acid sequence of the *S. pombe* ATP2 protein deposited under GENBANK™ Accession No. NP_593151.1.

SEQ ID NO: 6 is the amino acid sequence of the *S. cerevisiae* Gas4 protein deposited under GENBANK™ Accession No. NP_014509.1.

SEQ ID NO: 7 is the amino acid sequence of the *S. pombe* Gas4 protein deposited under GENBANK™ Accession No. NP_596746.1.

SEQ ID NO: 8 is the amino acid sequence of the *S. pombe* Mfs1 protein deposited under GENBANK™ Accession No. NP_596009.1.

SEQ ID NOs: 9-18 are *S. pombe* Ght5 peptide sequences.

SEQ ID NOs: 19-28 are *P. carinii* GSC-1 peptide sequences.

SEQ ID NOs: 29-38 are *S. pombe* Meu10 peptide sequences.

SEQ ID NOs: 39-48 are *S. pombe* Erg6 peptide sequences.

SEQ ID NOs: 49-62 are *S. pombe* ATP2peptide sequences.

SEQ ID NOs: 63-76 are *S. cerevisiae* Gas4 peptide sequences.

SEQ ID NOs: 77-90 are *S. pombe* Gas4 peptide sequences.

SEQ ID NOs: 91-104 are *S. pombe* Mfs1 peptide sequences.

SEQ ID NO: 105 is the amino acid sequence of a *P. murina* major surface glycoprotein peptide.

SEQ ID NO: 106 is the amino acid sequence of a peptide expressed on the exposed portion of transmembrane *P. murina* gene PNEG_00837.

SEQ ID NO: 107 is the amino acid sequence of a peptide putatively expressed on the outside of the *P. murina* glycosyltransferase family 39 protein.

SEQ ID NO: 108 is a recombinant Meu10 nucleic acid sequence having the following features:

nucleotides 1-18—restriction enzyme/Gateway sites;

nucleotides 19-78—artificial leader sequence;

nucleotides 79-1137—Meu10 ectodomain coding sequence; and nucleotides 1138-1245—histidine and myc tags.

SEQ ID NO: 109 is a recombinant Meu10 ectodomain amino acid sequence having the following features:

residues 1-21—artificial leader sequence;

residues 22-373—Meu10 ectodomain sequence; and residues 374-408—histidine and myc tags.

SEQ ID NO: 110 is a recombinant GSC-1 ectodomain nucleic acid sequence having the following features:

nucleotides 1-10—restriction enzyme/Gateway sites;

nucleotides 11-73—artificial leader sequence;

nucleotides 74-1822—GSC-1 ectodomain coding sequence; and nucleotides 1823-1930—histidine and myc tags.

SEQ ID NO: 111 is a recombinant GSC-1 ectodomain amino acid sequence having the following features:

residues 1-21—artificial leader sequence;

residues 22-606—GSC-1 ectodomain sequence; and residues 607-641—histidine and myc tags.

SEQ ID NOs: 112-125 are *P. jirovecii* Ght5 peptide sequences.

SEQ ID NOs: 126-135 are *P. jirovecii* GSC1 peptide sequences.

SEQ ID NOs: 136-148 are *P. jirovecii* Meu10 peptide sequences.

SEQ ID NOs: 149-159 are *P. jirovecii* Erg6 peptide sequences.

SEQ ID NOs: 160-174 are *P. jirovecii* ATP2 peptide sequences.

SEQ ID NOs: 175-211 are *P. jirovecii* Gas4 peptide sequences.

SEQ ID NOs: 212-232 are *P. jirovecii* Mfs1 peptide sequences.

DETAILED DESCRIPTION

I. Abbreviations

BAL bronchoalveolar lavage
CMV cytomegalovirus
ELISA enzyme linked immunosorbent assay
HRP horseradish peroxidase
IFN interferon
GPI glycophosphatidylinositol
IL interleukin
LC-MS liquid chromatography tandem mass spectroscopy
MHC major histocompatibility complex
MS mass spectroscopy
MSG major surface glycoprotein
OVA ovalbumin
PC *Pneumocystis*
PCP *Pneumocystis* pneumonia
qRT-PCR quantitative real-time polymerase chain reaction
rRNA ribosomal ribonucleic acid
Th T helper
TMHMM tied mixture hidden Markov model
WT wild type

II. Terms and Methods

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adjuvant: A substance or vehicle that non-specifically enhances the immune response to an antigen. Adjuvants can include a suspension of minerals (alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants also include biological molecules, such as costimulatory molecules. Exemplary biological adjuvants include IL-2, RANTES, GM-CSF, TNF-α, IFN-γ, G-CSF, LFA-3, CD72, B7-1, B7-2, OX-40L and 41 BBL.

Administration: The introduction of a composition into a subject by a chosen route. For example, if the chosen route is intravenous, the composition is administered by introducing the composition into a vein of the subject. Exemplary routes of administration include, but are not limited to, injection (such as subcutaneous, intramuscular, intradermal, intraperitoneal, and intravenous), oral, intraductal, sublingual, rectal, transdermal, intranasal, vaginal and inhalation routes. In particular embodiments disclosed herein, the route of administration is subcutaneous or intramuscular.

Antibody: A polypeptide ligand comprising at least a light chain or heavy chain immunoglobulin variable region which specifically recognizes and binds an epitope of an antigen. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antibodies include intact immunoglobulins and the variants and portions of antibodies well known in the art, such as Fab fragments, Fab' fragments, $F(ab)'_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook,* 1994-1995 (Pierce Chemical Co., Rockford, Ill.); Kuby, J., *Immunology,* 3rd Ed., W. H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region (the regions are also known as "domains"). References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a murine antibody.

A "humanized" immunoglobulin is an immunoglobulin including a human framework region and one or more complementarity determining regions (CDRs) from a non-human (for example a mouse, rat, or synthetic) immunoglobulin. The non-human immunoglobulin providing the CDRs is termed a "donor," and the human immunoglobulin providing the framework is termed an "acceptor." Generally, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. Humanized immunoglobulins can be constructed by means of genetic engineering (see for example, U.S. Pat. No. 5,585,089).

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. All parts of a human immunoglobulin are substantially identical to corresponding parts of natural human immunoglobulin sequences.

Antigen: A compound, composition, or substance that can stimulate the production of antibodies and/or a CD4+ or CD8+ T cell response in an animal, including compositions that are injected or absorbed into an animal. An antigen reacts with the products of specific humoral or cellular immunity, including those induced by heterologous immunogens. The term "antigen" includes all related antigenic epitopes. "Epitope" or "antigenic determinant" refers to a site on an antigen to which B and/or T cells respond. In some embodiments, T cells respond to the epitope, when the epitope is presented in conjunction with a major histocompatibility complex (MHC) molecule.

Conservative variants: "Conservative" amino acid substitutions are those substitutions that do not substantially affect or decrease an activity or antigenicity of a protein. For example, a protein or peptide can include at most about 1, about 2, about 3, about 4, about 5, about 6, about 7, about 8, about 9 or about 10 conservative substitutions and specifically bind an antibody that binds the original protein or peptide. Specific, non-limiting examples of a conservative substitution include the following examples:

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The term conservative variant also includes the use of a substituted amino acid in place of an unsubstituted parent amino acid. Non-conservative substitutions are those that reduce an activity or antigenicity.

Epitope: An antigenic determinant. These are particular chemical groups or peptide sequences on a molecule that are antigenic, i.e. that elicit a specific immune response. An antibody specifically binds a particular antigenic epitope on a polypeptide.

Fusion protein: A protein generated by expression of a nucleic acid sequence engineered from nucleic acid sequences encoding at least a portion of two different (heterologous) proteins. To create a fusion protein, the nucleic acid sequences must be in the same reading frame and contain no internal stop codons.

Heterologous: Originating from separate genetic sources or species. For example, a polypeptide that is heterologous to *S. pombe* Meu10 originates from a nucleic acid that does not encode *S. pombe* Meu10. In some embodiments, the heterologous amino acid sequence includes an affinity tag, an epitope tag, a fluorescent protein, an enzyme or a carrier protein.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are discussed by Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989, chapters 9 and 11; and Ausubel et al. *Short Protocols in Molecular Biology*, $4^{th}$ ed., John Wiley & Sons, Inc., 1999.

For purposes of the present disclosure, "stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize.

"Specific hybridization" refers to the binding, duplexing, or hybridizing of a molecule only or substantially only to a particular nucleotide sequence when that sequence is present in a complex mixture (for example, total cellular DNA or RNA). Specific hybridization may also occur under conditions of varying stringency.

Immune response: A response of a cell of the immune system, such as a B cell, T cell, monocyte, macrophage, dendritic cell or natural killer cell to a stimulus. In one embodiment, the response is specific for a particular antigen (an "antigen-specific response"), also known as an adaptive immune response. In some embodiments, the adaptive immune response is a T cell response, such as a CD4+ response and/or a CD8+ response. In some embodiments, the adaptive immune response is a B cell response, and results in the production of specific antibodies.

Immunize: To render a subject protected from an infectious disease, such as by vaccination.

Immunogenic composition: In the context of the present disclosure, a composition comprising an antigenic peptide that induces a measurable cytotoxic T lymphocyte (CTL) response against cells expressing the antigen, and/or induces a measurable B cell response (e.g. production of antibodies) against the antigen. For in vitro use, the immunogenic composition may consist of the isolated protein or peptide (s). For in vivo use, the immunogenic composition will typically comprise the protein or peptide(s) in pharmaceutically acceptable carriers, and/or other agents. Any particular antigenic peptide can be readily tested for its ability to induce a CTL or B cell response by art-recognized assays. Immunogenic compositions can include adjuvants, which are well known to one of skill in the art.

Immunogenic fragment: A portion of a protein that is capable of eliciting an immune response, such as a CTL or B cell response. Exemplary immunogenic fragments of the proteins disclosed herein are provided in Table 2, and set forth as SEQ ID NOs: 9-104.

Inhibiting or treating a disease: Inhibiting the full development of a disease or condition, for example, in a subject who is at risk for a disease such as *Pneumocystis* pneumonia. "Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Isolated: An "isolated" biological component (such as a nucleic acid or protein or organelle) has been substantially separated or purified away from other biological components in the cell of the organism in which the component naturally occurs, such as other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes.

Linker: One or more nucleotides or amino acids that serve as a spacer between two molecules, such as between two nucleic acid molecules or two peptides (such as in a fusion protein).

Non-naturally occurring: Not found in nature. This term encompasses single components (such as a single protein or molecule) that are not found in nature, as well as compositions (such as a peptide and a carrier) comprising multiple components, wherein at least one of the components is not found in nature or the components are not found together in nature.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Peptide or polypeptide: Any chain of amino acids regardless of length or post-translational modification (such as glycosylation or phosphorylation). In some embodiments, a polypeptide is between 8 and 100 amino acids in length, including 8 to 50, 8 to 25, 8 to 20, 8 to 15, 12 to 40, 12 to 25, 12 to 20, or 16 to 20 amino acids in length. In particular examples, a *Pneumocystis* surface expressed peptide or polypeptide is 8, 9, 10, 11, 12, 13, 14, 15, 16, 17, 18, 19 or 20 amino acids in length.

A peptide or polypeptide is a series of contiguous amino acid residues from a protein, such as a *P. murina* or *P. jirovecii* protein. In one example, with respect to immunogenic compositions comprising a *P. murina* or *P. jirovecii* surface expressed peptide, the term further refers to variations of these peptides in which there are conservative substitutions of amino acids, so long as the variations do not alter by more than about 20% (such as no more than about 1%, about 5%, or about 10%) the ability of the peptide to produce a B cell response, or, when bound to a MHC class I molecule, to activate cytotoxic T lymphocytes against *P. murina* or *P. jirovecii* expressing the protein. Induction of CTLs using synthetic peptides and CTL cytotoxicity assays are taught in, e.g., U.S. Pat. No. 5,662,907.

A "residue" refers to an amino acid or amino acid mimetic incorporated in a polypeptide by an amide bond or amide bond mimetic.

Peptide, polypeptide or protein modifications: The peptides contemplated herein include synthetic embodiments of the disclosed peptides. In addition, analogs (non-peptide organic molecules), derivatives (chemically functionalized peptide molecules obtained starting with the disclosed peptide sequences) and variants (homologs, orthologs or paralogs) of these proteins can be utilized in the methods described herein. Each polypeptide is comprised of a sequence of amino acids, which may be either L- and/or D-amino acids, naturally occurring and otherwise. Peptides may be modified by a variety of chemical techniques to produce derivatives having essentially the same activity as the unmodified peptides, and optionally having other desirable properties.

Polypeptide modifications also include amino acid substitutions, such as those that alter binding affinity of the polypeptide to MHC molecules. Exemplary amino acid substitutions for altering MHC binding affinity have been described in the art (see, for example, Berzofsky et al., *Nat. Rev. Immunol.* 1(3):209-219, 2001).

Pharmaceutically acceptable carrier: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of proteins and nucleic acids, such as those disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. In some embodiments, the pharmaceutical carrier is sterile, particularly when in an injectable form. In some embodiments, the pharmaceutical carrier is non-naturally occurring.

*Pneumocystis*: A genus of fungi named for a cyst-like multinucleate morphological form that stains strongly with silver and is found together with a uninucleate pleomorphic “trophic” form in alveolar spaces in the lungs of numerous mammalian species. *Pneumocystis* species cannot be grown in culture.

*Pneumocystis jirovecii*: A yeast-like fungus of the genus *Pneumocystis*, and the causative organism of *Pneumocystis* pneumonia in humans.

*Pneumocystis murina*: A species of fungus originally isolated from lab mice.

*Pneumocystis* pneumonia: A disease of immunocompromised individuals, such as HIV-infected patients or bone marrow transplant patients, caused by infection with *Pneumocystis jirovecii.*

Polynucleotide: The term polynucleotide or nucleic acid sequence refers to a polymeric form of nucleotide, usually at least 10 bases in length. The term includes, for example, a recombinant DNA that is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

Probes and primers: A probe comprises an isolated nucleic acid molecule attached to a detectable label or other reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example, in Sambrook et al. (ed.), *Molecular Cloning: A Laboratory Manual,* 2nd ed., vol. 1-3, Cold Spring Harbor Laboratory Press, Cold Spring Harbor, N.Y., 1989 and Ausubel et al. *Short Protocols in Molecular Biology,* 4th ed., John Wiley & Sons, Inc., 1999.

Primers are short nucleic acid molecules, for instance DNA oligonucleotides 10 nucleotides or more in length, for example that hybridize to contiguous complementary nucleotides or a sequence to be amplified. Longer DNA oligonucleotides may be about 12, 15, 18, 20, 25, 30, or 50 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, for example, by the polymerase chain reaction (PCR) or other nucleic-acid amplification methods known in the art. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification; gap filling ligase chain reaction amplification, as disclosed in U.S. Pat. No. 5,427,930; and NASBA™ RNA transcription-free amplification, as disclosed in U.S. Pat. No. 6,025,134.

Methods for preparing and using nucleic acid probes and primers are described, for example, in Sambrook et al. (ed.), *Molecular Cloning: A Laboratory Manual,* 2nd ed., vol. 1-3, Cold Spring Harbor Laboratory Press, Cold Spring Harbor, N.Y., 1989; Ausubel et al. *Short Protocols in Molecular Biology,* 4th ed., John Wiley & Sons, Inc., 1999; and Innis et al. *PCR Protocols, A Guide to Methods and Applications*, Academic Press, Inc., San Diego, Calif., 1990. Amplification primer pairs can be derived from a known sequence, for example, by using computer programs intended for that purpose such as Primer (Version 0.5, © 1991, Whitehead Institute for Biomedical Research, Cambridge, Mass.).

Promoter: A promoter is an array of nucleic acid control sequences that directs transcription of a nucleic acid. A promoter includes necessary nucleic acid sequences near the start site of transcription, such as in the case of a polymerase II type promoter (a TATA element). A promoter also optionally includes distal enhancer or repressor elements which can be located as much as several thousand base pairs from the start site of transcription. Both constitutive and inducible promoters are included (see e.g., Bitter et al., *Methods in Enzymology* 153:516-544, 1987).

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50% of the total peptide or protein content of the preparation. A substantially purified protein is at least 60%, 70%, 80%, 90%, 95% or 98% pure. Thus, in one specific, non-limiting example, a purified protein is 90% free of other proteins or cellular components. The peptides disclosed herein can be purified by any of the means known in the art (see, e.g., *Guide to Protein Purification*, ed. Deutscher, *Meth. Enzymol.* 185, Academic Press, San Diego, 1990; and Scopes, *Protein Purification: Principles and Practice*, Springer Verlag, New York, 1982).

Recombinant: A recombinant nucleic acid or protein is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, e.g., by genetic engineering techniques.

Sample: As used herein, a “sample” or “biological sample” refers to a sample obtained from a subject (such as a human or veterinary subject). In some examples of the methods disclosed herein, the sample is a fluid sample. Fluid samples from a subject include, but are not limited to, bronchoalveolar lavage fluid, sputum, serum, blood, plasma, urine, saliva, cerebral spinal fluid (CSF) or other bodily fluid. Samples can also refer to cell or tissue samples, such as tissues biopsy samples.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a peptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. In addition, Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a peptide are typically characterized by possession of at least about 75%, for example at least about 80%, 90%, 95%, 96%, 97%, 98% or 99% sequence identity counted over the full length alignment with the amino acid sequence of the peptide or a paralog of the peptide using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Subject: Living multi-cellular vertebrate organisms, a category that includes both human and veterinary subjects, including human and non-human mammals.

Synthetic: Produced by artificial means in a laboratory, for example a synthetic peptide can be chemically synthesized in a laboratory.

Therapeutically effective amount: A quantity of a specified agent sufficient to achieve a desired effect in a subject, cell or culture being treated with that agent. In the context of the present disclosure, a therapeutically effective amount of *Pneumocystis* protein or DNA is an amount that causes induction of an immune response, as measured by clinical response (for example increase in a population of immune cells, production of antigen-specific antibodies, or measurable reduction of *Pneumocystis* burden). In one embodiment, a therapeutically effective amount of a *Pneumocystis* peptide or DNA is an amount used to generate an immune response, or to treat *Pneumocystis* pneumonia in a subject.

Unit Dose: A drug or pharmaceutical composition in a single or metered dose form, such as a table, capsule, powder or solution to be administered as a single dose, or multiple preselected doses. In the context of the present disclosure, a composition in unit dose form contains a preselected therapeutic amount of protein, peptide(s) or DNA appropriate for a single dose, or one of multiple preselected metered doses, such as the amount necessary to elicit an immune response against *Pneumocystis*. In some examples, the unit dose is a liquid contained in a sterile vial, or a powder in a sterile vial capable of being reconstituted for administration by introduction of a liquid into the vial. In other examples, the unit dosage form is provided in a syringe suitable for administration, for example injection into a subject.

Vaccine: A preparation of immunogenic material capable of stimulating an immune response, administered for the prevention, amelioration, or treatment of infectious or other types of disease. The immunogenic material may include attenuated or killed microorganisms (such as attenuated viruses), or antigenic proteins, peptides or DNA derived from them. Vaccines may elicit both prophylactic (preventative) and therapeutic responses. Methods of administration vary according to the vaccine, but may include inoculation, ingestion, inhalation or other forms of administration. Inoculations can be delivered by any of a number of routes, including parenteral, such as intravenous, subcutaneous or intramuscular. Vaccines may be administered with an adjuvant to boost the immune response.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Embodiments

Pneumonia due to the fungus *Pneumocystis jirovecii* is a life-threatening infection that occurs in immunocompromised patients. The inability to culture the organism as well as the lack of a sequenced genome has previously hindered antigen discovery that could be useful in developing effective vaccines, therapeutic antibodies and diagnostic methods. A recently described tool that may facilitate antigen discovery for fungi is the use of the specific labeling of fungal cell surface proteins followed by proteomic analysis using liquid chromatography tandem mass spectroscopy (LC-MS) for the study of both the localization and function (Ali and Bergson, *J Biol Chem* 278:51654-51663, 2003) of fungal surface proteins (Qian et al., *Anal Bioanal Chem* 392:439-449, 2008). This approach allows for the characterization of cell surface proteins on living cell surfaces.

Disclosed herein is a method of surface proteomics of *Pneumocystis murina* that reliably detects surface proteins that are conserved in *Pneumocystis jirovecii*. In particular, eight identified *P. murina* surface proteins are described.

Methods of eliciting immune responses against the identified proteins, generating therapeutic antibodies against the identified proteins, as well as diagnostic methods based on the identified peptides are described.

Provided herein are methods of eliciting an immune response against *Pneumocystis jirovecii* in a subject. In some embodiments, the method includes:

administering to the subject a Meu10 protein comprising an amino acid sequence at least 80%, at least 85%, at least 90%, at least 95%, at least 96%, at least 97%, at least 98% or at least 99% identical to residues 22-373 of SEQ ID NO: 109, or one or more immunogenic fragments thereof; or administering to the subject a nucleic acid molecule encoding a Meu10 protein comprising an amino acid sequence at least 80%, at least 85%, at least 90%, at least 95%, at least 96%, at least 97%, at least 98% or at least 99% identical to residues 22-373 of SEQ ID NO: 109, or encoding one or more immunogenic fragments thereof;

administering to the subject a GSC-1 protein comprising an amino acid sequence at least 80%, at least 85%, at least 90%, at least 95%, at least 96%, at least 97%, at least 98% or at least 99% identical to residues 22-606 of SEQ ID NO: 111, or one or more immunogenic fragments thereof; or administering to the subject a nucleic acid molecule encoding a GSC-1 protein comprising an amino acid sequence at least 80%, at least 85%, at least 90%, at least 95%, at least 96%, at least 97%, at least 98% or at least 99% identical to residues 22-606 of SEQ ID NO: 111, or encoding one or more immunogenic fragments thereof;

administering to the subject a Ght5 protein comprising an amino acid sequence at least 80%, at least 85%, at least 90%, at least 95%, at least 96%, at least 97%, at least 98% or at least 99% identical to SEQ ID NO: 1, or one or more immunogenic fragments thereof; or administering to the subject a nucleic acid molecule encoding a Ght5 protein comprising an amino acid sequence at least 80%, at least 85%, at least 90%, at least 95%, at least 96%, at least 97%, at least 98% or at least 99% identical to SEQ ID NO: 1, or encoding one or more immunogenic fragments thereof;

administering to the subject an Erg6 protein comprising an amino acid sequence at least 90% identical to SEQ ID NO: 4, or one or more immunogenic fragments thereof; or administering to the subject a nucleic acid molecule encoding an Erg6 protein comprising an amino acid sequence at least 80%, at least 85%, at least 90%, at least 95%, at least 96%, at least 97%, at least 98% or at least 99% identical to SEQ ID NO: 4, or encoding one or more immunogenic fragments thereof;

administering to the subject an ATP2 protein comprising an amino acid sequence at least 80%, at least 85%, at least 90%, at least 95%, at least 96%, at least 97%, at least 98% or at least 99% identical to SEQ ID NO: 5, or one or more immunogenic fragments thereof; or administering to the subject a nucleic acid molecule encoding an ATP2 protein comprising an amino acid sequence at least 80%, at least 85%, at least 90%, at least 95%, at least 96%, at least 97%, at least 98% or at least 99% identical to SEQ ID NO: 5, or encoding one or more immunogenic fragments thereof;

administering to the subject a Gas4 protein comprising an amino acid sequence at least 80%, at least 85%, at least 90%, at least 95%, at least 96%, at least 97%, at least 98% or at least 99% identical to SEQ ID NO: 6 or SEQ ID NO: 7, or one or more immunogenic fragments thereof; or administering to the subject a nucleic acid molecule encoding a Gas4 protein comprising an amino acid sequence at least 80%, at least 85%, at least 90%, at least 95%, at least 96%, at least 97%, at least 98% or at least 99% identical to SEQ ID NO: 6 or SEQ ID NO: 7, or encoding one or more immunogenic fragments thereof; or administering to the subject a Mfs1 protein comprising an amino acid sequence at least 80%, at least 85%, at least 90%, at least 95%, at least 96%, at least 97%, at least 98% or at least 99% identical to SEQ ID NO: 8, or one or more immunogenic fragments thereof; or administering to the subject a nucleic acid molecule encoding a Mfs1 protein comprising an amino acid sequence at least 80%, at least 85%, at least 90%, at least 95%, at least 96%, at least 97%, at least 98% or at least 99% identical to SEQ ID NO: 8, or encoding one or more immunogenic fragments thereof.

Also provided is a method of immunizing a subject against *pneumocystis* pneumonia. In some embodiments, the method includes:

administering to the subject a Meu10 protein comprising an amino acid sequence at least 80%, at least 85%, at least 90%, at least 95%, at least 96%, at least 97%, at least 98% or at least 99% identical to residues 22-373 of SEQ ID NO: 109, or one or more immunogenic fragments thereof; or administering to the subject a nucleic acid molecule encoding a Meu10 protein comprising an amino acid sequence at least 80%, at least 85%, at least 90%, at least 95%, at least 96%, at least 97%, at least 98% or at least 99% identical to residues 22-373 of SEQ ID NO: 109, or encoding one or more immunogenic fragments thereof;

administering to the subject a GSC-1 protein comprising an amino acid sequence at least 80%, at least 85%, at least 90%, at least 95%, at least 96%, at least 97%, at least 98% or at least 99% identical to residues 22-606 of SEQ ID NO: 111, or one or more immunogenic fragments thereof; or administering to the subject a nucleic acid molecule encoding a GSC-1 protein comprising an amino acid sequence at least 80%, at least 85%, at least 90%, at least 95%, at least 96%, at least 97%, at least 98% or at least 99% identical to residues 22-606 of SEQ ID NO: 111, or encoding one or more immunogenic fragments thereof;

administering to the subject a Ght5 protein comprising an amino acid sequence at least 80%, at least 85%, at least 90%, at least 95%, at least 96%, at least 97%, at least 98% or at least 99% identical to SEQ ID NO: 1, or one or more immunogenic fragments thereof; or administering to the subject a nucleic acid molecule encoding a Ght5 protein comprising an amino acid sequence at least 80%, at least 85%, at least 90%, at least 95%, at least 96%, at least 97%, at least 98% or at least 99% identical to SEQ ID NO: 1, or encoding one or more immunogenic fragments thereof;

administering to the subject an Erg6 protein comprising an amino acid sequence at least 90% identical to SEQ ID NO: 4, or one or more immunogenic fragments thereof; or administering to the subject a nucleic acid molecule encoding an Erg6 protein comprising an amino acid sequence at least 80%, at least 85%, at least 90%, at least 95%, at least 96%, at least 97%, at least 98% or at least 99% identical to SEQ ID NO: 4, or encoding one or more immunogenic fragments thereof;

administering to the subject an ATP2 protein comprising an amino acid sequence at least 80%, at least 85%, at least 90%, at least 95%, at least 96%, at least 97%, at least 98% or at least 99% identical to SEQ ID NO: 5, or one or more immunogenic fragments thereof; or administering to the subject a nucleic acid molecule encoding an ATP2 protein comprising an amino acid sequence at least 80%, at least 85%, at least 90%, at least 95%, at least 96%, at least 97%, at least 98% or at least 99% identical to SEQ ID NO: 5, or encoding one or more immunogenic fragments thereof;

administering to the subject a Gas4 protein comprising an amino acid sequence at least 80%, at least 85%, at least 90%, at least 95%, at least 96%, at least 97%, at least 98% or at least 99% identical to SEQ ID NO: 6 or SEQ ID NO: 7, or one or more immunogenic fragments thereof; or administering to the subject a nucleic acid molecule encoding a Gas4 protein comprising an amino acid sequence at least 80%, at least 85%, at least 90%, at least 95%, at least 96%, at least 97%, at least 98% or at least 99% identical to SEQ ID NO: 6 or SEQ ID NO: 7, or encoding one or more immunogenic fragments thereof; or administering to the subject a Mfs1 protein comprising an amino acid sequence at least 80%, at least 85%, at least 90%, at least 95%, at least 96%, at least 97%, at least 98% or at least 99% identical to SEQ ID NO: 8, or one or more immunogenic fragments thereof; or administering to the subject a nucleic acid molecule encoding a Mfs1 protein comprising an amino acid sequence at least 80%, at least 85%, at least 90%, at least 95%, at least 96%, at least 97%, at least 98% or at least 99% identical to SEQ ID NO: 8, or encoding one or more immunogenic fragments thereof.

Further provided is a method of treating a subject diagnosed with *pneumocystis* pneumonia. In some embodiments, the method includes administering to the subject a monoclonal antibody specific for:

a Meu10 protein comprising an amino acid sequence at least 80%, at least 85%, at least 90%, at least 95%, at least 96%, at least 97%, at least 98% or at least 99% identical to residues 22-373 of SEQ ID NO: 109, or an immunogenic fragment thereof;

a GSC-1 protein comprising an amino acid sequence at least 80%, at least 85%, at least 90%, at least 95%, at least 96%, at least 97%, at least 98% or at least 99% identical to residues 22-606 of SEQ ID NO: 111, or an immunogenic fragment thereof;

a Ght5 protein comprising an amino acid sequence at least 80%, at least 85%, at least 90%, at least 95%, at least 96%, at least 97%, at least 98% or at least 99% identical to SEQ ID NO: 1, or an immunogenic fragment thereof;

an Erg6 protein comprising an amino acid sequence at least 80%, at least 85%, at least 90%, at least 95%, at least 96%, at least 97%, at least 98% or at least 99% identical to SEQ ID NO: 4, or an immunogenic fragment thereof;

an ATP2 protein comprising an amino acid sequence at least 80%, at least 85%, at least 90%, at least 95%, at least 96%, at least 97%, at least 98% or at least 99% identical to SEQ ID NO: 5, or an immunogenic fragment thereof;

a Gas4 protein comprising an amino acid sequence at least 80%, at least 85%, at least 90%, at least 95%, at least 96%, at least 97%, at least 98% or at least 99% identical to SEQ ID NO: 6 or SEQ ID NO: 7, or an immunogenic fragment thereof; or a Mfs1 protein comprising an amino acid sequence at least 80%, at least 85%, at least 90%, at least 95%, at least 96%, at least 97%, at least 98% or at least 99% identical to SEQ ID NO: 8, or an immunogenic fragment thereof.

In some examples of the methods disclosed herein, the amino acid sequence of the Meu10 protein comprises or consists of residues 22-373 of SEQ ID NO: 109; the amino acid sequence of the GSC-1 protein comprises or consists of residues 22-606 of SEQ ID NO: 111; the amino acid sequence of the Ght5 protein comprises or consists of SEQ ID NO: 1; the amino acid sequence of the Erg6 protein comprises or consists of SEQ ID NO: 4; the amino acid sequence of the ATP2 protein comprises or consists of SEQ ID NO: 5; the amino acid sequence of the Gas4 protein comprises or consists of SEQ ID NO: 6 or SEQ ID NO: 7; or the amino acid sequence of the Mfs1 protein comprises or consists of SEQ ID NO: 8.

In particular non-limiting examples, the method includes administering a Meu10 protein, wherein the amino acid sequence of the Meu10 protein comprises residues 22-373 of SEQ ID NO: 109; residues 1-373 of SEQ ID NO: 109; residues 22-408 of SEQ ID NO: 109; or SEQ ID NO: 109.

In other particular non-limiting examples, the method includes administering a nucleic acid encoding a Meu10 protein, wherein the nucleic acid comprises nucleotides 79-1137 of SEQ ID NO: 108; nucleotides 19-1137 of SEQ ID NO: 108; nucleotides 79-1245 of SEQ ID NO: 108; nucleotides 19-1245 of SEQ ID NO: 108; or SEQ ID NO: 108.

In other particular non-limiting examples, the method includes administering a GSC-1 protein, wherein the amino acid sequence of the GSC-1 protein comprises residues 22-606 of SEQ ID NO: 111; residues 1-606 of SEQ ID NO: 111; residues 22-641 of SEQ ID NO: 111; or SEQ ID NO: 111.

In other particular non-limiting examples, the method includes administering a nucleic acid encoding a GSC-1 protein, wherein the nucleic acid comprises nucleotides 74-1822 of SEQ ID NO: 110; nucleotides 11-1822 of SEQ ID NO: 110; nucleotides 74-1930 of SEQ ID NO: 110; nucleotides 11-1930 of SEQ ID NO: 110; or SEQ ID NO: 110.

In some embodiments of the methods disclosed herein, the one or more immunogenic fragments of the Meu10 protein comprise the amino acid sequence of any one of SEQ ID NOs: 29-38 and 136-148; the one or more immunogenic fragments of the GSC-1 protein comprises the amino acid sequence of any one of SEQ ID NOs: 19-28 and 126-135; the one or more immunogenic fragments of the Ght5 protein comprises the amino acid sequence of any one of SEQ ID NOs: 9-18 and 112-125; the one or more immunogenic fragments of the Erg6 protein comprises the amino acid sequence of any one of SEQ ID NOs: 39-48 and 149-159; the one or more immunogenic fragments of the ATP2 protein comprises the amino acid sequence of any one of SEQ ID NOs: 49-62 and 160-174; the one or more immunogenic fragments of the Gas4 protein comprises the amino acid sequence of any one of SEQ ID NOs: 63-90 and 175-211; or the one or more immunogenic fragments of the Mfs1 protein comprises the amino acid sequence of any one of SEQ ID NOs: 91-104 and 212-232.

In some examples, the methods provided herein include administering at least two, at least 3, at least 4, at least 5, at least 6, at least 7, at least 8, at least 9, or at least 10 immunogenic fragments of the Meu10 protein, wherein each of the immunogenic fragments comprises a different amino acid sequence selected from SEQ ID NOs: 29-38 and 136-148.

In other examples, the methods provided herein include administering at least two, at least 3, at least 4, at least 5, at least 6, at least 7, at least 8, at least 9, or at least 10 immunogenic fragments of the GSC-1 protein, wherein each of the immunogenic fragments comprises a different amino acid sequence selected from SEQ ID NOs: 19-28 and 126-135.

In other examples, the methods provided herein include administering at least two, at least 3, at least 4, at least 5, at least 6, at least 7, at least 8, at least 9, or at least 10 immunogenic fragments of the Ght5 protein, wherein each of the immunogenic fragments comprises a different amino acid sequence selected from SEQ ID NOs: 9-18 and 112-125.

In other examples, the methods provided herein include administering at least two, at least 3, at least 4, at least 5, at least 6, at least 7, at least 8, at least 9, or at least 10 immunogenic fragments of the Erg6 protein, wherein each of the immunogenic fragments comprises a different amino acid sequence selected from SEQ ID NOs: 39-48 and 149-159.

In other examples, the methods provided herein include administering at least two, at least 3, at least 4, at least 5, at least 6, at least 7, at least 8, at least 9, or at least 10 immunogenic fragments of the ATP2 protein, wherein each of the immunogenic fragments comprises a different amino acid sequence selected from SEQ ID NOs: 49-62 and 160-174.

In other examples, the methods provided herein include administering at least two, at least 3, at least 4, at least 5, at least 6, at least 7, at least 8, at least 9, or at least 10 immunogenic fragments of the Gas4 protein, wherein each of the immunogenic fragments comprises a different amino acid sequence selected from SEQ ID NOs: 63-90 and 175-211.

In other examples, the methods provided herein include administering at least two, at least 3, at least 4, at least 5, at least 6, at least 7, at least 8, at least 9, or at least 10 immunogenic fragments of the Mfs1 protein, wherein each of the immunogenic fragments comprises a different amino acid sequence selected from SEQ ID NOs: 91-104 and 212-232.

In some embodiments of the methods in which a nucleic acid molecule is administered, the nucleic acid molecule is operably to a promoter (such as within a vector).

Further provided are methods of diagnosing a subject as having *pneumocystis* pneumonia by detecting fungal antigens. In some embodiments, the method includes contacting a sample from the subject with a monoclonal antibody specific for (i) a Meu10 protein comprising an amino acid sequence at least 80%, at least 85%, at least 90%, at least 95%, at least 96%, at least 97%, at least 98% or at least 99% identical to SEQ ID NO: 3, or an immunogenic fragment thereof; (ii) a GSC-1 protein comprising an amino acid sequence at least 80%, at least 85%, at least 90%, at least 95%, at least 96%, at least 97%, at least 98% or at least 99% identical to SEQ ID NO: 2, or an immunogenic fragment thereof; (iii) a Ght5 protein comprising an amino acid sequence at least 80%, at least 85%, at least 90%, at least 95%, at least 96%, at least 97%, at least 98% or at least 99% identical to SEQ ID NO: 1, or an immunogenic fragment thereof; (iv) an Erg6 protein comprising an amino acid sequence at least 80%, at least 85%, at least 90%, at least 95%, at least 96%, at least 97%, at least 98% or at least 99% identical to SEQ ID NO: 4, or an immunogenic fragment thereof; (v) an ATP2 protein comprising an amino acid sequence at least 80%, at least 85%, at least 90%, at least 95%, at least 96%, at least 97%, at least 98% or at least 99% identical to SEQ ID NO: 5, or an immunogenic fragment thereof; (vi) administering to the subject a Gas4 protein comprising an amino acid sequence at least 80%, at least 85%, at least 90%, at least 95%, at least 96%, at least 97%, at least 98% or at least 99% identical to SEQ ID NO: 6 or SEQ ID NO: 7, or an immunogenic fragment thereof; or (vii) a Mfs1 protein comprising an amino acid sequence at least 80%, at least 85%, at least 90%, at least 95%, at least 96%, at least 97%, at least 98% or at least 99% identical to SEQ ID NO: 8, or an immunogenic fragment thereof;

detecting binding of the antibody to the sample; and diagnosing the subject as having *pneumocystis* pneumonia when an increase in binding of the antibody to the sample, as compared to binding of the antibody to a control sample, is detected.

In some examples of the diagnostic method, the amino acid sequence of the Meu10 protein comprises or consists of residues of SEQ ID NO: 3; the amino acid sequence of the GSC-1 protein comprises or consists of SEQ ID NO: 2; the amino acid sequence of the Ght5 protein comprises or consists of SEQ ID NO: 1; the amino acid sequence of the Erg6 protein comprises or consists of SEQ ID NO: 4; the amino acid sequence of the ATP2 protein comprises or consists of SEQ ID NO: 5; the amino acid sequence of the Gas4 protein comprises or consists of SEQ ID NO: 6 or SEQ ID NO: 7; or the amino acid sequence of the Mfs1 protein comprises or consists of SEQ ID NO: 8.

Also provided herein is a method of diagnosing a *Pneumocystis jirovecii* infection in a subject by detecting fungal nucleic acid sequences. In some embodiments, the method includes performing RT-PCR on a sample obtained from the subject using Meu10- and GSC-1-specific primers to amplify Meu10 and GSC-1 nucleic acid present in the sample; detecting the presence or absence of Meu10 and GSC-1 amplification products; and diagnosing the *Pneumocystis jirovecii* infection in the subject if Meu10 and/or GSC-1 amplification products are detected.

In some examples, the method includes diagnosing the subject as having a fulminant *Pneumocystis jirovecii* infection if the presence of both Meu10 and GSC-1 amplification products detected. In other examples, the method includes diagnosing the subject as being colonized with *Pneumocystis jirovecii* if the presence of a GSC-1 amplification product and the absence of a Meu10 amplification product is detected. In particular examples, the Meu10-specific primers specifically hybridize with SEQ ID NO: 108; and/or the GSC-1-specific primers specifically hybridize with SEQ ID NO: 110. In some examples, the sample comprises sputum or bronchoalveolar lavage fluid. In other examples, the sample comprises a lung biopsy.

The present disclosure also provides recombinant Meu10 and recombinant GSC-1 nucleic acid molecules and proteins. In particular, provided herein is a recombinant Meu10 protein comprising the Meu10 ectodomain sequence set forth herein as residues 22-373 of SEQ ID NO: 109. In some embodiments, the recombinant Meu10 protein further comprises a heterologous leader sequence and/or one or more protein tags (such as a histidine and/or myc tag). Thus, in specific examples the recombinant Meu10 protein comprises residues 22-373 of SEQ ID NO: 109; residues 1-373 of SEQ ID NO: 109; residues 22-408 of SEQ ID NO: 109; or SEQ ID NO: 109. In one non-limiting example, the recombinant Meu10 protein consists of SEQ ID NO: 109.

Also provided herein is a recombinant GSC-1 protein comprising the GSC-1 ectodomain sequence set forth herein as residues 22-606 of SEQ ID NO: 111. In some embodiments, the recombinant GSC-1 protein further comprises a heterologous leader sequence and/or one or more protein tags (such as a histidine and/or myc tag). Thus, in specific examples the recombinant GSC-1 protein comprises residues 22-606 of SEQ ID NO: 111; residues 1-606 of SEQ ID NO: 111; residues 22-641 of SEQ ID NO: 111; or SEQ ID NO: 111. In one non-limiting example, the recombinant GSC-1 protein consists of SEQ ID NO: 111.

Also provided is a recombinant Meu10 nucleic acid molecule encoding a Meu10 ectodomain. In some embodiments, the nucleic acid molecule further encodes a heterologous leader sequence and/or one or more protein tags (such as a histidine and/or myc tag). In some examples, the recombinant Meu10 nucleic acid molecule comprises nucleotides 79-1137 of SEQ ID NO: 108; nucleotides 19-1137 of SEQ ID NO: 108; nucleotides 79-1245 of SEQ ID NO: 108; nucleotides 19-1245 of SEQ ID NO: 108; or SEQ ID NO: 108. In one non-limiting example, the recombinant Meu10 nucleic acid molecule consists of SEQ ID NO: 108.

Further provided is a recombinant GSC-1 nucleic acid molecule encoding a GSC-1 ectodomain. In some embodiments, the nucleic acid molecule further encodes a heterologous leader sequence and/or one or more protein tags (such as a histidine and/or myc tag). In some examples, the recombinant GSC-1 protein comprises nucleotides 74-1822 of SEQ ID NO: 110; nucleotides 11-1822 of SEQ ID NO: 110; nucleotides 74-1930 of SEQ ID NO: 110; nucleotides 11-1930 of SEQ ID NO: 110; or SEQ ID NO: 110. In one non-limiting example, the recombinant GSC-1 nucleic acid molecule consists of SEQ ID NO: 110.

In some embodiments, the recombinant Meu10 and GSC-1 nucleic acid molecules further include a promoter that is operably linked to the Meu10 or GSC-1 coding sequences. In some examples, the nucleic acid molecules comprise a vector.

Further provided herein is a method of eliciting an immune response against *Pneumocystis jirovecii* in a subject, comprising:

administering to the subject a protein comprising an amino acid sequence at least 80%, at least 85%, at least 90%, at least 95%, at least 96%, at least 97%, at least 98% or at least 99% identical to any one of SEQ ID NOs: 1-8, or an immunogenic fragment thereof;

administering to the subject a nucleic acid molecule encoding a protein comprising an amino acid sequence at least 80%, at least 85%, at least 90%, at least 95%, at least 96%, at least 97%, at least 98% or at least 99% identical to any one of SEQ ID NOs: 1-8, or an immunogenic fragment thereof;

administering to the subject a *Pneumocystis jirovecii* protein homologous to any one of the fungal proteins listed in Table 1, or an immunogenic fragment thereof (such as a *P. jirovecii* peptide listed in Table 3); or administering to the subject a nucleic acid molecule encoding a *Pneumocystis jirovecii* protein homologous to any one of the fungal proteins listed in Table 1, or an immunogenic fragment thereof (such as a nucleic acid encoding a *P. jirovecii* peptide listed in Table 3).

Also provided is a method of vaccinating (or immunizing) a subject against *pneumocystis* pneumonia, comprising:

administering to the subject a protein comprising an amino acid sequence at least 80%, at least 85%, at least 90%, at least 95%, at least 96%, at least 97%, at least 98% or at least 99% identical to any one of SEQ ID NOs: 1-8, or an immunogenic fragment thereof;

administering to the subject a nucleic acid molecule encoding a protein comprising an amino acid sequence at least 80%, at least 85%, at least 90%, at least 95%, at least 96%, at least 97%, at least 98% or at least 99% identical to any one of SEQ ID NOs: 1-8, or an immunogenic fragment thereof;

administering to the subject a *Pneumocystis jirovecii* protein homologous to any one of the fungal proteins listed in Table 1, or an immunogenic fragment thereof (such as a *P. jirovecii* peptide listed in Table 3); or administering to the subject a nucleic acid molecule encoding a *Pneumocystis jirovecii* protein homologous to any one of the fungal proteins listed in Table 1, or an immunogenic fragment thereof (such as a nucleic acid molecule encoding a *P. jirovecii* peptide listed in Table 3).

Also provided is a method of treating a subject diagnosed with *pneumocystis* pneumonia, comprising:

administering to the subject a protein comprising an amino acid sequence at least 80%, at least 85%, at least 90%, at least 95%, at least 96%, at least 97%, at least 98% or at least 99% identical to any one of SEQ ID NOs: 1-8, or an immunogenic fragment thereof;

administering to the subject a nucleic acid molecule encoding a protein comprising an amino acid sequence at least 80%, at least 85%, at least 90%, at least 95%, at least 96%, at least 97%, at least 98% or at least 99% identical to any one of SEQ ID NOs: 1-8, or an immunogenic fragment thereof;

administering to the subject a *Pneumocystis jirovecii* protein homologous to any one of the fungal proteins listed in Table 1, or an immunogenic fragment thereof (such as a *P. jirovecii* peptide listed in Table 3);

administering to the subject a nucleic acid molecule encoding a *Pneumocystis jirovecii* protein homologous to any one of the fungal proteins listed in Table 1, or an immunogenic fragment thereof (such as a nucleic acid molecule encoding a *P. jirovecii* peptide listed in Table 3); or administering a monoclonal antibody specific for (i) a protein comprising an amino acid sequence at least 80%, at least 85%, at least 90%, at least 95%, at least 96%, at least 97%, at least 98% or at least 99% identical to any one of SEQ ID NOs: 1-8, or an immunogenic fragment thereof; or (ii) a *Pneumocystis jirovecii* protein homologous to any one of the fungal proteins listed in Table 1, or an immunogenic fragment thereof (such as a *P. jirovecii* peptide listed in Table 3).

Further provided is a method of diagnosing a subject as having *pneumocystis* pneumonia, comprising:

contacting a sample from the subject with a monoclonal antibody specific for (i) a protein comprising an amino acid sequence at least 80%, at least 85%, at least 90%, at least 95%, at least 96%, at least 97%, at least 98% or at least 99% identical to any one of SEQ ID NOs: 1-8, or an immunogenic fragment thereof; or (ii) a *Pneumocystis jirovecii* protein homologous to any one of the fungal proteins listed in Table 1, or an immunogenic fragment thereof (such as a *P. jirovecii* peptide listed in Table 3); and detecting binding of the antibody to the sample, wherein an increase in binding of the antibody to the sample as compared to binding of the antibody to a control sample diagnoses the subject as having *pneumocystis* pneumonia.

In some embodiments, the amino acid sequence of the protein comprises or consists of any one of SEQ ID NOs: 1-8, or an immunogenic fragment of any one of SEQ ID NOs: 1-8. In some examples, the immunogenic fragment comprises any one of the peptides shown in Table 2. In some examples, the amino acid sequence of the protein comprises or consists of SEQ ID NO: 3, or an immunogenic fragment of SEQ ID NO: 3.

In some embodiments, the nucleic acid molecule is operably linked to a promoter.

IV. Peptides Identified from *P. murina* Surface Labeling

*P. murina* surface peptides were identified according to the procedures described in Example 1. Table 1 provides a list of eight proteins that were identified using the disclosed method.

TABLE 1

| The sequences of peptides identified from *P. murina* surface labeling | | | | | |
|---|---|---|---|---|---|
| Peptide Name | NCBI Accession No. (SEQ ID NO) | Species | *Pneumocystis* Name | *Pneumocystis* Accession No. | E Value |
| Ght5 | NP_587740.1 (SEQ ID NO: 1) | *S. pombe* | hypothetical protein | EMR10795.1 | 3E−51 |
| GSC-1 | AF191096_1 (SEQ ID NO: 2) | *P. carinii* | hypothetical protein | EMR08340.1 | 0 |
| Meu10 | NP_588357.1 (SEQ ID NO: 3) | *S. pombe* | hypothetical protein | EMR10161.1 | 2E−47 |
| Erg6 | NP_595787.1 (SEQ ID NO: 4) | *S. pombe* | hypothetical protein | EMR10032.1 | 5E−130 |
| ATP2 | NP_593151.1 (SEQ ID NO: 5) | *S. pombe* | ATP synthase F1, beta subunit | EMR10819.1 | 0 |
| Gas4 | NP_014509.1 (SEQ ID NO: 6) | *S. cerevisiae* | hypothetical protein | EMR11603.1 | 5E−86 |
| Gas4 | NP_596746.1 (SEQ ID NO: 7) | *S. pombe* | hypothetical protein | EMR11603.1 | 4E−124 |
| Mfs1 | NP_596009.1 (SEQ ID NO: 8) | *S. pombe* | Hypothetical protein | EMR08291.1 | 0.018 |

Biotinylated *Pneumocystis* surface protein peptides were identified by MS. Accession target peptide names match to the following NCBI target names from *S. pombe, S. cerevisiae* and *P. carinii* (Ght5—hexose transporter Ght5; GSC-1—1,3-beta-glucan synthase; Meu10—GPI-anchored cell surface protein; Erg6—methyltransferase; ATP2—ATPase beta subunit; Gas4 *S. cerevisiae*—Gas4p; Gas4 *S. pombe*—sporulation-specific 1,3-beta-glucanosyltransferase; Mfs1—vacuolar membrane amino acid uptake transporter Fnx1) and refer to the *P. murina* names/GENBANK™ accession numbers/E value.

Epitope analysis was performed on the eight fungal proteins listed in Table 1 to identify MHC class II binding peptides. A total of 96 peptides were selected for peptide synthesis and screening (see Example 1), which are shown below in Table 2.

TABLE 2

| The sequences of peptide pools of putative MHC class II epitopes | |
|---|---|
| Protein Name | Peptide Sequences |
| Hexose transporter Ght5 | IVGESYPIRYRSKCA (SEQ ID NO: 9) |
| | YAAVGNRALTRKNGT (SEQ ID NO: 10) |
| | LPESPRYLISVGRDE (SEQ ID NO: 11) |
| | VTAVPSWVQIMVAKI (SEQ ID NO: 12) |
| | PSWVQIMVAKIWTGL (SEQ ID NO: 13) |
| | EGTGMNSPYLSALIL (SEQ ID NO: 14) |
| | WTIVYLIGIILQVTA (SEQ ID NO: 15) |
| | LEFFGRRMPLIIGAL (SEQ ID NO: 16) |
| | KIWTGLSIGALSVLA (SEQ ID NO: 17) |
| | GTSNHRAGAVMIVFS (SEQ ID NO: 18) |
| 1,3-beta-glucan synthase GSC-1 | GLFGNYLYKKTRRYV (SEQ ID NO: 19) |
| | LESAIYRWKTRCTQM (SEQ ID NO: 20) |
| | IINGRYVRRERDHNK (SEQ ID NO: 21) |
| | ELTERGVWRASTRLA (SEQ ID NO: 22) |
| | PGAQHLTRRLLFLIL (SEQ ID NO: 23) |
| | TFSDFTMRSDMARAA (SEQ ID NO: 24) |
| | NMYDHMMVLLDSRAS (SEQ ID NO: 25) |
| | DFFIAFIPLVVQELT (SEQ ID NO: 26) |
| | KLRKRIVRRYATLFF (SEQ ID NO: 27) |
| | GGGVASLLMIVATLA (SEQ ID NO: 28) |
| GPI-anchored cell surface protein involved | NLQGIRFDKGIKKAH (SEQ ID NO: 29) |
| | NSAALAQIKGYDKLK (SEQ ID NO: 30) |
| | VESKFYVSYNAREIS (SEQ ID NO: 31) |

TABLE 2-continued

| The sequences of peptide pools of putative MHC class II epitopes | |
|---|---|
| Protein Name | Peptide Sequences |
| in ascospore wall assembly Meu10 | TVGDMTIQRVAHLQL (SEQ ID NO: 32) |
| | HKLTIEDTQLSTLAG (SEQ ID NO: 33) |
| | NVGQLTMRILPNLQG (SEQ ID NO: 34) |
| | EKLTRLASVYAPQLA (SEQ ID NO: 35) |
| | FYVSYNAREISVTLP (SEQ ID NO: 36) |
| | GGTFMIANSAALAQI (SEQ ID NO: 37) |
| | SVGGELRFEKLTRLA (SEQ ID NO: 38) |
| Sterol 24-C-methyltransferase Erg6 | RCNNYAVKRNLDKKQ (SEQ ID NO: 39) |
| | HLFTPMFLMIAKKPE (SEQ ID NO: 40) |
| | NNYAVKRNLDKKQVF (SEQ ID NO: 41) |
| | RHEHYLAYRMGIKPG (SEQ ID NO: 42) |
| | PQMVRKCDAVEAIKK (SEQ ID NO: 43) |
| | FTVFRTSRLGKLVTR (SEQ ID NO: 44) |
| | KLVTRYSVQFLEKIG (SEQ ID NO: 45) |
| | YRMGIKPGSRVLDVG (SEQ ID NO: 46) |
| | GVAAKGTSKVGDTLA (SEQ ID NO: 47) |
| | EDRARRIDGYKSVVN (SEQ ID NO: 48) |
| ATPase beta subunit (ATP2) | YKLPRKSWLNTAKFN (SEQ ID NO: 49) |
| | GRLVSLKDTIRSFKE (SEQ ID NO: 50) |
| | EADKLTVERARKVQR (SEQ ID NO: 51) |
| | YASTEAAKHNKGSIK (SEQ ID NO: 52) |
| | PGARARVALTGLTVA (SEQ ID NO: 53) |
| | TDMGAMQERITTTKK (SEQ ID NO: 54) |
| | HVGENTVRTIAMDGT (SEQ ID NO: 55) |
| | SEVSALLGRIPSAVG (SEQ ID NO: 56) |
| | GSVQQMLQEYKSLQD (SEQ ID NO: 57) |
| | GARARVALTGLTVAE (SEQ ID NO: 58) |
| | FGQMNEPPGARARVA (SEQ ID NO: 59) |
| | KLTVERARKVQRFLS (SEQ ID NO: 60) |
| | DLYREMQETGVIKLE (SEQ ID NO: 61) |
| | TKKGSITSVQAVYVP (SEQ ID NO: 62) |
| 1,3-beta-glucanosyl-transferase Gas4 (*Saccharomyces cerevisiae*) | KDDLKRKHRNSASIS (SEQ ID NO: 63) |
| | GTMKNYISAHSPRTI (SEQ ID NO: 64) |
| | TLVDAYRSYSKPVFF (SEQ ID NO: 65) |
| | GDRWNGPKKIEIRQS (SEQ ID NO: 66) |
| | HDACMTMLAMAGIYL (SEQ ID NO: 67) |
| | SSTFIFLILELVVLC (SEQ ID NO: 68) |
| | YQWCGQQTMQTSGYD (SEQ ID NO: 69) |
| | IEFPSMKTLKETVQM (SEQ ID NO: 70) |
| | ACMTMLAMAGIYLIL (SEQ ID NO: 71) |
| | CMTMLAMAGIYLILD (SEQ ID NO: 72) |
| | GPKKIEIRQSLTLAD (SEQ ID NO: 73) |
| | GLVEYQEDDSVQLLA (SEQ ID NO: 74) |

TABLE 2-continued

The sequences of peptide pools of putative MHC class II epitopes

| Protein Name | Peptide Sequences |
|---|---|
| | NKVLPRQFQEIGYLF (SEQ ID NO: 75)<br>PDLNHDACMTMLAMA (SEQ ID NO: 76) |
| 1,3-beta-glucanosyltransferase Gas4 (*Schizosaccharomyces pombe*) | RDVKAYIKKHSDRHI (SEQ ID NO: 77)<br>ILDLNTYRHSISRAH (SEQ ID NO: 78)<br>SSSLVDPLASRSCKK (SEQ ID NO: 79)<br>SKTNERFYIRGVDYQ (SEQ ID NO: 80)<br>AITWVKAVTRDVKAY (SEQ ID NO: 81)<br>LKATAQTHPIVIKGN (SEQ ID NO: 82)<br>LGINTVRVYQVDNSA (SEQ ID NO: 83)<br>AADVAENRLQLAHYF (SEQ ID NO: 84)<br>FCQALFITVLIATLS (SEQ ID NO: 85)<br>MGVANIIYALFLLGP (SEQ ID NO: 86)<br>KCMNALSEAGIYVIL (SEQ ID NO: 87)<br>SAEPNHYGLVVIDKD (SEQ ID NO: 88)<br>AHPALSYNKVYLQHL (SEQ ID NO: 89)<br>VVNDEDTTAITWVKA (SEQ ID NO: 90) |
| Vacuolar membrane amino acid uptake transporter Fnx1 (Mfs1) | TILVAWRVRVKPTVR (SEQ ID NO: 91)<br>EQTSLLYPEVSRKKE (SEQ ID NO: 92)<br>LFAFYWVEKNIAVEP (SEQ ID NO: 93)<br>GGLIAQRWGWRTAFH (SEQ ID NO: 94)<br>IAFAGFWCSLRIKQF (SEQ ID NO: 95)<br>FLLVTGITALVVTFN (SEQ ID NO: 96)<br>GFFFMLMGIVSFAVL (SEQ ID NO: 97)<br>VAWRVRVKPTVRNSN (SEQ ID NO: 98)<br>AFPWVSPVIITLLVS (SEQ ID NO: 99)<br>TTLSILMKQLASNLK (SEQ ID NO: 100)<br>YIVTAYLITNTAFQP (SEQ ID NO: 101)<br>GFLSALDMTIVASLY (SEQ ID NO: 102)<br>FHFQVPMGILSTILV (SEQ ID NO: 103)<br>RLSDIFGRRPTVVFA (SEQ ID NO: 104) |

The pools of MHC class II-binding peptides used to test CD4+ T cell response using ELISPOT™ analysis are listed. A total of 14 unique peptides (15 amino acids in length) were chosen for the genes encoding Atp2, *S. cerevisiae* Gas4, *S. pombe* Gas4, and Mfs1, and 10 peptides were chosen for Ght5, GSC-1, Meu10, and Erg6.

Table 3 provides a list of *P. jirovecii* peptides that are orthologous to the *S. pombe, P. carinii* and *S. cerevisiae* peptides listed in Table 2.

TABLE 3

*Pneumocystis jirovecii* orthologous peptides

| Protein | *P. jirovecii* peptide sequence | SEQ ID NO | Orthologous to SEQ ID NO |
|---|---|---|---|
| Ght5 | ESYLTRNRSK | 112 | 9 |
| Ght5 | LTRKNGT | 113 | 10 |
| Ght5 | YLVSVGHDE or ESPRQLISIG | 114/115 | 11 |
| Ght5 | WVQIMVAKI | 116 | 12 |
| Ght5 | QIML--FWSGL | 117 | 13 |
| Ght5 | GTGINNPF-SALI | 118 | 14 |
| Ght5 | LIGIILQ or TITFLIGII | 119/120 | 15 |
| Ght5 | FYGRRTKMDPLLNSCVIGGL | 121 | 16 |
| Ght5 | LSIGELSV or KIWGTASGLSI | 122/123 | 17 |

TABLE 3-continued

*Pneumocystis jirovecii* orthologous peptides

| Protein | *P. jirovecii* peptide sequence | SEQ ID NO | Orthologous to SEQ ID NO |
|---|---|---|---|
| Ght5 | SNHIASAVVI or AVMAVFS | 124/125 | 18 |
| GSC-1 | GLFGNYLYKKTRRYV | 126 | 19 |
| GSC-1 | LESAIYRWKTKCSQM | 127 | 20 |
| GSC-1 | IINGRYVRRERDHNK | 128 | 21 |
| GSC-1 | ELTERGVWRASTRLA | 129 | 22 |
| GSC-1 | GAQHLTRRLLFLIL | 130 | 23 |
| GSC-1 | FSDFTMRSDMARAA | 131 | 24 |
| GSC-1 | NMYDHMMVLLDSRAS | 132 | 25 |
| GSC-1 | FFIAFIPLVVQELT | 133 | 26 |
| GSC-1 | KLRKRIVRRYATLFF | 134 | 27 |
| GSC-1 | GGGVASLLMIIATLA | 135 | 28 |
| Meu10 | NLEGIS--KSIKK | 136 | 29 |
| Meu10 | SVALNQIESYDNL | 137 | 30 |
| Meu10 | ESKFY-SYD or VED-FY-SIYYN | 138/139 | 31 |
| Meu10 | TLGDCKMTIQ | 140 | 32 |
| Meu10 | LSLEDAQLANLPG or DMQLSTMAG | 141/142 | 33 |
| Meu10 | TMRLITNLQ | 143 | 34 |
| Meu10 | LGRLASVVAKQL or EKLQRLA-----QLA | 144/145 | 35 |
| Meu10 | SYNARDV | 146 | 36 |
| Meu10 | MIDNSAPL | 147 | 37 |
| Meu10 | SVNEEYRFEKL | 148 | 38 |
| Erg6 | NIALKRTINLGKKQ | 149 | 39 |
| Erg6 | YTPM--MVAKEP | 150 | 40 |
| Erg6 | VTRNAEKKQV | 151 | 41 |
| Erg6 | RHEHYLASHAGIREG | 152 | 42 |
| Erg6 | EAVEGIKK | 153 | 43 |
| Erg6 | VFRASRTGQL | 154 | 44 |
| Erg6 | TSYSVQFL | 155 | 45 |
| Erg6 | IKPGAVVIDVG | 156 | 46 |
| Erg6 | GVAPKGCKKVNDVL or AAKNTSKPGE | 157/158 | 47 |
| Erg6 | DRAHRI-GQKNVVN | 159 | 48 |
| ATP2 | RKAWLN | 160 | 49 |
| ATP2 | GRLVSLKDTLRSFKE | 161 | 50 |
| ATP2 | EADKLTVERARKLQR | 162 | 51 |

TABLE 3-continued

| Protein | *P. jirovecii* peptide sequence | SEQ ID NO | Ortho-logous to SEQ ID NO |
|---|---|---|---|
| | *Pneumocystis jirovecii* orthologous peptides | | |
| ATP2 | ANIEAAKH | 163 | 52 |
| ATP2 | PGARARVALTGLTVA | 164 | 53 |
| ATP2 | TDMGGMQERITTTKK | 165 | 54 |
| ATP2 | HMGERTVRTIAMDGT | 166 | 55 |
| ATP2 | SEVSALLGRIPSAVG | 167 | 56 |
| ATP2 | QQMLQEY or VQFILQSYKSLQD | 168/169 | 57 |
| ATP2 | GARARVALTGLTVAE | 170 | 58 |
| ATP2 | FGQMNEPPGARARVA | 171 | 59 |
| ATP2 | KLTVERARKLQRFMS | 172 | 60 |
| ATP2 | DLYHEMIQTGVIKLD | 173 | 61 |
| ATP2 | TKKGSITSIQAVYVP | 174 | 62 |
| Gas4 s.cer | KDELKRKH | 175 | 63 |
| Gas4 s.cer | KNHNYSYISEHSP | 176 | 64 |
| Gas4 s.cer | TLVEAYKVYRK | 177 | 65 |
| Gas4 s.cer | GPKKIEV | 178 | 66 |
| Gas4 s.cer | MTGIYL or MAGIY | 179/180 | 67 |
| Gas4 s.cer | TFFFFIIELIVL | 181 | 68 |
| Gas4 s.cer | YEWCEPTTFETSGY or QQTMQT | 182/183 | 69 |
| Gas4 s.cer | MKTLKE | 184 | 70 |
| Gas4 s.cer | CMNLFAKNGVYVIL | 185 | 71 |
| Gas4 s.cer | CMNLFAKNGVYVILD | 186 | 72 |
| Gas4 s.cer | GPKKIEV | 187 | 73 |
| Gas4 s.cer | DSVQLLA | 188 | 74 |
| Gas4 s.cer | NK-LQRMFQDIG or VLPRQLQ | 189/190 | 75 |
| Gas4 s.cer | DLNHD or PELNQDA | 191/192 | 76 |
| Gas4 s.pom | RDTKAYIRHKH | 193 | 77 |
| Gas4 s.pom | ILDLSEPRNSI | 194 | 78 |
| Gas4 s.pom | VDPLANSRAC | 195 | 79 |
| Gas4 s.pom | FFVKGVAYQ or ERFYIRG | 1956/197 | 80 |
| Gas4 s.pom | VKAAIRDTKAY | 198 | 81 |
| Gas4 s.pom | QVHPIVI | 199 | 82 |
| Gas4 s.pom | LGINTVRVYTID | 200 | 83 |
| Gas4 s.pom | ENRLQ | 201 | 84 |
| Gas4 s.pom | YCMNLF or LIATLS | 202/203 | 85 |
| Gas4 s.pom | IIYSLFL or IYALFL | 204/205 | 86 |
| Gas4 s.pom | CMNLFAKNGVYVIL or AMREAGIYV | 206/207 | 87 |
| Gas4 s.pom | NSYGLVIIHND | 208 | 88 |
| Gas4 s.pom | NKVYLNQL | 209 | 89 |
| Gas4 s.pom | VSDEDTKGI or VINDED | 210/211 | 90 |
| Mfs1 | WRVRV or VAWRHRLK | 212/213 | 91 |
| Mfs1 | SLLYNDLSRK | 214 | 92 |
| Mfs1 | EKNIPVE | 215 | 93 |
| Mfs1 | WRTAF or WRTDFH | 216/217 | 94 |
| Mfs1 | LRIKQF or FAGFW | 218/219 | 95 |
| Mfs1 | LVVTFN or LLVTGIKPL | 220/221 | 96 |
| Mfs1 | FFFLLGIV | 222 | 97 |
| Mfs1 | WRVRV or VAWRHRLK | 223/224 | 98 |
| Mfs1 | IIITLLIS | 225 | 99 |
| Mfs1 | LSRLMSQMSKIISNLK | 226 | 100 |
| Mfs1 | YIVTEY | 227 | 101 |
| Mfs1 | SELDMTI or FLSALD | 228/229 | 102 |
| Mfs1 | FHYQVP or VPLGILS | 230/231 | 103 |
| Mfs1 | LSDIHNRNPSVV | 232 | 104 |

The following examples are provided to illustrate certain particular features and/or embodiments. These examples should not be construed to limit the disclosure to the particular features or embodiments described.

EXAMPLES

Described in the Examples below is the development of a surface protein labeling protocol for *Pneumocystis murina* (*P. murina*). High yield *P. murina* was propagated and harvested from Rag2$^{-/-}$Il2rg$^{-/-}$mice (Kelly et al., *J Immunol* 190:285-295, 2013). The surface proteins of purified *P. murina* were biotin labeled and analyzed using LC-MS to determine peptide sequences and sites of NHS ester labeling. The tandem mass spectral data of peptides were then used to query against the NCBI RefSeq protein sequence for fungi (Taxonomy ID: 4751) and the *P. murina* draft genome database to identify peptides (Cisse et al., *M Bio* 4:e00428-00412, 2012). Major surface glycoproteins (MSGs) as well as a set of novel cell surface proteins were identified; eight non-MSG protein sequences were selected for further study. To determine if these proteins were seen by the immune system as CD4+ T-cell epitopes, these proteins were analyzed for putative class II MHC binding, peptides were synthesized from these regions, and T-cell ELISPOT™ studies were performed. The stimulation response showed that these peptide pools contain immunogenic T-cell epitopes suggesting that these antigens are part of the natural host response to *P. murina* infection. Further investigation of two antigens, Meu10 and GSC-1, demonstrated that Meu10 and GSC-1 antibodies are generated during the course of natural *P. murina* infection and that anti-Meu10 and anti-GSC-1 serum recognizes the surface of *P. murina*.

Example 1: *Pneumocystis* Antigen Discovery Using Fungal Surface Proteomics

This example describes the identification of eight fungal proteins (Ght5, GSC-1, Meu10, Erg6, ATP2, Gas4—*S. cerevisiae*, Gas—*S. pombe*, and Mfs1) using a surface protein labeling protocol for *P. murina*.

Methods

*Pneumocystis murina* and its Antigen Preparation

To prepare *P. murina* for cell surface labeling, *Pneumocystis* organisms were collected from lung bronchoalveolar lavage (BAL) fluid (Empey et al., Infect Immun 72:6211-6220, 2004) of Rag2$^{-/-}$Il2rg$^{-/-}$mice (on a B6 background) that were previously inoculated with *P. murina* for eight weeks. To confirm the presence of *P. murina* organisms, the pellet was resuspended in PBS, and a 1:9 dilution was stained with modified Giemsa stain (Diff-Quick; Baxter). Gram stains were performed on the inoculum to exclude contamination with bacteria. For *P. murina* antigen, *Pneumocystis* organisms were isolated from lung tissue of Rag2$^{-/-}$Il2rg$^{-/-}$mice that were previously inoculated with *P. murina. P. murina* organisms were purified by differential centrifugation as previously described (Zheng et al., *J Clin Invest* 108:1469-1474, 2001), and protein antigen was produced by sonication for five minutes and the concentration was determined by bicinchoninic acid assay (Thermo Scientific, Rockford, Ill.).

*Pneumocystis murina* Surface Protein Labeling

*P. murina* from BAL of *P. murina* inoculated Rag2$^{-/-}$Il2rg$^{-/-}$mice was labeled by Sulfo-NHS-LC-biotin (Thermo Scientific, Rockford, Ill.). Sulfo-NHS-LC-biotin reacts with primary amine groups (unmodified N-termini of proteins/peptides and unmodified lysine side chain) in proteins from both *Pneumocystis* and the host, and tags the exposed portions of proteins covalently with the biotin moiety (the sulfo-NHS ester group is cell membrane impermeable). Sulfo-NHS-LC-biotin targets the free amine group of the unmodified N-terminus and the side-chain of lysine and labels only surface components (Ali and Bergson, *J Biol Chem* 278:51654-51663, 2003). It is conceivable that the sulfo-NHS-LC-biotin labeling reaction is biased to the lysine residue containing exposed regions of proteins, no matter if they are from *P. murina* or from the host. Moreover, it is possible that non-surface proteins could be labeled in this process if there are lysed organisms in the preparation. It is also important to note that detection of sulfo-NHS-LC-biotin labeled peptide does not reflect the real abundance of the relevant protein from which the labeled peptide is derived. Actual protein abundance determination is out of the range that can be achieved by the cell surface labeling approach employed in this study.

*Pneumocystis murina* Surface Peptide Identification

Peptides released from *P. murina* cell surface by trypsin digestion were affinity purified by an avidin column, and the enriched sulfo-NHS-LC-biotin labeled peptides went through LC-MS/MS analysis performed on a linear ion trap LTQ mass spectrometer (Thermo Electron, San Jose, Calif.) coupled with a nano-flow electrospray source. The LC-MS/MS instrument was operated under data-dependent acquisition mode with the top five strongest peptide ions in an MS scan selected for collision-induced decomposition. Peptides in the sample were first separated by reversed-phase liquid chromatography, then a single peptide ion was isolated by its mass to charge ratio (m/z) for fragmentation. Mass tolerance was set as: precursor ion 2 Da and fragment ion 1 Da. Methionine oxidation (M+15.99 Da), carboxyamidomethylation of cysteine (C+57.02 Da), sulfo-NHS-LC-biotin labeling of lysine (K+339.45 Da) were set as differential modifications. None of the enzymatic/chemical cleavage rules were applied to the in-silico generation of peptide sequences with 6 to 30 amino acid residues in length from the protein sequences in the database. Two database search engines, PEAKS® Studio (Bioinformatics Solutions Inc. Waterloo, ON Canada) and BioWorks 3.3 (Thermo Electron, San Jose, Calif.), were employed to perform an in-house database search to identify peptide sequences and facilitate validation of peptide identification. Identification of a peptide sequence was based on one MS/MS spectrum (resulting from fragmentation of one peptide in the sample mixture). The identification of a peptide sequence also included information on (a) if the peptide sequence was unique to one protein or shared by multiple proteins, (b) the source of proteins (or homologues if the protein sequence database of a related species was employed), (c) identified peptides with labeled lysine residues. Peptide sequences shared by *Pneumocystis* proteins and host proteins were determined using a BLAST search against NCBI non-redundant protein sequence database. The tandem mass spectral data of peptides were also searched against the recently released *P. murina* protein sequence database (*Pneumocystis murina* Sequencing Project, Broad Institute of Harvard and MIT (available online at broadinstitute.org/)).

Antigen Peptide T-Cell Epitope Analysis

A total of eight fungal proteins were chosen for epitope analysis based on surface peptide identification (Table 1). Potential MHC class II-binding peptides were predicted for each potential protein antigen using the Immune Epitope Database and Analysis Resource T cell epitope prediction tools for peptide binding to MHC class II molecules (online at tools.immuneepitope.org/analyze/html/mhc_II_binding.html). This tool employs a consensus approach to predict MHC class II epitopes based upon Sturniolo, ARB, and SMM_align algorithms (Zhang et al., *Nucleic Acids Res* 36:W513-518, 2008). For each gene product, the predicted peptide binding results for mouse MHC Class II were sorted by top percentile using the consensus score, and 10-14 of the highest ranked peptides with a unique Average Relative Binding (ARB) matrix core sequence were selected for each of the eight fungal surface protein candidates. A total of 96 peptides were chosen for peptide synthesis and screening (see Table 2 above).

ELISPOT™ Analysis

C57/B6 wild type (wt) mice were inoculated with *P. murina* for two weeks. Total lymphocytes that included T cells, B cells, and antigen-presenting cells from lung draining lymph node of *P. murina* inoculated mice were collected. Total lymphocytes were resuspended in complete Iscove's modified Dulbecco's medium (IMDM) (Invitrogen, Grand Island, N.Y.), and then distributed at 200,000 cells/well in 96-well ELISPOT™ plates pretreated with mouse IFN-γ, IL-12, IL-5, and IL-17 (R&D, Minneapolis, Minn.). Cells were then incubated at 37° C. in 5% $CO_2$ in the presence of each of the identified peptides pools (Table 2) at 1 μg/ml for four days. *Pneumocystis* antigen and ovalbumin (OVA) proteins were used as positive and negative controls. Spot frequencies of IFN-γ, IL-5, and IL-17 were developed following the manufacturer's instructions and spot forming units were scanned and calculated by Cellular Technology Ltd. plate reader and its spot calculation software.

Recombinant Meu10 Expression

The *P. murina* Meu10 sequence was synthesized (DNA2.0) and cloned into a pBudCE4.1 vector under the control of a CMV-promoter. The construct also contained a C-terminal myc tag. 293 cells were then transfected with using a neon transfection system (Life Technologies) under the following parameters: 1,500 V, 30 ms, 1 pulse. Cells were then lysed using cell lysis buffer (Cell Signaling) plus protease inhibitors and were subsequently sonicated. 293 lysate was harvested as a control.

Myc-Tag Detection by Western Blot

Cell lysates were boiled at 95° C. in 1× lithium dodecyl sulfate (LDS) buffer and 20 μL of each sample was loaded onto 4-20% Bis-Tris gel (Bio-Rad) and run at 200V for 30 minutes. Samples were then transferred to a Mini Trans-Blot (Bio-Rad). The membrane was then washed with TBST, blocked with TBST plus 5% dry milk, and stained overnight at 4° C. with 1:1000 rabbit anti-myc antibody (Cell Signaling). Following three washes with TBST, the membrane was incubated for two hours in anti-rabbit IgG conjugated to HRP (Cell Signaling). The membrane was washed three additional times and developed using Pierce chemiluminescent substrate (Thermo Scientific).

Recombinant Meu10 ELISA

Cell lysates (150 ng/well) in coating buffer were then added to a 96-well plate and incubated at 4° C. overnight. Plates were then washed, blocked with PBST plus 5% dry-milk, and stained with 1:1000 diluted *P. murina* convalescent serum or naïve serum overnight at 4° C. Plates were washed, stained with goat anti-mouse IgG (Southern Biotech), washed, and developed with TMB substrate. Absorbance was measured at 450 nm and groups were compared using unpaired Student's t test.

*P. murina* Immunofluorescence

*P. murina* samples were heat-fixed onto glass slides, followed by further fixation using ice-cold methanol. Slides were washed with PBS and blocked for 15 minutes in PBS with 5% dry milk. Anti-Meu10 serum (generated from mice immunized with the Meu10 peptide pool) was diluted 1:1000 in PBS and added to the slides for 15 minutes. Following PBS washes, slides were stained with 1:1000 diluted goat anti-mouse IgG conjugated to DyLight 488 (Thermo Scientific). Slides were washed with PBS, counterstained with DAPI (4',6-diamidino-2-phenylindole; diluted 1:2000 for 15 minutes), washed again and coverslips were mounted with VectaMount AQ mounting media (Vector Laboratories). Slides were visualized using 63× magnification.

Statistics

All data are presented as the mean±SEM. Statistical analysis was performed with a commercially available statistical software program (GraphPad Prism; GraphPad Software Inc.). ELISPOT™ data were tested by one-way ANOVA applied with Dunnett's multiple comparisons test. ELISA data were analyzed using unpaired Student's t test. P values of less than 0.05 were considered statistically significant.

Results

As there is no sufficient culture system to propagate *P. murina* or any other *Pneumocystis* species outside of their respective host organisms, it was necessary to generate a highly pure preparation of *P. murina* organisms to minimize contaminating mouse proteins. To achieve a high purity sample of *P. murina* in BAL, the organism was propagated in highly immunodeficient $Rag2^{-/-}Il2rg^{-/-}$mice, which lack mature B cells, T cells, and functional NK cells, and support high levels of *P. murina* growth (Kelly et al., *J Immunol* 190:285-295, 2013). To minimize mouse protein contamination, *P. murina* was recovered from infected mice by bronchoalveolar lavage. *Pneumocystis* organisms were then purified by differential centrifugation and extensively washed by PBS. Histological stains of the resulting *P. murina* preparations contained a very high burden of both the ascus or cyst form and the trophic form of the organism, with relatively few contaminating mouse cells, predominantly alveolar macrophages. Using flow cytometry analysis and these samples, the proportion of host cells was shown by anti-mouse CD45 and anti-mouse CD326 staining to be less than 1%.

Identification of *P. murina* Peptides

About 3820 tandem mass spectra were collected in a LC-MS analysis of peptide mixture eluted from an avidin column. One third of these 3820 (~1200) could be identified on the peptide spectra, as only a small portion of the spectra led to unambiguous peptide identification. After database searches performed on the raw data set (containing about 3820 tandem mass spectra) against the recently released *P. murina* draft protein sequence database and the mouse protein sequence database, 36 host (mouse) proteins were identified with 49 labeled peptides, and the final number of identified *P. murina* proteins was 33 with 113 labeled peptides.

Since MSGs are extensively studied and known to be an abundant set of surface proteins in *Pneumocystis*, detection of the cell surface exposed areas of MSGs can serve as an internal validation that the proteins identified by the cell surface labeling approach are on the cell surface or associated with the cell surface. To this end, eight MSG family members were identified. FIG. 1A shows a representative tandem mass spectrum of one representative MSG protein, which identified the peptide FPEK*IEVENLYK (SEQ ID NO: 105), an exposed peptide sequence. Characteristic fragments arising from the labeling reagent further confirmed that the peptide sequences were biotin labeled and therefore present on the cell surface. In this peptide sequence, it was unambiguously determined that the lysine residue proximal to the N-terminus (denoted by K* in FPEK*IEVENLYK; SEQ ID NO: 106) was modified by the biotin labeling reagent.

In addition to identifying eight MSGs, a number of *P. murina* transmembrane proteins were identified with labeled surface peptide, as predicted by Tied Mixture Hidden Markov Model (TMHMM) analysis. For example HGQIEVTCAK*SGIYENSLWYIEDNS (SEQ ID NO: 107), a peptide putatively expressed on the outside of the *P. murina* glycosyltransferase family 39 protein was identified (FIG. 1B).

MHC Class II Epitope Analysis for Identified *P. murina* Antigen

Using the cell surface labeling and LC-MS approach, a number of potential protein candidates were identified through searching the NCBI RefSeq database of fungal protein prior to the release of the *Pneumocystis* genome from the Broad Institute. Since the *P. murina* genome was not released at the beginning of this work, eight protein sequences were selected from *P. carinii, S. pombe* and *S. cerevisiae* for further study (Table 1). Protein candidates were chosen using various criteria including predicted participation in vital cellular processes, such as cell wall assembly, potential function as virulence or survival factors, and predicted surface location using the TMHMM model. Proteins such as 1, 3-β-glucan synthase GSC-1 (GSC-1), GPI-anchored cell surface protein involved in ascospore wall assembly Meu10 (Meu10) and 1,3-beta-glucanosyltransferase Gas4 of *Saccharomyces pombe* (Gas4p) may play key roles in cell wall assembly and sporulation. The hexose transporter Ght5 (Ght5) and vacuolar membrane amino acid uptake transporter Fnx1 (Mfs1), a member of the major facilitator superfamily, participate in membrane transport and metabolism. Finally, ATPase beta subunit (ATP2) and sterol 24-C-methyltransferase Erg6 (Erg6) were chosen for their potential roles in energy metabolism and biosynthesis of sterols, respectively. Also while conducting this work there were ongoing advances in the *P. murina* and *P. jirovecii* genomes (Ma et al., *FASEB J* 27:1962-1972, 2013) and among the proteins listed in Table 1, GSC-1, Meu10, Erg6, Gas4, and Mfs1 are conserved in *P. jirovecii* with 92, 50, 76, 64, and 62% homology respectively. Some identified proteins like GSC-1 have been reported previously in *P. carinii* (Kottom et al., *J Biol Chem* 288:23893-23902, 2013; Puckett et al., *Miss Dent Assoc J* 42:12-13, 24, 1986).

T Cell Responses to MHC Class II-Binding Peptides

Figure 2:
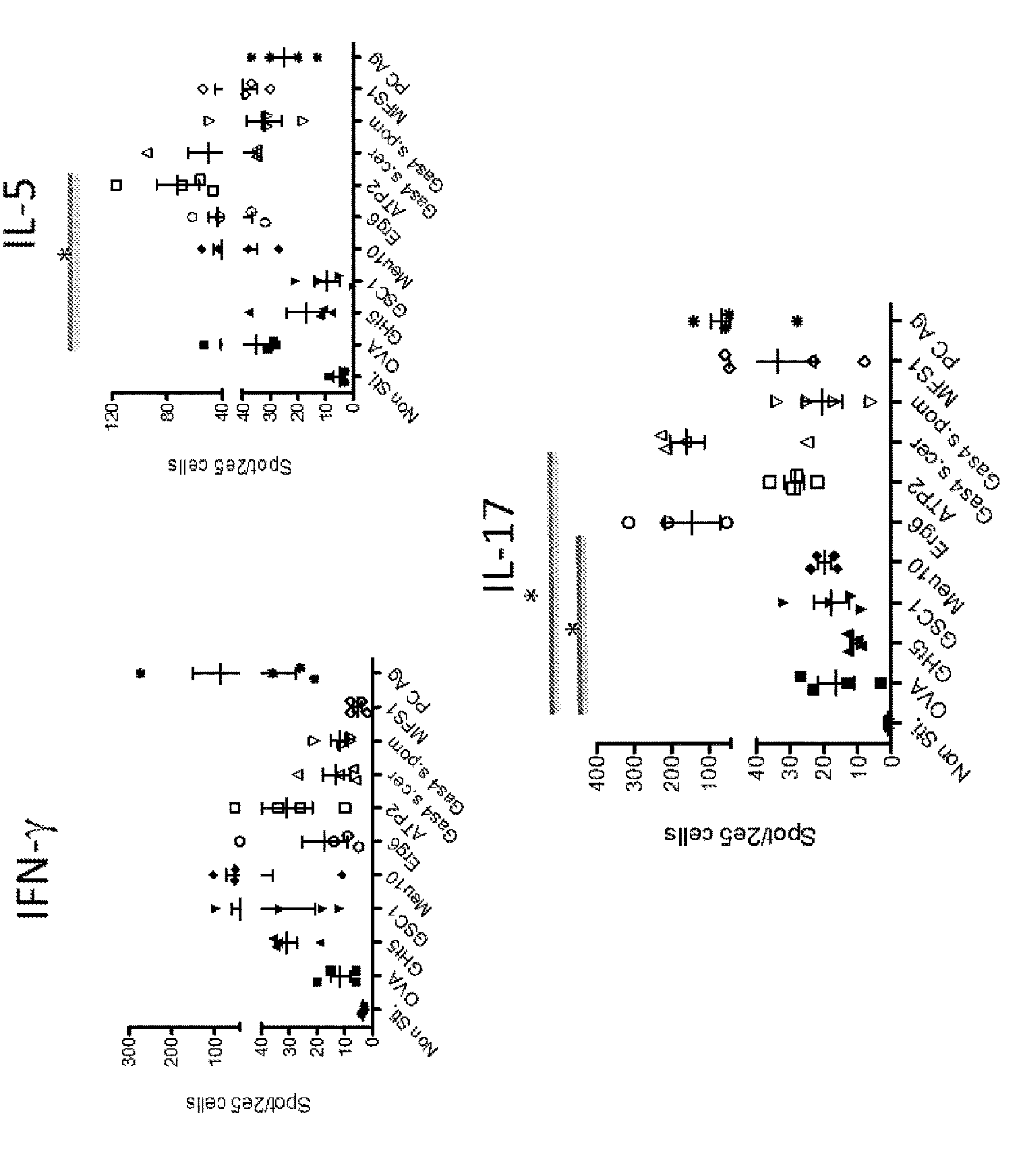
FIG. 2: Response of CD4+ T cell subsets to peptide stimulation. C57/B6 wt mice were inoculated with *Pneumocystis* for two weeks. Total lymphocytes from lung draining lymph node were stimulated by each peptide pool (see Table 2) and control proteins in vitro for four days. Spot frequency of interferon (IFN)-γ, interleukin (IL)-5, and IL-17 were determined as spot-forming units/$2\times10^5$ cells as plotted. All data are reported as mean±SEM for n=4 per group. One-way ANOVA was applied with a Dunnett's multiple comparison test. *, P<0.05. Non-Sti., nonstimulated; s. cer, *S. cerevisiae*; s. pom, *S. pombe*; PC Ag, *Pneumocystis* antigen.

After identifying putative MHC class II-binding peptides for each potential *Pneumocystis* protein listed in Table 1, it was tested if these proteins elicit T-cell responses during natural *P. murina* infection by ELISPOT™ (FIG. 2). Fourteen unique peptides of 15 amino acids in length were chosen for the genes ATP2, *S. cerevisiae* Gas4, *S. pombe* Gas4, and Mfs1, and 10 peptides were chosen for Ght5, GSC-1, Meu10, and Erg6 (Table 2). The peptides for each protein were pooled together and tested for stimulation of lung draining lymph node T cells by ELISPOT™. T cells were also stimulated with whole *Pneumocystis* antigen and chicken OVA as positive and negative controls, respectively. Spot frequency of IFN-γ, IL-5, and IL-17 producing cells, corresponding to Th1, Th2, and Th17 subsets, were determined and plotted as spot forming units/2×10$^5$ cells (FIG. 2). The majority of peptide pools showed a stimulation response in C57BL/6 mice for each of the three cytokines compared to OVA protein, indicating that these peptide pools contain immunogenic epitopes that are able to bind MHC class II. Although many of the peptides elicited a Th1 response compared to no stimulation, none were significant compared to OVA. However, ATP2 elicited a strong IL-5 response and both Erg6 and Gas4 elicited a Th17 response.

Humoral Response to Identified *P. murina* Antigen

Figure 3A:
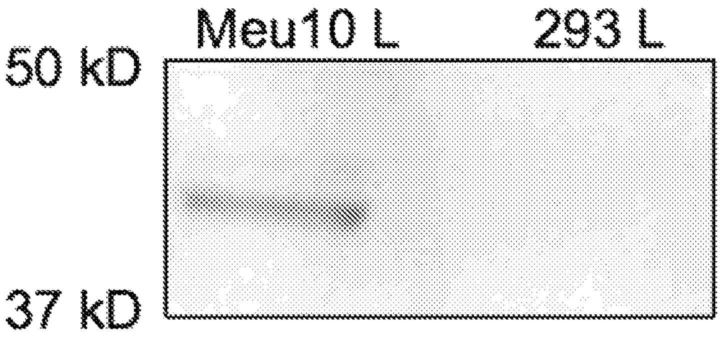
FIGS. 3A-3B: Meu10 is an extracellular antigen capable of inducing a humoral immune response.
Figure 3B:
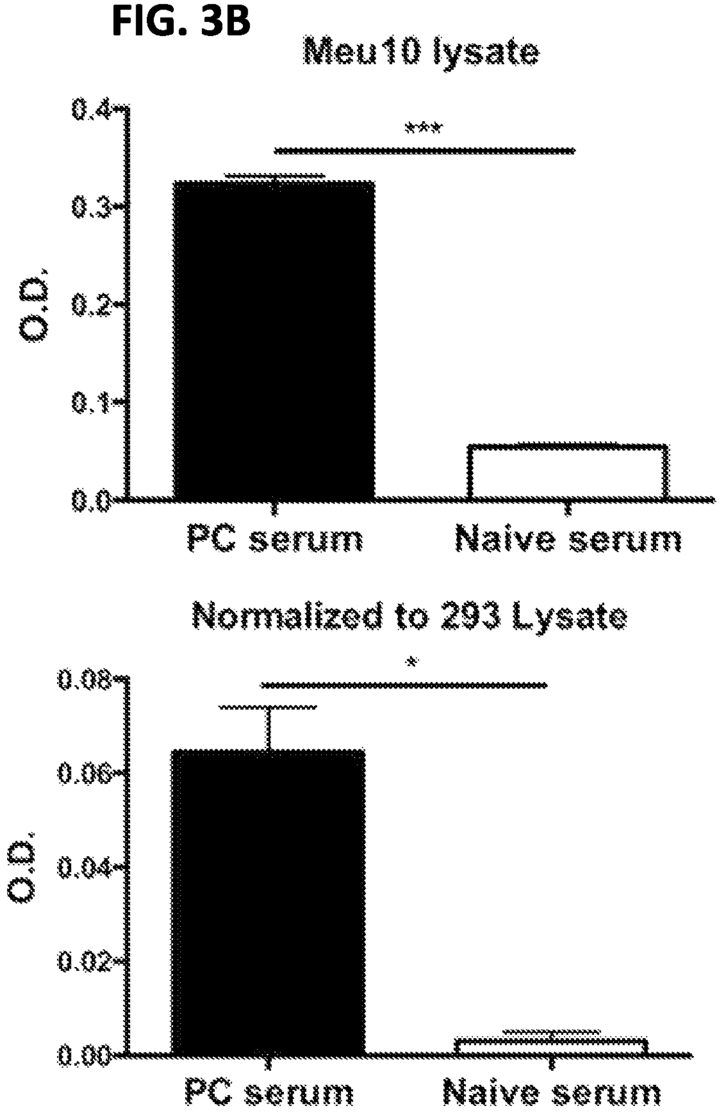

To further examine the antigenic potential of the proteins identified by surface biotinylation, the humoral immune response to one antigen, Meu10, was analyzed as TMHMM analysis predicted it to be a type I transmembrane protein with a glycosylphosphatidylinositol (GPI) anchor. Meu10 recombinant protein from 293 cell lysate could be easily identified by Western blot targeting the C-terminal myc tag (FIG. 3A). Furthermore, serum from natural *P. murina* infection recognized the Meu10 cell lysate by ELISA when compared to naïve serum (p=0.009) (FIG. 3B). This could be further validated by normalizing the optical density to the background of non-transfected 293 cell lysate, in which case the *P. murina* convalescent serum still had increased recognition of the Meu10 lysate (p=0.024) (FIG. 3B). Finally, anti-Meu10 serum generated by a C57BL/6 mouse stained the extracellular surface of both the *Pneumocystis* cyst and troph, while naïve serum showed very little specific staining. Taken together, these results further confirm the validity of surface biotinylation, as Meu10 is an extracellular antigen capable of inducing a humoral immune response during natural *Pneumocystis* infection.

Applications

Antigen discovery in *Pneumocystis* has been constrained in part by the inability to culture the organism ex vivo. Antigens have been historically discovered by generation of monoclonal antibodies and subsequent protein purification (Gigliotti et al., *J Infect Dis* 154:315-322, 1986; Wells et al., *Infect Immun* 72:1548-1556, 2004), as well as the generation of polyclonal antibodies and proteomics using immunoprecipitation separation by 2-D gel electrophoresis (Zheng et al., *J Clin Invest* 108:1469-1474, 2001; Zheng et al., *J Clin Invest* 115:3536-3544, 2005). These techniques can identify potentially therapeutic or diagnostic targets, but they are limited by having the proper antibodies. Moreover, the above techniques are not limited to surface proteins which may have the most therapeutic potential. The cellular surface of *P. murina* is the site of host-pathogen interaction and plays a key role in fungal adhesion, disease progression, and recognition of the pathogen by the host immune system (Steele et al., *J Exp Med* 198:1677-1688, 2003; Rapaka et al., *J Exp Med* 207:2907-2919, 2010; Ricks et al., *Infect Immun* 81:3451-3462, 2013). Surface components of *P. murina* and other fungal cells include cell wall molecules such as glycoproteins in addition to other surface proteins, polysaccharides, and lipids. Further elucidation of the molecular composition of the *P. murina* cell surface, and particularly the surface proteome, may reveal novel immunogens and potential targets for new antifungal therapies. Surface proteomics in other culturable yeasts have been previously described (Qian et al., *Anal Bioanal Chem* 392: 439-449, 2008) and thus it was hypothesized that this technique can be adapted to non-culturable fungi such as *Pneumocystis.*

To optimize this technique, it was important to use a host strain that supported high growth of the organisms. It has been previously shown that Rag2$^{-/-}$Il2rg$^{-/-}$mice support 2-3 log higher *Pneumocystis* growth than Rag2−/− or SCID mice (Qian et al., *Anal Bioanal Chem* 392:439-449, 2008). The use of Rag2$^{-/-}$Il2rg$^{-/-}$mice also allowed purification of the organism from BAL fluid. The surface biotinylation technique was efficient in identifying putative surface proteins as many of the identified proteins were members of the major surface glycoprotein family, while the non-MSG proteins had predicted surface topology using TMHMM analysis. Some of these proteins contain CD4+ T-cell epitopes, as ELISPOT™ reactivity was observed against some of these proteins in CD4+ T cells harvested from draining lymph nodes two weeks after infection.

In addition to identifying CD4+ T-cell epitopes this technique also identified novel B-cell epitopes such as Meu10, which is a GPI-anchored protein that appears to be on the surface of both the troph and cyst. This protein is conserved in *P. murina* and *P. jirovecii* and based on its large ectodomain, represents an attractive target as a vaccine antigen or a target for therapeutic monoclonal antibodies.

Example 2: Further Characterization of Meu10

Figure 4:
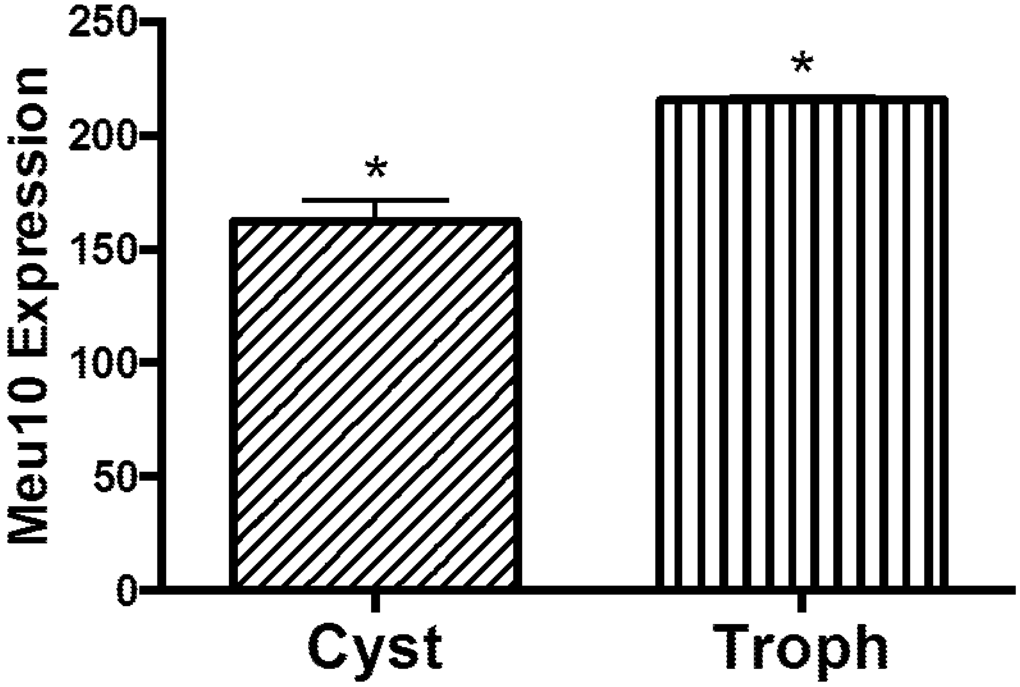
FIG. 4: Meu10 expression. RNA sequencing on separated *P. murina* life forms (cysts and trophs) demonstrated Meu10 is expressed in both life forms, and 1.3-fold higher in the replicative troph form (*, p<0.05).

The Meu10 protein is involved in ascospore formation. RNA sequencing on separated *P. murina* life forms (cysts and trophs) demonstrated Meu10 is expressed in both life forms, with 1.3-fold greater expression in the replicative troph form (FIG. 4). Meu10 is conserved between *P. murina* and *P. jirovecii* (total conservation between the two proteins is 53%). TMHMM analysis of *P. jirovecii* Meu10 revealed a similar transmembrane topology as *P. murina* Meu10.

Figure 5:
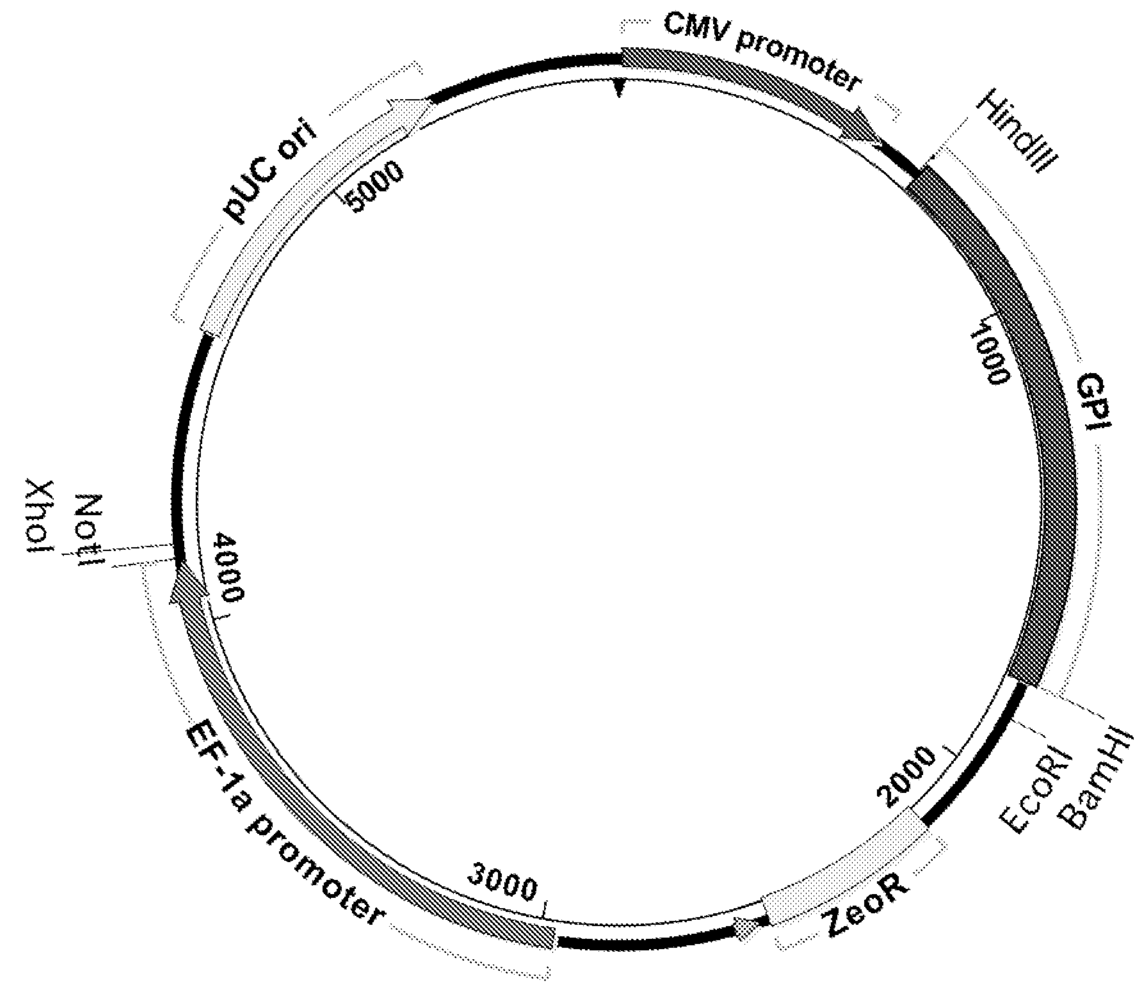
FIG. 5: Schematic of Meu10 containing pBUDCE4.1 DNA expression vector. The *P. murina* Meu10 sequence (labeled GPI) was inserted using the HindIII and BamHI restriction sites and is under the control of a 5' cytomegalovirus (CMV) promoter. At the 3' end of the Meu10 sequence is a histidine and myc tag, used to identify recombinant protein.

To evaluate whether DNA vaccination with a nucleic acid molecule encoding Meu10 was capable of inducing a Meu10-specific immune response, a vector containing the coding sequence of *P. murina* Meu10 was constructed. As shown in FIG. 5, the Meu10 coding sequence was inserted into the pBUDCE4.1 DNA expression vector using the HindIII and BamHI restriction sites. The *P. murina* Meu10 sequence was placed under the control of a 5' CMV promoter. A histidine and myc tag, used to identify recombinant protein, was placed at the 3' end of the Meu10 sequence.

Figure 6:
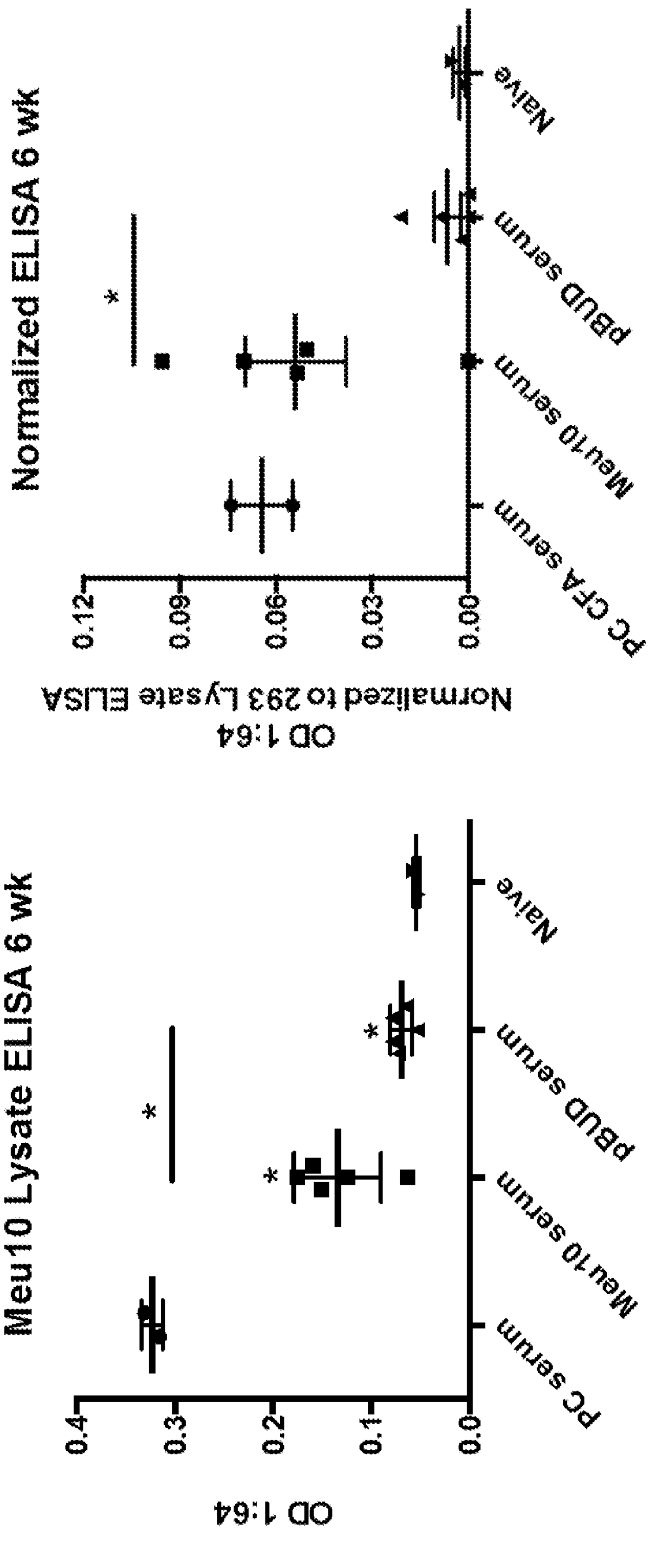
FIG. 6: Meu10 DNA vaccination generates Meu10-specific IgG antibodies. Meu10 recombinant protein was made by transfecting 293 T cells with the Meu10-containing pBUD expression vector and cell lysates were harvested 48 hours post-transfection. Cell lysates were used to coat 96-well plates. Serum was collected from mice infected with *Pneumocystis* (PC serum), mice immunized with Meu10, mice immunized with pBUD, or naïve mice. Serum was used as the primary antibody and was detected using a goat anti-mouse anti-IgG conjugated to horseradish peroxidase (HRP). The panel on the left demonstrates that PC serum and Meu10 immunized serum recognize Meu10 lysate, which remained the case after normalization to the background of 293 lysate (right panel).

Studies were performed to determine whether the Meu10 DNA vaccine (SEQ ID NO: 108) could generate Meu10-specific IgG antibodies. Meu10 recombinant protein (SEQ ID NO: 109) was made by transfecting 293 T cells with the Meu10-containing pBUD expression vector and cell lysates were harvested 48 hours post-transfection. Cell lysates were used to coat 96-well plates. Serum was collected from mice infected with *Pneumocystis*, mice immunized with Meu10, mice immunized with pBUD, and naïve mice. Serum was used as the primary antibody and was detected using a goat anti-mouse anti-IgG conjugated to HRP. The results demonstrated that *Pneumocystis* serum and Meu10 immunized serum recognized Meu10 lysate, which remained the case after normalization to the background of 293 lysate (FIG. 6).

Figure 7:
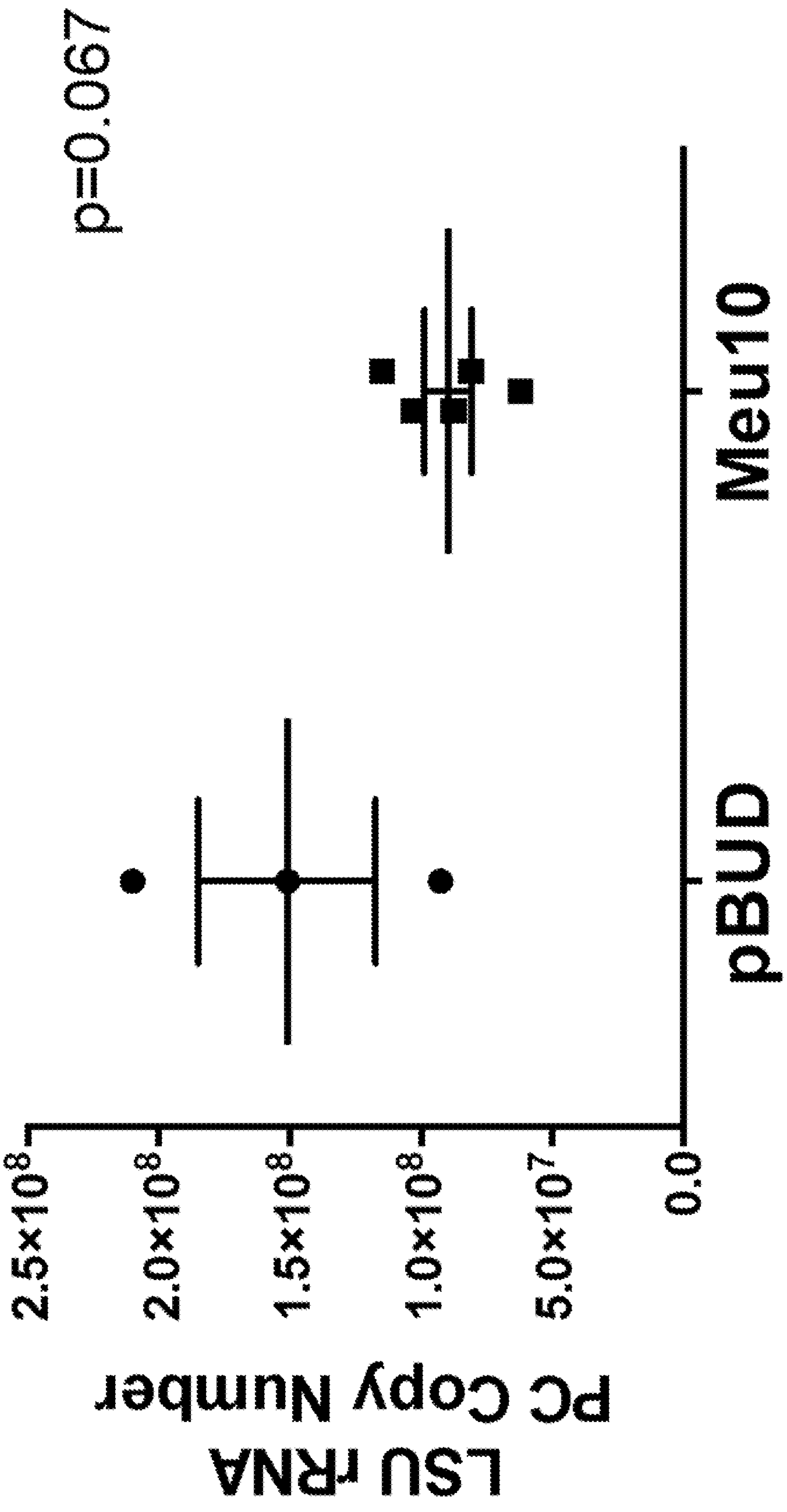
FIG. 7: Meu10 DNA vaccination provides protection against *Pneumocystis* challenge. Following three doses of intramuscular vaccination with the Meu10 DNA vaccine and immunodepletion with GK1.5 monoclonal antibody, mice were challenged with *Pneumocystis* and sacrificed 6 weeks post-infection. Mice vaccinated with Meu10 had a trend towards decreased *Pneumocystis* burden when compared to empty pBUD (control) vaccinated mice.
Figure 8:
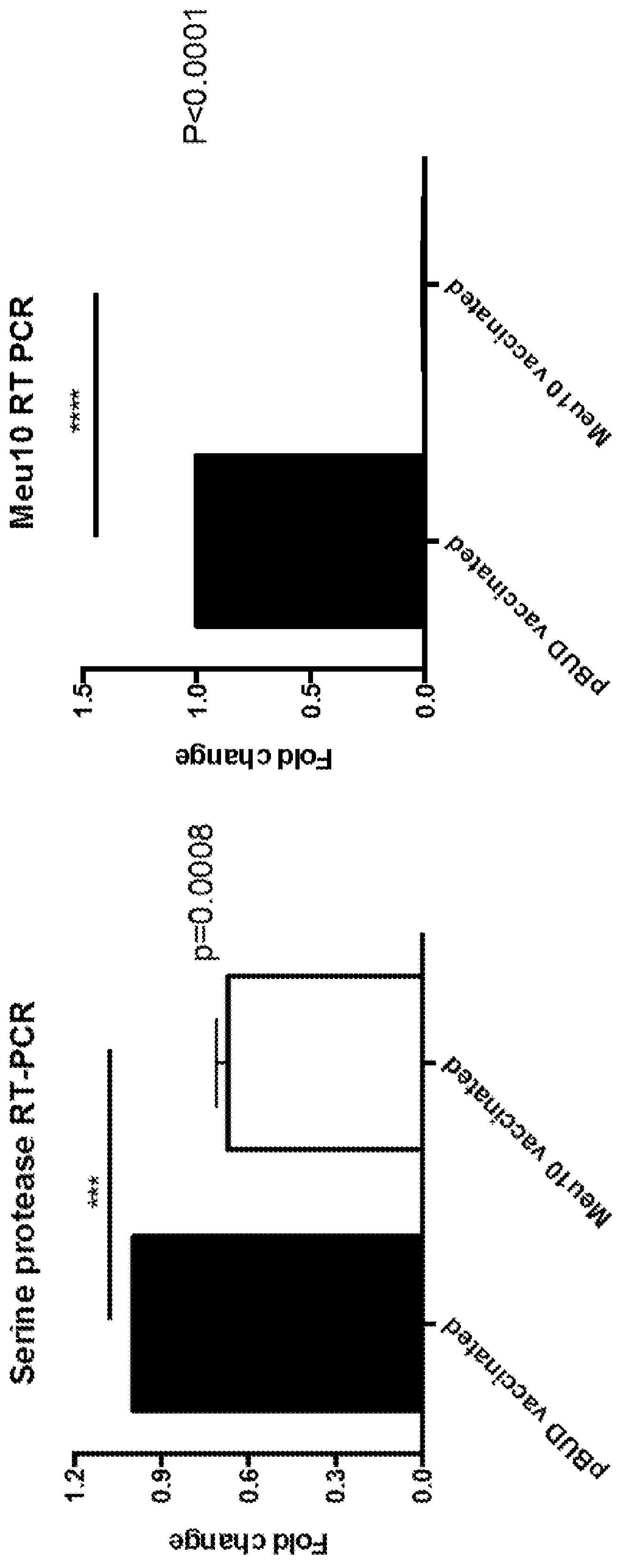
FIG. 8: Meu10 DNA vaccination decreases troph-specific gene expression. Real-time PCR on lung homogenate RNA recovered from Meu10 or empty pBUD vector vaccinated mice demonstrates Meu10 vaccinated animals exhibit decreased expression of a putative serine protease transcript (found to be troph-specific) and Meu10.

Next, a study was conducted to determine whether Meu10 DNA vaccination provides protection against *Pneumocystis* challenge. Mice were administered three doses of the Meu10 DNA vaccine intramuscularly and immunodepleted with GK1.5 monoclonal antibody. Mice were then challenged with *Pneumocystis* and sacrificed 6 weeks post-infection. Mice vaccinated with Meu10 had a trend towards decreased *Pneumocystis* burden when compared to empty pBUD (control) vaccinated mice (FIG. 7). Meu10 DNA vaccination also decreased troph-specific gene expression. Real-time PCR on lung homogenate RNA recovered from Meu10 or empty pBUD vector vaccinated mice demonstrated Meu10 vaccinated animals have decreased expression of Meu10 and a putative serine protease transcript (found to be troph-specific).

Figure 9:
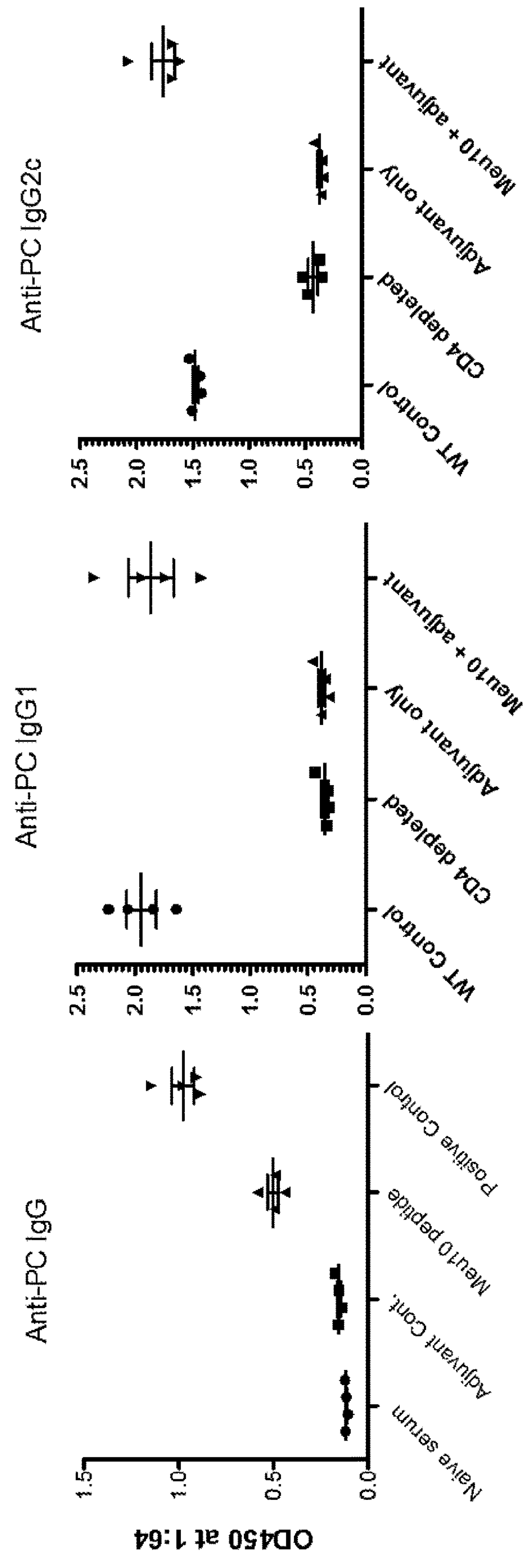
FIG. 9: Meu10 peptide vaccination generates *Pneumocystis*-specific and Meu10-specific IgG antibodies. Meu10 recombinant protein was made as described in Example 1. Meu10 lysate or *Pneumocystis* antigen was used to coat 96-well plates. Serum was collected from CD4-depleted mice infected with *Pneumocystis* (PC serum), mice immunized with Meu10 and adjuvant, mice receiving adjuvant alone, or wild type mice. Serum was used as the primary antibody and was detected using a goat anti-mouse anti-IgG conjugated to HRP. Meu10 vaccinated mice demonstrate anti-*Pneumocystis* total IgG prior to challenge (left), and show strong IgG1 (middle) and IgG2C (right) antibody responses following challenge.

Further studies were conducted to test the effect of Meu10 peptide vaccination. Meu10 recombinant protein was made as described in Example 1. Meu10 lysate or *Pneumocystis* antigen was used to coat 96-well plates. Serum was collected from CD4-depleted mice infected with *Pneumocystis*, mice immunized with Meu10 and adjuvant, mice receiving adjuvant alone, or wild type mice. Serum was used as the primary antibody and was detected using a goat anti-mouse anti-IgG conjugated to HRP. Meu10 vaccinated mice exhibited anti-*Pneumocystis* total IgG prior to challenge, and showed strong IgG1 and IgG2C antibody responses following challenge (FIG. 9).

Figure 10:
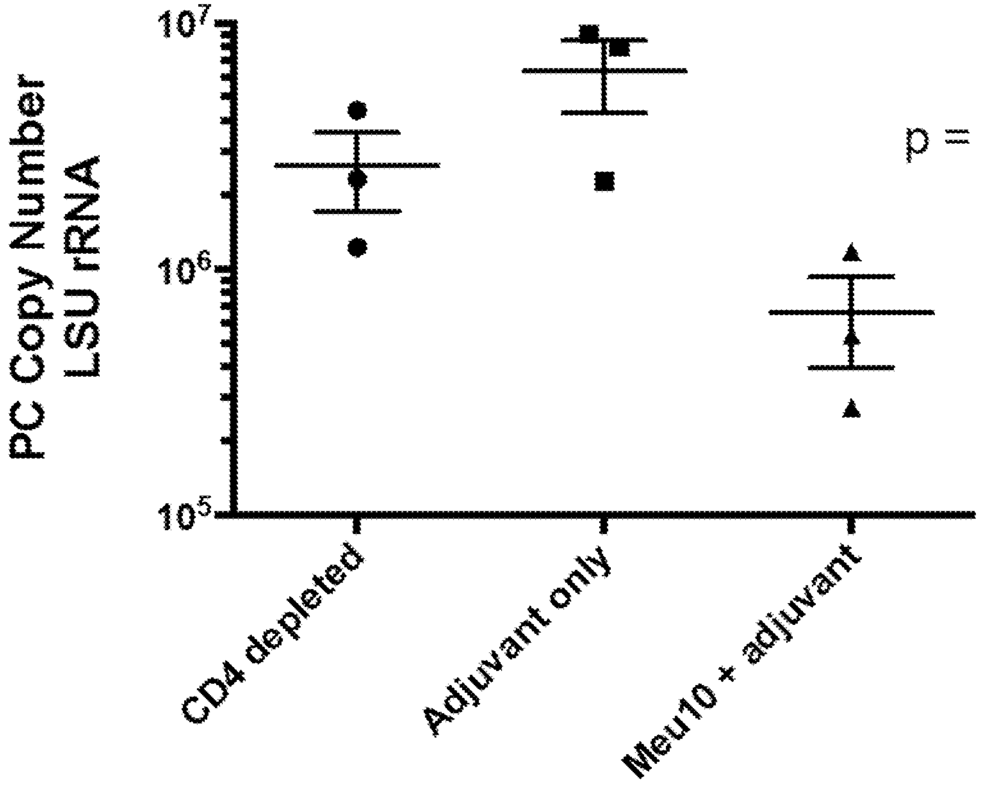
FIG. 10: Meu10 peptide vaccination provides protection against *Pneumocystis* infection. Mice were immunized with two doses of Meu10 peptide and Sigma Adjuvant System (oil) by intraperitoneal injection or with adjuvant alone. Mice were then immunodepleted using GK1.5 monoclonal antibody and challenged with *Pneumocystis*. Four weeks following infection, mice were sacrificed and RT-PCR for *Pneumocystis* large subunit rRNA (LSU rRNA) was performed from RNA isolated from lung homogenate.
Figure 11:
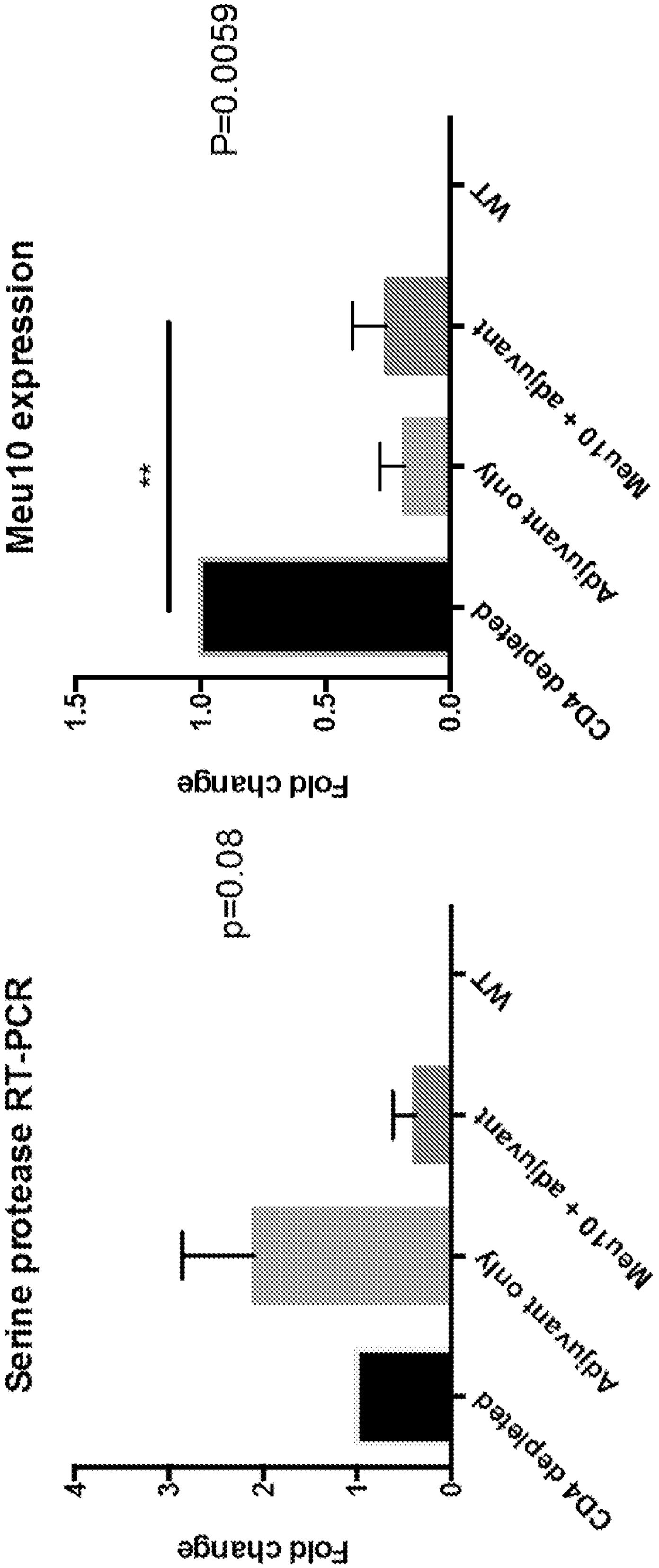
FIG. 11: Meu10 peptide vaccination decreases troph-specific gene expression. Real-time PCR on lung homogenate demonstrates Meu10 vaccinated animals have decreased expression of a putative serine protease transcript (found to be troph-specific) and Meu10, when compared to mice treated with adjuvant only or with CD4-depleted mice.

Additional studies demonstrated that Meu10 peptide vaccination provided protection against *Pneumocystis* infection. Mice were immunized with two doses of Meu10 peptide and Sigma Adjuvant System (oil) by intraperitoneal injection or with adjuvant alone. Mice were then immunodepleted using GK1.5 monoclonal antibody and challenged with *Pneumocystis*. Four weeks following infection, mice were sacrificed and RT-PCR for *Pneumocystis* large subunit rRNA was performed from RNA isolated from lung homogenate. As shown in FIG. 10, mice vaccination with Meu10 peptide had a decrease in *Pneumocystis* large subunit rRNA. Meu10 peptide vaccination also decreased troph-specific gene expression. As shown in FIG. 11, Meu10 vaccinated animals exhibited decreased expression of Meu10 and a putative serine protease transcript (found to be troph-specific), when compared to mice treated with adjuvant only or with CD4-depleted mice.

Figure 12:
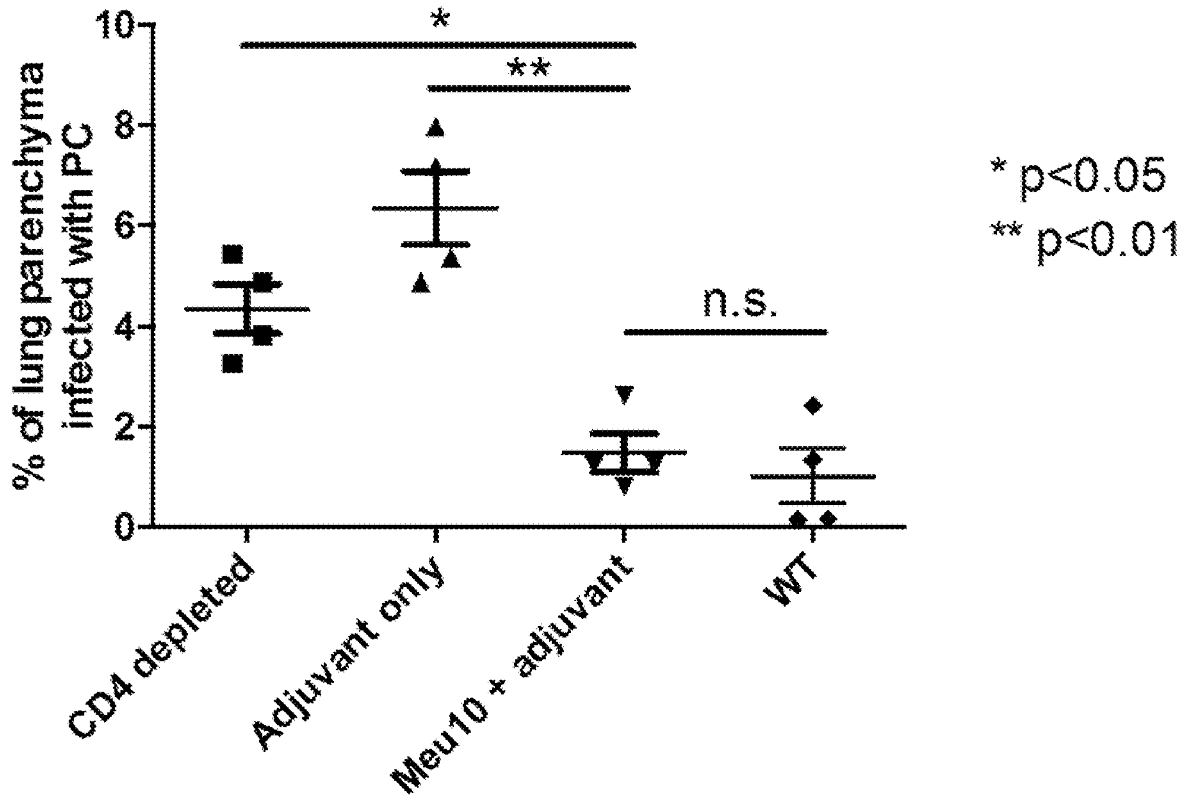
FIG. 12: Meu10 peptide vaccination decreases *Pneumocystis* burden on histology. Sections of lung were fixed and stained with GMS staining. *Pneumocystis* burden was quantified using ImageJ software. Meu10 vaccinated mice had significantly decreased *Pneumocystis* burden when compared to mice receiving adjuvant alone.

Furthermore, Meu10 peptide vaccination decreased *Pneumocystis* burden as assessed by histology. Sections of lung were fixed and stained with GMS staining. *Pneumocystis* burden was quantified using ImageJ software. Meu10 vaccinated mice had significantly decreased *Pneumocystis* burden when compared to mice receiving adjuvant alone (FIG. 12).

Example 3: Further Characterization of GSC-1

Figure 13:
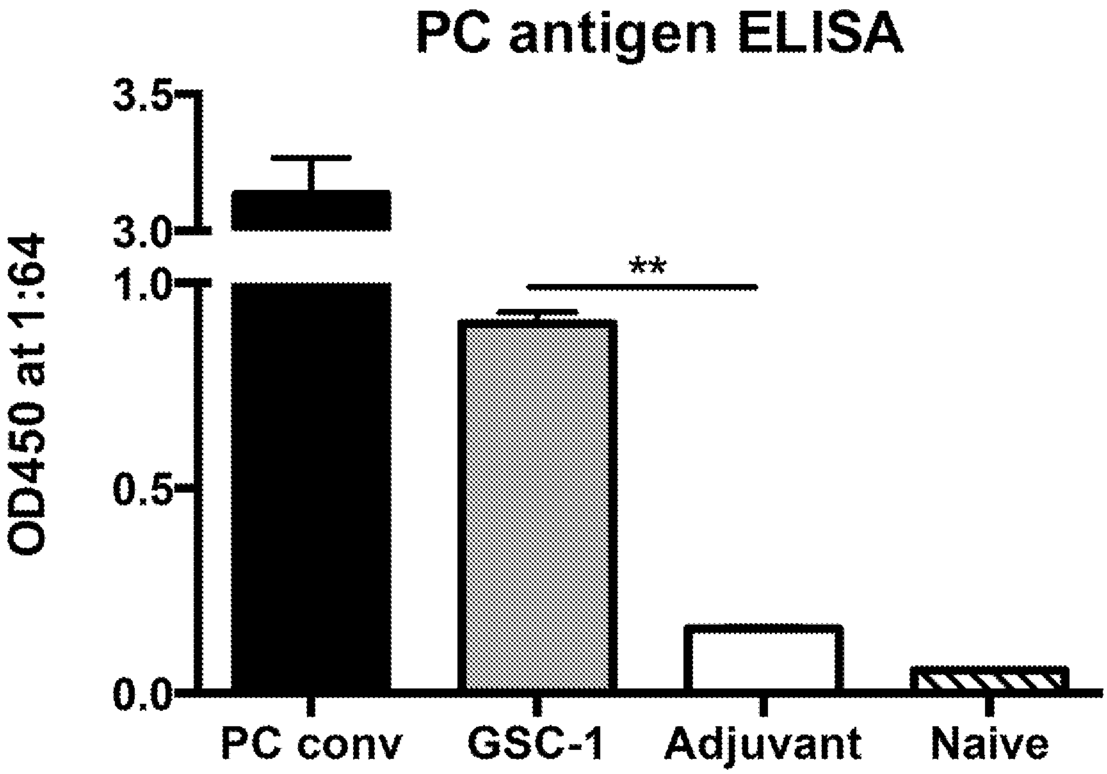
FIG. 13: Immunization with GSC-1 peptides generates anti-*Pneumocystis* IgG. Mice were immunized with one dose of a peptide pool of GSC-1 (SEQ ID NOs: 19-28) intraperitoneally and the presence of anti-*Pneumocystis* IgG was detected by ELISA 14 days post-immunization. Immunization resulted in the generation of anti-*Pneumocystis* IgG as measured by ELISA.

A GSC-1 peptide pool was generated (SEQ ID NOs: 19-28; see Table 2). Mice were immunized with one dose of the GSC-1 peptide pool intraperitoneally and the presence of anti-*Pneumocystis* IgG was detected by ELISA 14 days post-immunization. Immunization resulted in the generation of anti-*Pneumocystis* IgG as measured by ELISA (FIG. 13).

The GSC-1 protein was analyzed using TMHMM algorithms, which predict intracellular, transmembrane and extracellular domains. The analysis revealed that GSC-1 has a large, 600 amino acid ectodomain between residues 800 and 1400.

Figure 14:
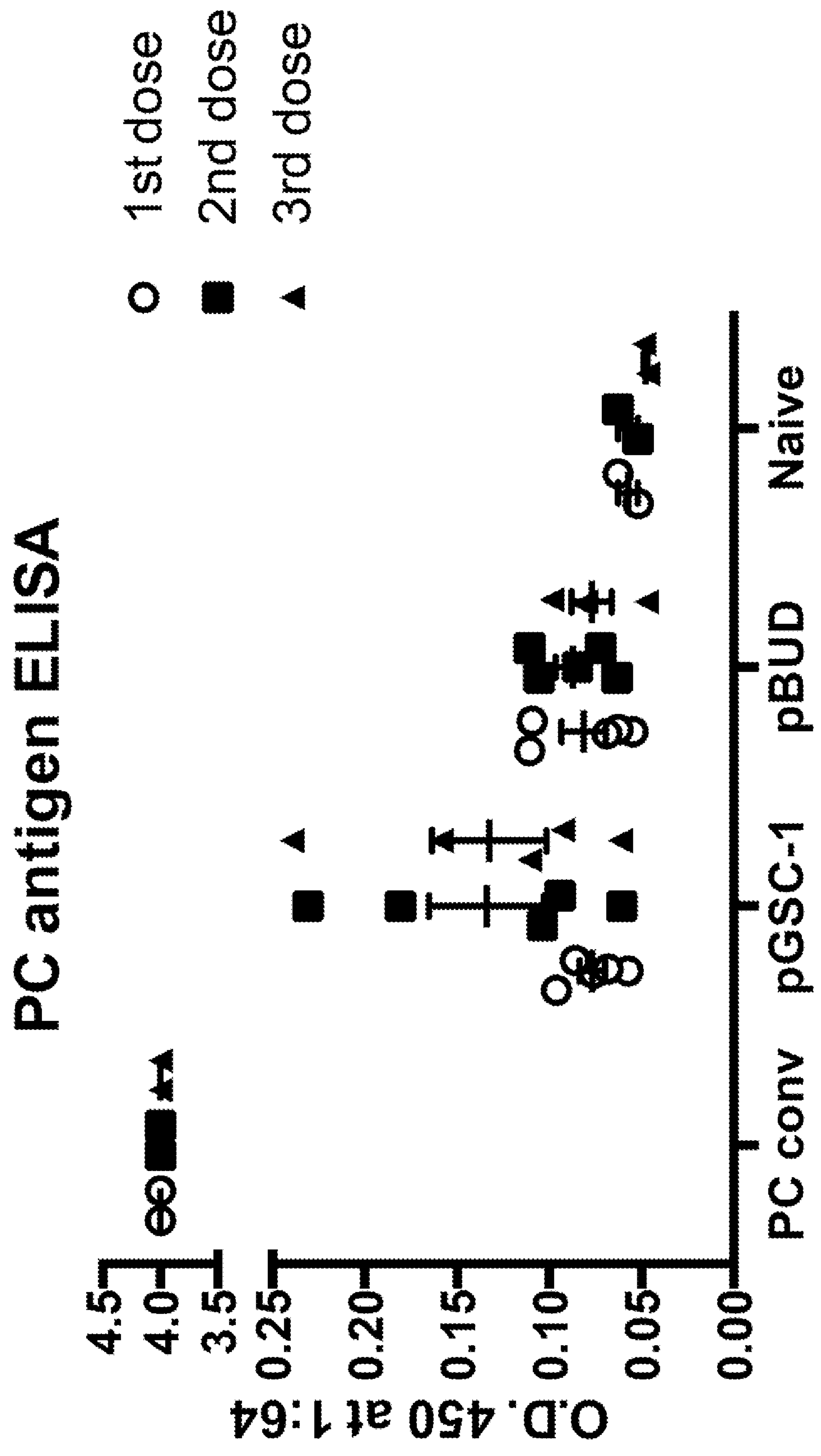
FIG. 14: Immunization with GSC-1 ectodomain DNA vaccine generates anti-*Pneumocystis* IgG. Mice were immunized with three doses of the GSC-1 ectodomain DNA vaccine in the pBUDCE4.1 vector (pGSC-1) using intramuscular injection followed by electroporation. Antibody titers were examined 14 days after each dose, and doses were given 14 days apart. Empty vector (pBUD) and naïve mice were used as negative controls; mice infected with *Pneumocystis* (PC conv) were used as positive controls. Repeat vaccination with the GSC-1 ectodomain DNA vaccine resulted in increased anti-*Pneumocystis* IgG.

A DNA vaccine encoding the GSC-1 ectodomain was generated (SEQ ID NO: 110). The DNA vaccine construct included an artificial leader sequence (nucleotides 11-73 of SEQ ID NO: 110) in frame with the coding sequence for the GSC-1 ectodomain (nucleotides 74-1822 of SEQ ID NO: 110). Mice were immunized with three doses of the GSC-1 ectodomain DNA vaccine in the pBUDCE4.1 vector using intramuscular injection followed by electroporation. Antibody titers were examined 14 days after each dose, and doses were given 14 days apart. Repeat vaccination with the GSC-1 ectodomain DNA vaccine resulted in increased anti-*Pneumocystis* IgG (FIG. 14).

Figure 15:
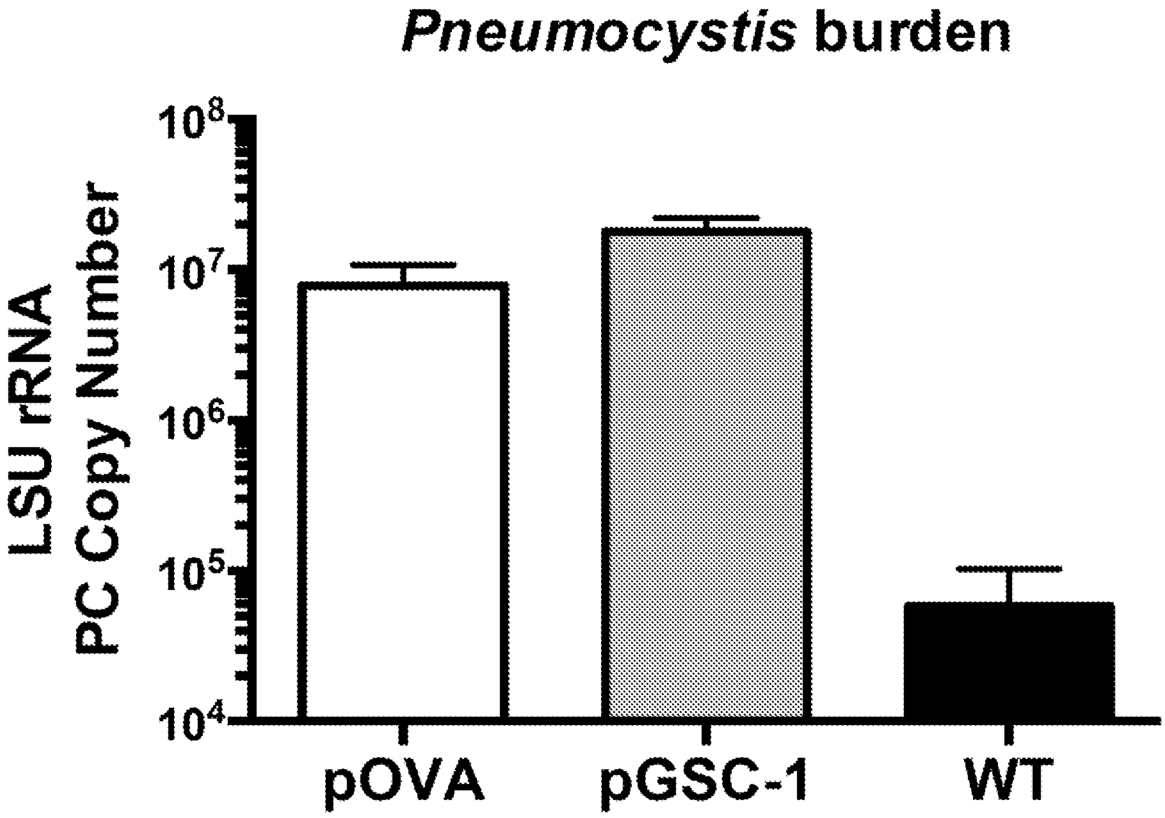
FIG. 15: Immunization with GSC-1 ectodomain DNA does not reduce *Pneumocystis* burden following primary challenge. Mice were immunized with GSC-1 DNA vaccine (pGSC-1) or a control vector (pOVA). Immunized mice were challenged with $2.0\times10^5$ *Pneumocystis* cysts following CD4-depletion with GK1.5 monoclonal antibody. After 28 days, mice were euthanized and *Pneumocystis* burden was analyzed by qRT-PCR for the large subunit rRNA.

An additional study demonstrated that immunization with the GSC-1 ectodomain DNA does not reduce *Pneumocystis* burden following primary challenge. Mice were immunized with pGSC-1 (ectodomain DNA vector) or pOVA (a control vector). Immunized mice were challenged with $2.0\times10^5$ *Pneumocystis* cysts following CD4-depletion with GK1.5 monoclonal antibody. After 28 days, mice were euthanized and *Pneumocystis* burden was analyzed by qRT-PCR for the large subunit rRNA. As shown in FIG. 15, rRNA copy number in mice vaccinated with pGSC-1 was not significantly different from mice vaccinated with the control vector.

Recombinant GSC-1 ectodomain protein (SEQ ID NO: 111) was generated using a *Saccharomyces cerevisiae* expression system. The GSC-1 ectodomain was cloned into the pYES-DEST52 expression vector and *S. cerevisiae* was transformed with the vector. Following growth of a starter culture, *S. cerevisiae* containing the GSC-1 vector was grown in media containing 2% galactose and 1% raffinose, which induces expression of GSC-1. Whole cell lysates were then prepared and analyzed for GSC-1 expression using anti-V5 Western blot for the recombinant tag. Western blot analysis demonstrated peak expression at 24 hours.

Figure 16:
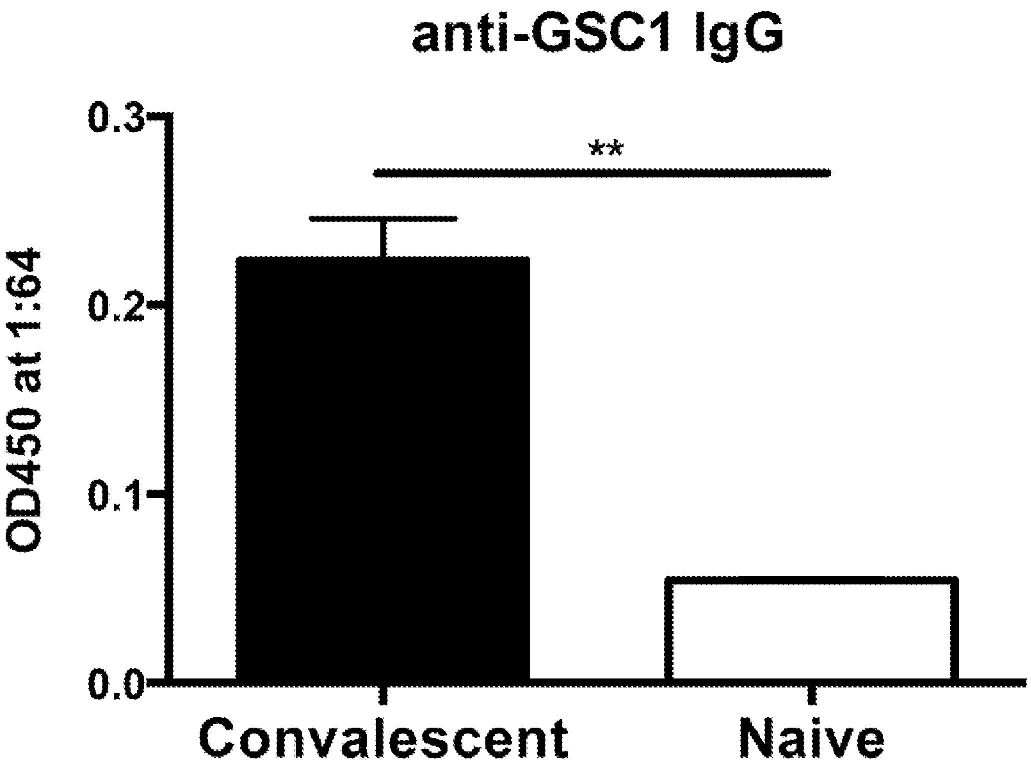
FIG. 16: Recombinant GSC-1 ectodomain is detectable by antibodies from mice infected with *Pneumocystis*. Recombinant GSC-1 was coated on a 96-well plate. Serum from mice infected with *Pneumocystis* (convalescent) or naïve mice was diluted 1:64 and was used to detect recombinant GSC-1 by ELISA. Mice previously infected with *Pneumocystis* made IgG against GSC-1, suggesting GSC-1 is a natural antigen seen throughout *Pneumocystis* infection. (** p<0.01 by student's T-test).

Studies were conducted to determine whether recombinant GSC-1 ectodomain is detectable by antibodies from mice infected with *Pneumocystis*. Recombinant GSC-1 was coated on a 96-well plate. Serum from mice infected with *Pneumocystis* (convalescent) or naïve mice was diluted 1:64 and was used to detect recombinant GSC-1 by ELISA. Mice previously infected with *Pneumocystis* made IgG against GSC-1, suggesting GSC-1 is a natural antigen seen throughout *Pneumocystis* infection. (FIG. 16).

An additional study demonstrated that mice immunized with recombinant GSC-1 generated anti-GSC-1 antibodies.

Figure 17:
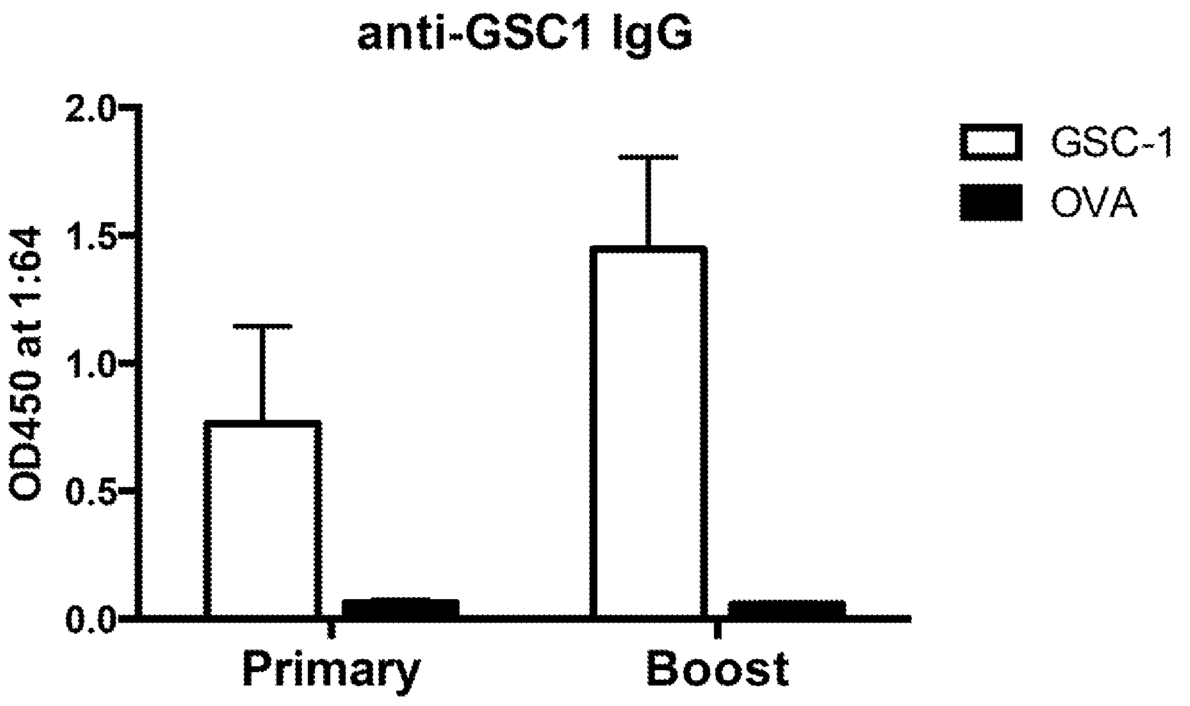
FIG. 17: Mice immunized with recombinant GSC-1 generated anti-GSC-1 antibodies. Twenty micrograms of GSC-1 (SEQ ID NO: 111) were administered through intraperitoneal injection in a 1:1 solution with alum. Fourteen days after primary immunization, the presence of antibodies were measured by ELISA and a second dose of GSC-1 in alum (boost) was given. Fourteen days following boost, antibodies were again measured by ELISA.

Twenty micrograms of GSC-1 were administered through intraperitoneal injection in a 1:1 solution with alum. Fourteen days after primary immunization, the presence of antibodies were measured by ELISA and a second dose of GSC-1 in alum (boost) was given. Fourteen days following boost, antibodies were again measured by ELISA. As shown in FIG. 17, anti-GSC-1 antibodies were detectable following both primary and boost vaccination, with an increase in anti-GSC-1 antibodies observed following the booster dose.

Figure 18:
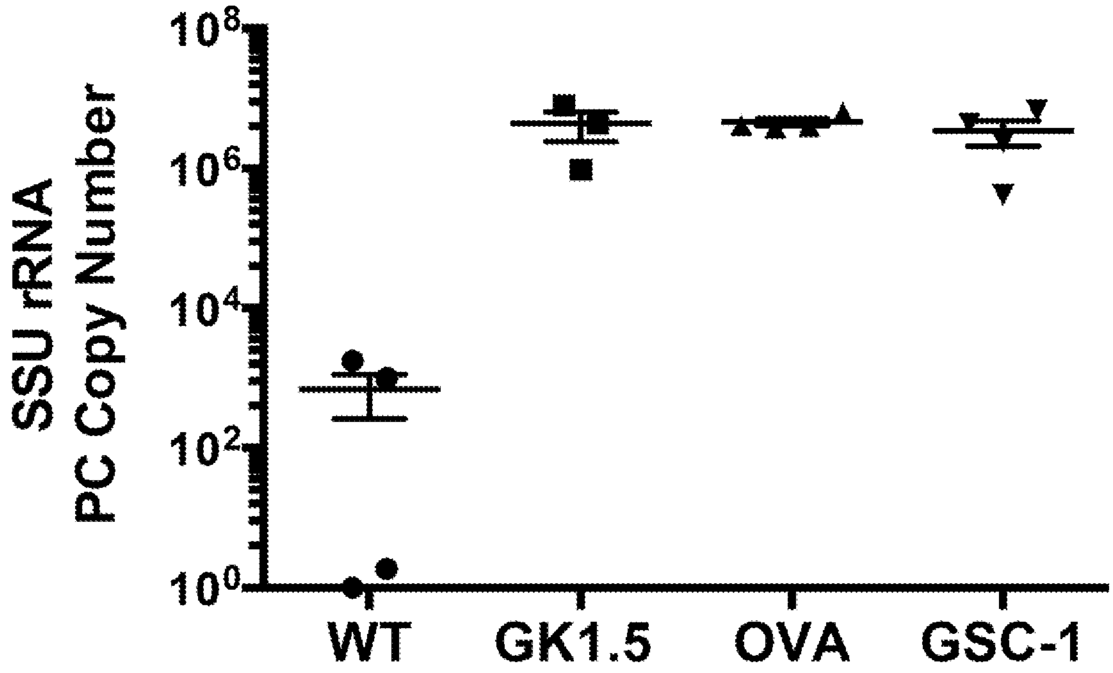
FIG. 18: Mice immunized with recombinant GSC-1 did not have reduced *Pneumocystis* burden following primary challenge. Following immunization with GSC-1 or control antigen (OVA), mice were CD4-depleted using GK1.5 monoclonal antibody and infected with $2.0\times10^5$ *Pneumocystis* cysts. Twenty-eight days post-infection, mice were euthanized and *Pneumocystis* burden was measured by qRT-PCR of the small subunit rRNA. Non-vaccinated WT mice and CD4-depleted mice (GK1.5) served as controls.

Despite the production of anti-GSC-1 antibodies, a reduction in *Pneumocystis* burden was not observed in recombinant GSC-1 immunized mice after primary challenge. Following immunization with recombinant GSC-1, mice were CD4-depleted using GK1.5 monoclonal antibody and infected with $2.0\times10^5$ *Pneumocystis* cysts. Twenty-eight days post-infection, mice were euthanized and *Pneumocystis* burden was measured by qRT-PCR of the small subunit rRNA. As shown in FIG. 18, rRNA copy number was not significantly altered in mice immunized with GSC-1 compared to mice immunized with a control vector (OVA) or non-immunized CD4-depleted mice.

An additional study found that mice immunized with recombinant GSC-1 had a reduction in cyst-specific markers, but not troph-specific markers. Expression of serine protease (SP), a troph marker, and Arp9, a cyst-specific marker, was measured using qRT-PCR. GSC-1 protein immunization significantly reduced the expression of Arp9, while SP expression was unchanged (FIG. 19).

Example 4: Co-Housing Model for *Pneumocystis* Transmission

There are two primary life forms of *Pneumocystis*—the cyst form and the troph form. The cyst form has been shown to be the transmissible form of infection (Cushion et al., *PLoS One* 5(1):e8524, 2010). The data described in Example 3 suggests that GSC-1 is enriched on the cyst form. The primary challenge model with GSC-1 involved infecting mice with both the cyst and troph forms since the *Pneumocystis* is prepared from the lungs of infected animals. Therefore, it is possible that GSC-1 provided only limited protection in the primary challenge model (FIG. 18) because both life forms were present at the time of infection. To test this possibility, a co-housing model is used in which only the cysts are capable of inducing infection. Mice are immunized with recombinant GSC-1 or an irrelevant antigen as a control. Immunized mice are CD4-depleted and housed with a $Rag2^{-/-}Il2rg^{-/-}$ double knockout mouse with high *Pneumocystis* burden. In this model, the $Rag2^{-/-}Il2rg^{-/-}$ double knockout mouse acts as a reservoir of cysts for transmitting the infection in a more physiologically relevant manner than the primary challenge model. It is hypothesized that GSC-1 vaccination will reduce the intensity and number of infected mice four weeks post-initiation of co-housing.

Example 5: Molecular Diagnostics by Detection of Meu10 and GSC-1

The *Pneumocystis* sequences disclosed herein can also be used for diagnosing *Pneumocystis* infection. Diagnostics for *Pneumocystis* are currently limited to modified silver staining and nested PCR assays, which are unable to discriminate between fulminant infection, colonization, and prior infection with residual DNA. As described in the Examples above, GSC-1 and Meu10 are expressed on the cyst and troph form, respectively. *Pneumocystis* is unique in that it has two life forms that appear to serve different roles. The cyst form is the transmissible form and is capable of colonizing the lung. The troph form is the metabolically active and replicative form of *Pneumocystis*. Therefore, a fulminant infection with *Pneumocystis* has increasing numbers of the troph form relative to the cyst form, while colonized patients would only have the cyst form. GSC-1 and Meu10 can therefore be used in molecular diagnostic assays to detect the presence of *Pneumocystis* in a patient.

As one example, a sample is obtained from a patient who is suspected of having a *Pneumocystis* infection. A qRT-PCR assay is performed to amplify Meu10 and/or GSC-1 mRNA present in the sample. The presence of GSC-1 mRNA and absence of Meu10 mRNA in the sample identifies the subject as being colonized with *Pneumocystis*. The presence of both GSC-1 and Meu10 (particularly with GSC-1 mRNA>Meu10 mRNA) identifies the subject as having a fulminant infection with *Pneumocystis.*

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A method of eliciting an immune response in a subject, comprising administering to the subject a GSC-1 protein comprising an amino acid sequence at least 90% identical to residues 22-606 of SEQ ID NO: 111.

2. The method of claim 1, wherein the amino acid sequence of the GSC-1 protein is at least 95% identical to residues 22-606 of SEQ ID NO: 111.

3. The method of claim 1, wherein the amino acid sequence of the GSC-1 protein comprises:

residues 22-606 of SEQ ID NO: 111;

residues 1-606 of SEQ ID NO: 111;

residues 22-641 of SEQ ID NO: 111; or

SEQ ID NO: 111.

4. The method of claim 1, further comprising administering to the subject an adjuvant with the GSC-1 protein.

5. The method of claim 1, wherein:

(a) the immune response comprises generating anti-GSC-1 antibodies; and (b) the GSC-1 protein comprises residues 22-606 of SEQ ID NO: 111.

6. A method of eliciting an immune response in a subject, comprising administering to the subject a GSC-1 protein comprising an amino acid sequence at least 95% identical to residues 22-606 of SEQ ID NO: 111, wherein the amino acid sequence of the GSC-1 protein comprises:

residues 22-606 of SEQ ID NO: 111;

residues 1-606 of SEQ ID NO: 111;

residues 22-641 of SEQ ID NO: 111; or

SEQ ID NO: 111.

7. The method of claim 6, further comprising administering to the subject an adjuvant with the GSC-1 protein.

8. A method of eliciting an immune response in a subject, comprising administering to the subject a GSC-1 protein comprising residues 22-606 of SEQ ID NO: 111.

9. The method of claim 8, further comprising administering to the subject an adjuvant with the GSC-1 protein.

* * * * *